(12) United States Patent
Dyatkin et al.

(10) Patent No.: US 6,960,597 B2
(45) Date of Patent: Nov. 1, 2005

(54) AZA-BRIDGED-BICYCLIC AMINO ACID DERIVATIVES AS α4 INTEGRIN ANTAGONISTS

(75) Inventors: Alexey B. Dyatkin, Maple Glen, PA (US); Bruce E. Maryanoff, Forest Grove, PA (US); William J. Hoekstra, Chapel Hill, NC (US); Wei He, Hillsborough, PA (US); William A. Kinney, Newtown, PA (US)

(73) Assignee: Orth-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/891,602

(22) Filed: Jun. 26, 2001

(65) Prior Publication Data

US 2002/0091115 A1 Jul. 11, 2002

Related U.S. Application Data

(60) Provisional application No. 60/215,695, filed on Jun. 30, 2000.

(51) Int. Cl.[7] ..................... A61K 31/46; C07D 401/12; C07D 221/22
(52) U.S. Cl. ..................... 514/299; 546/112; 548/452; 548/465; 544/127; 544/362; 514/235.2; 514/253; 514/412; 514/414
(58) Field of Search ................. 544/127, 362; 514/235.2, 253, 299, 412, 414, 216, 183; 546/112; 548/452, 465; 540/477, 582

(56) References Cited

U.S. PATENT DOCUMENTS

| | | |
|---|---|---|
| 3,905,971 A | 9/1975 | Miller |
| 5,034,391 A | 7/1991 | Blaschke et al. |
| 5,523,308 A | 6/1996 | Costanzo et al. |
| 5,525,623 A | 6/1996 | Spear et al. |
| 5,827,860 A | 10/1998 | Costanzo et al. |
| 5,827,866 A | 10/1998 | Costanzo et al. |
| 6,090,785 A | 7/2000 | Durette et al. |
| 6,191,171 B1 | 2/2001 | DeLaszlo et al. |
| 6,221,888 B1 | 4/2001 | Durette et al. |
| 6,229,011 B1 | 5/2001 | Chen et al. |
| 6,291,511 B1 | 9/2001 | Durette et al. |
| 6,353,099 B1 | 3/2002 | DeLaszlo et al. |
| 6,380,387 B1 | 4/2002 | Sidduri et al. |
| 6,388,084 B1 | 5/2002 | Kaplan et al. |
| 6,403,584 B1 | 6/2002 | de Laszlo et al. |
| 6,407,066 B1 | 6/2002 | Dressen et al. |
| 6,420,418 B1 | 7/2002 | Hagmann et al. |
| 6,426,348 B1 | 7/2002 | Hull et al. |
| 6,455,550 B1 | 9/2002 | Chen et al. |
| 6,469,036 B1 | 10/2002 | Costanzo et al. |
| 6,479,519 B1 | 11/2002 | Astles et al. |
| 6,479,666 B2 | 11/2002 | Hull et al. |
| 6,521,666 B1 | 2/2003 | Sircar et al. |
| 6,534,513 B1 | 3/2003 | Porter et al. |
| 6,559,174 B2 | 5/2003 | Lin et al. |
| 6,579,889 B2 | 6/2003 | de Laszlo et al. |
| 2002/0019402 A1 | 2/2002 | Dominguez et al. |
| 2002/0085882 A1 | 7/2002 | Konradi et al. |
| 2002/0091115 A1 | 7/2002 | Dyatkin et al. |
| 2002/0133015 A1 | 9/2002 | Kaplan et al. |
| 2002/0137935 A1 | 9/2002 | Head et al. |
| 2002/0197233 A1 | 12/2002 | Relton et al. |
| 2003/0018195 A1 | 1/2003 | Konradi et al. |
| 2003/0027771 A1 | 2/2003 | Dressen et al. |
| 2003/0027850 A1 | 2/2003 | Ashwell et al. |
| 2003/0100585 A1 | 5/2003 | Duplantier et al. |
| 2003/0130166 A1 | 7/2003 | Cunningham |

FOREIGN PATENT DOCUMENTS

| | | |
|---|---|---|
| EP | 0252422 B1 | 7/1999 |
| EP | 0947506 A1 | 10/1999 |
| WO | WO 99/06433 A1 | 2/1990 |
| WO | WO 98/53814 A1 | 12/1998 |

(Continued)

OTHER PUBLICATIONS

PCT Search Report for PCT/US 01/20857 dated Mar. 18, 2002.

Osborn, L.; et al., Cell, 1989, 59, 1203.

(Continued)

*Primary Examiner*—Charanjit S. Aulakh
(74) *Attorney, Agent, or Firm*—Gabriel Lopez; Hal B. Woodrow

(57) ABSTRACT

The invention is directed to aza-bridged-bicyclic compounds having Formula (I):

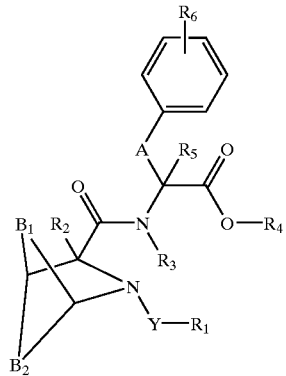

Formula (I)

and pharmaceutically acceptable salts thereof. The compounds are useful (α4 integrin receptor antagonists and, in particular, α4β1 and α4β7 integrin receptor antagonists. The invention is further directed to methods for use of the instant compounds for treating integrin mediated disorders including, but not limited to, inflammatory disorders, autoimmune disorders and cell-proliferative disorders, methods for preparing the compounds and methods for preparing the intermediates, derivatives and pharmaceutical compositions thereof.

42 Claims, No Drawings

FOREIGN PATENT DOCUMENTS

| WO | 98/53814 | * | 12/1998 | ................ 514/315 |
|---|---|---|---|---|
| WO | WO 98/53817 A1 | | 12/1998 | |
| WO | WO 99/06435 A1 | | 2/1999 | |
| WO | WO 99/06436 A1 | | 2/1999 | |
| WO | WO 99/10312 A1 | | 3/1999 | |
| WO | WO 99/10313 A1 | | 3/1999 | |
| WO | WO 99/23063 A1 | | 5/1999 | |
| WO | WO 99/35163 A1 | | 7/1999 | |
| WO | WO 99/36393 A1 | | 7/1999 | |
| WO | WO 99/43642 A1 | | 9/1999 | |
| WO | WO 99/48879 A1 | | 9/1999 | |
| WO | WO 99/61465 A1 | | 12/1999 | |
| WO | WO 99/643900 A1 | | 12/1999 | |
| WO | WO 00/01690 A1 | | 1/2000 | |
| WO | WO 00/18759 A1 | | 4/2000 | |
| WO | WO 00/20396 A1 | | 4/2000 | |
| WO | WO 00/43354 A2 | | 7/2000 | |
| WO | WO 01/14328 A2 | | 3/2001 | |
| WO | WO 01/21584 A1 | | 3/2001 | |
| WO | WO 01/32610 A1 | | 5/2001 | |
| WO | WO 01/42215 A1 | | 6/2001 | |
| WO | WO 01/42225 A2 | | 6/2001 | |
| WO | WO 01/54690 A1 | | 8/2001 | |
| WO | WO 02/08202 A2 | | 1/2002 | |
| WO | WO 02/057242 A2 | | 7/2002 | |
| WO | WO 01/36376 A1 | | 8/2002 | |
| WO | WO 03/010135 A1 | | 2/2003 | |
| WO | WO 02/16329 A1 | | 3/2003 | |
| WO | WO 01/28830 A1 | | 7/2003 | |
| WO | WO 02/22563 A1 | | 7/2003 | |

OTHER PUBLICATIONS

Wayner, E. A.; et al., Cell Biol., 1989, 109, 1321.

Bayless, K. J.; et al., J. Cell Sci., 1998, 111, 1165.

Adams, S. P.; et al., Ann. Rep. Med. Chem., 1999, 34, 179.

Chuluyan, H. E.; et al., Springer Semin. Immunopathol., 1995, 16, 391.

Simmons, P. J.; et al., Blood, 1992, 80, 388.

Shroff, H. N.; et al., Bioorg. Med. Chem. Lett., 1998, 8, 1601.

Yoshikawa, H.; et al., J. Immunol., 1996, 156, 1832.

Laberge, S.; et al., Am. J. Respir. Crit. Care Med., 1995, 151, 822.

Barbadillo, C.; et al., Springer Semin. Immunopathol., 1995, 16, 375.

Powrie, F.; et al., Ther. Immunol., 1995, 2, 115.

Tamraz, S.; et al., Springer Semin. Immunopathol. 1995, 16, 437.

Molossi, S.; et al., J. Clin. Invest. 1995, 95, 2601.

Lin, K–C.; et al., J. Med. Chem. 1999, 42, 920.

Kling D, Fingerle J, Harlan JM, Lobb, RR and Lang, F, Mononuclear leukocytes invade rabbit arterial intima during thickening formation via CD–18 and VLA–4–dependent mechanisms and stimulate smooth muscle migration, Circ. Res., 1995, 77, 1121–1128.

Lumsden AB, Chen C, Hughes JD, Kelly AB, Hanson S and Harker L, Anti–VLA–4 antibody reduces intimal hyperplasis in the endarterectomized carotid artery in non–human primates, J. Vasc. Surg., 1997, 26, 87–93.

Labinez M, Hoeffert C, pels K, Aggarawal S, Pepinsky RB, Leonw D, Koteliansky V, Lobb, RR and O'Brien EO, Infustion on and anti–alpha4 integrin antibody is associated with less adventitial formation after balloon injury of porcine coronary arteries, Can. J. Cardiol., 2000, 16, 187–196.

O'Brien KD, Allen MD, McDonald TO, Chait A, Harlan JM, Fishbein D, McCarty J, Ferguson M, Hudkins K, Benjamin CD, et al., Vascular cell adhesion molecule–1 is expressed in human atherosclerotic plaques: implications for the mode of progression of advanced atherosclerosis, J. Clin. Invest., 1993, 92, 945–951.

Nakahima Y, Raines EW, Plump AS, Breslow JL and Ross R, Upregulation of VCAM–1 and ICAM–1 at atherosclerotic–prone sites on the endothelium of ApoE–deficient mouse, Arterioscler. Thromb. Vasc. Biol., 1998, 18, 842–851.

Ilyama K, Hajra L, Iiyam M, Li,H, DiChura M, Medoff BD and Cybulsky MI, Patterns of vascular cell adhesion molecule–1 and intercellular adhesion molecule–1 expression in rabbit and mouse atherosclerotic lesion and at sites predisposed to lesion formation, Circ. Res., 1999, 85, 199–207.

Shih PT, Brennan M–L, Vora DK, Territo MC, Strahl D, Elices MJ, Aldons J and Berliner JA, Blocking very late antigen–4 integrin decreases leukocyte entry and fatty streak formation in mice fed an atherogenic diet, Circ. Res., 1999, 84, 345–351.

Huo Y, Hafez–Moghadem A and Ley K, Role of vascular cell adhesion molecule–1 and fibronectin connecting segment–1 in monocyte rolling and adhesion on early atherosclerotic lesions, Circ. Res., 2000, 87, 153–159.

Hamann, A.; et al., J. Immunol. 1994, 152, 3282.

Hanninen, A.C.; et al., J. Clin. Invest. 1993, 92, 2509.

Fong, S.; et al., Immunol. Res. 1997, 16, 299.

Yang, X.; et al., Diabetes 1997, 46, 1542.

Gould, Philip L., Ref. International J. Pharm., 1986, 33, 201–217.

Berge et al., J. Pharm.Sci., (Jan., 1997), 66, 1, 1.

W. Abraham et al., "Formamidinoyl Isothiocyanales—III. Addition of Nucleophilic Partners to Formamidinoyl Isothiocyanates," Tetrahedron 29, 669–705 (1973).

* cited by examiner

AZA-BRIDGED-BICYCLIC AMINO ACID DERIVATIVES AS α4 INTEGRIN ANTAGONISTS

This patent application claims benefit of U.S. patent application Ser. No. 60/215,695 filed on Jun. 30, 2000 entitled "AZA-BICYCLIC AMINO ACID DERIVATIVES AS α4 INTEGRIN ANTAGONISTS", which is hereby incorporated by reference.

FIELD OF THE INVENTION

This invention relates to novel compounds and methods for use in treating integrin mediated disorders. More particularly, this invention relates to novel derivatives of aza-bridged-bicyclic amino acid compounds useful as α4 integrin receptor antagonists, methods for treating integrin mediated disorders including, but not limited to, inflammatory, autoimmune and cell-proliferative disorders, methods for preparing the compounds and methods for preparing the intermediates, derivatives and pharmaceutical compositions thereof.

BACKGROUND OF THE INVENTION

Integrin receptors are transmembrane, non-covalently linked heterodimers consisting of one α-chain and one β-chain. In addition to performing a structural adhesive function, integrin receptors transmit extracellular signals across the plasma membrane. The integrin receptor $\alpha_4\beta_1$ (also referred to as VLA-4) mediates cell adhesion by binding with either of two protein ligands: vascular cell adhesion molecule-1 (VCAM-1) (Osborn, L.; et al., *Cell*, 1989, 59, 1203), or the alternatively-spliced fibronectin variant containing the type III connecting segment (CS-1) (Wayner, E. A.; et al., *Cell Biol.*, 1989, 109, 1321). In contrast to the prototypical integrin receptors $\alpha_5\beta_1$, GPIIb/IIIa and $\alpha_v\beta_3$ that recognize the Arg-Gly-Asp (RGD) tripeptide sequence in their respective ligands, $\alpha_4\beta_1$ binds to other primary protein sequences. The $\alpha_4\beta_1$ integrin receptor recognizes Gln-Ile-Asp-Ser (QIDS) in VCAM-1 and Ile-Leu-Asp-Val (ILDV) in fibronectin. Although these sequences share a conserved Asp residue with RGD, they are otherwise unrelated. Additionally, recent studies have found that α4β1 binds the matrix ligand osteopontin (Bayless, K. J.; et al., *J. Cell Sci.*, 1998, 111, 1165). The osteopontin ligand interaction with the $\alpha_4\beta_1$ receptor may be very important as osteopontin is strongly up-regulated in inflammatory settings, including the inflamed lung.

The $\alpha_4\beta_1$ integrin receptor is expressed at high levels on mast cells, mononuclear leukocytes, eosinophils, macrophages, and basophils (Adams, S. P.; et al., *Ann. Rep. Med. Chem.*, 1999, 34, 179). The binding of $\alpha_4\beta_1$ to cytokine-induced VCAM-1 on high-endothelial venules at sites of inflammation results in leukocyte/endothelium adhesion followed by extravasation into the inflamed tissue (Chuluyan, H. E.; et al., *Springer Semin. Immunopathol.*, 1995, 16, 391). The role of mast cells and eosinophils in lung inflammation is well-established. Induction of VCAM-1 expression on airway endothelial cells seems to play a central role in lung inflammation. The α4β1 receptor interaction with VCAM-1 also exerts an important effect in stem cell adhesion to bone marrow stromal cells (Simmons, P. J.; et al., *Blood*, 1992, 80, 388).

The $\alpha_4\beta_7$ integrin is expressed at high levels on lymphocytes and T cells. The trafficking of lymphocytes from the vasculature to normal mucosa and lymphoid tissues is mediated by adhesion of mucosal addressing cell adhesion molecule-1 (MAdCAM-1) with the integrin receptor $\alpha_4\beta_7$. In an inflammatory setting, MAdCAM-1, an immunoglobulin superfamily adhesion molecule, specifically binds $\alpha_4\beta_7$-expressing lymphocytes and participates in the homing of these cells to the mucosal endothelium. Cloning studies of human MAdCAM-1 have shown that the Leu-Asp-Thr-Ser-Leu (LDTSL) sequence of the CD loop is conserved. In fact, LDT-based peptides bind to $\alpha_4\beta_7$ in a MAdCAM-1/RPMI-8866 cell adhesion assay with $IC_{50}$ values in the 1–10 uM range (Shroff, H. N.; et al., *Bioorg. Med. Chem. Lett.*, 1998, 8, 1601).

The extensive biology mediated by integrins in general and compelling data for the pathophysiological role of the leukocyte cell adhesion receptor α4β1 have spurred interest in the study of α4β1 antagonists in vivo. Cellular adhesion and migration mediated through the β1 integrins are critical components of cellular recruitment processes. The integrin α4β1 provides a key co-stimulatory signal supporting cell activation leading to growth factor and cytokine production and mediator release. Through recognition of the extracellular matrix, α4β1 increases the survival of activated cells by inhibiting apoptosis (Yoshikawa, H.; et al., *J. Immunol.*, 1996, 156, 1832).

Monoclonal antibodies directed against α4β1 or VCAM-1 have been shown to be effective modulators in animal models of chronic inflammatory diseases such as asthma (Laberge, S.; et al., *Am. J. Respir. Crit. Care Med.*, 1995, 151, 822), rheumatoid arthritis (Barbadillo, C.; et al., *Springer Semin. Immunopathol.*, 1995, 16, 375) and inflammatory bowel disease (Powrie, F.; et al., *Ther. Immunol.*, 1995, 2, 115). The initial research in the low molecular weight α4β1 antagonist arena has focused on simple linear analogues of the prototype Leu-Asp-Val sequence. Phenylacetyl-Leu-Asp-Phe-D-Pro-NH$_2$ (having an α4β1 $IC_{50}$ value of 2 uM) exhibited efficacy similar to the α4 antibody PS/2 in a mouse model of oxazolone-induced contact hypersensitivity when administered at 6 mg/kg, sc (Tamraz, S.; et al., *Springer Semin. Immunopathol.* 1995, 16, 437). This tetrapeptide was also effective in a hyperlipidemic rabbit heterotopic heart allograft model (Molossi, S.; et al., *J. Clin. Invest.* 1995, 95, 2601).

Animal models of asthma have shown that the peptide antagonist BIO-1211 inhibits eosinophilia and airway hyperresponsiveness (Lin, K-C.; et al., *J. Med. Chem.* 1999, 42, 920). Pre-treatment of allergic sheep with a 3 mg nebulized dose of BIO-121 1 (having an α4β1 $IC_{50}$ value of 1 nM; 1000-fold selective over α4β7) inhibited early and late airway responses following antigen challenge and prevented development of nonspecific airway hyperresponsiveness to carbachol. These results suggest that compounds like BIO-1211 can effect broad pleiotropic activities by acting at α4β1 to achieve pronounced efficacy similar to corticosteroids.

VLA-4 antagonism may also be effective in reducing restenosis following percutaneous coronary interventions. Administration of an anti-α4 antibody attenuated smooth muscle cell migration associated with electrical injury of rabbit carotid arteries (Kling D, Fingerle J, Harlan J M, Lobb, R R and Lang, F, Mononuclear leukocytes invade rabbit arterial intima during thickening formation via CD-18 and VLA-4-dependent mechanisms and stimulate smooth muscle migration, *Circ. Res.*, 1995, 77, 1121–1128) and was shown to reduce neointimal formation in baboon carotid arteries following endarterectomy (Lumsden A B, Chen C, Hughes J D, Kelly A B, Hanson S and Harker L, Anti-VLA-4 antibody reduces intimal hyperplasia in the endarterectomized carotid artery in non-human primates, *J. Vasc. Surg.*, 1997, 26, 87–93). Furthermore, treatment with z anti-α4 antibody was associated with less neoadventitia formation and less lumenal narrowing 14 days after balloon injury of porcine coronary arteries (Labinez M, Hoffert C, pels K, Aggarawal S, Pepinsky R B, Leonw D, Koteliansky V, Lobb, R R and O'Brien E O, Infusion on and anti-alpha4 integrin antibody is associated with less adventitial formation after balloon injury of porcine coronary arteries, *Can. J. Cardiol.*, 2000, 16, 187–196).

The recruitment of leukocytes, particularly monocytes to the vessel wall is a key component in the development of atherosclerotic lesions. VCAM-1 expression has been reported on endothelial cells in atherosclerotic lesions in humans (O'Brien K D, Allen M D, McDonald T O, Chait A, Harlan J M, Fishbein D, McCarty J, Ferguson M, Hudkins K, Benjamin C D, et al., Vascular cell adhesion molecule-1 is expressed in human atherosclerotic plaques: implications for the mode of progression of advanced atherosclerosis, *J. Clin. Invest.*, 1993, 92, 945–951), mice (Nakahima Y, Raines E W, Plump A S, Breslow J L and Ross R, Upregulation of VCAM-1 and ICAM-1 at atherosclerotic-prone sites on the endothelium of ApoE-deficient mouse, *Arterioscler. Thromb. Vasc. Biol.*, 1998, 18, 842–851) and rabbits (Ilyama K, Hajra L, Iiyam M, Li, H, DiChura M, Medoff B D and Cybulsky M I, Patterns of vascular cell adhesion molecule-1 and intercellular adhesion molecule-1 expression in rabbit and mouse atherosclerotic lesion and at sites predisposed to lesion formation, *Circ. Res.*, 1999, 85, 199–207). Furthermore, a synthetic peptidomimetic of the connecting segment-1 (CS-1) which blocks $\alpha_4\beta_1$ on the leukocyte demonstrated reduced leukocyte homing and lipid accumulation in the aortic sinus in both wild type mice and mice with a low density lipoprotein null mutation (LDLR -/-) maintained on a high fat diet (Shih P T, Brennan M-L, Vora D K, Territo M C, Strahl D, Elices M J, Aldons J and Berliner J A, Blocking very late antigen-4 integrin decreases leukocyte entry and fatty streak formation in mice fed an atherogenic diet, *Circ. Res.*, 1999, 84, 345–351). In studies using isolated carotid arteries from ApoE -/-mice (these mice develop spontaneous arterial atherosclerotic lesions with advanced lesions similar to those observed in humans), administration on blocking antibodies to VCAM-1 inhibited the majority of adhesion of monocytes or U937 cells on early atherosclerotic endothelia. In addition, a peptide which inhibits binding of $\alpha 4\beta 1$ to both VCAM-1 and fibronectin was also effective in this model (Huo Y, Hafez-Moghadem A and Ley K, Role of vascular cell adhesion molecule-1 and fibronectin connecting segment-1 in monocyte rolling and adhesion on early atherosclerotic lesions, *Circ. Res.*, 2000, 87, 153–159). These data support the role of $a_4\beta_1$ in regulating leukocyte recruitment in early and advanced atherosclerotic lesions.

Antibodies to MAdCAM-1 or integrin $\alpha 4\beta 7$ inhibit lymphocyte binding to affinity-purified MAdCAM-1 or MAdCAM-1 transfectants in vitro (Hamann, A.; et al., *J. Immunol.* 1994, 152, 3282). The antibodies also block localization of lymphocytes to Peyer's patches. Murine MAdCAM-1 recognizes only $\alpha 4\beta 7$ positive human lymphocyte cells lines and $\alpha 4\beta 7$-high memory T cells. An in vivo role of $\alpha 4\beta 7$ in inflammation has been suggested by increased expression of MAdCAM-1 on HEV-type vessels in the chronically inflamed pancreas of the non-obese mouse (Hanninen, A. C.; et al., *J. Clin. Invest.* 1993, 92, 2509). In fact, animal models underscore a significant function of $\alpha 4\beta 7$ in both colitis (Fong, S.; et al., *Immunol. Res.* 1997, 16, 299) and lymphocytic inflammation of pancreatic islets or development of diabetes (Yang, X.; et al., *Diabetes* 1997, 46, 1542).

PCT application WO 98/53814 describes heterocyclic amide compounds as antagonists for VLA-4 and/or $\alpha 4\beta_7$ antagonists of the formula:

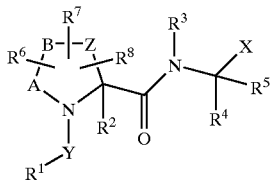

or a pharmaceutically acceptable salt thereof wherein $R^1$ is alkyl, alkenyl, alkynyl, $C_y$, $C_y$-alkyl, $C_y$-alkenyl or $C_y$-alkynyl; wherein alkyl, alkenyl and alkynyl are optionally substituted with $R^a$; and $C_y$ is optionally substituted with $R^b$; $R^2$ is hydrogen, alkyl, alkenyl, alkynyl, aryl, aralkyl, heteroaryl or heteroaralkyl; wherein alkyl, alkenyl and alkynyl are optionally substituted with $R^a$; and aryl and heteroaryl are optionally substituted with $R^b$; $R^3$ is hydrogen, alkyl, $C_y$ or $C_y$-alkyl; wherein alkyl is optionally substituted with $R^a$; and $C_y$ is optionally substituted with $R^b$; $R^4$ is hydrogen, alkyl, alkenyl, alkynyl, $C_y$, $C_y$-alkyl, $C_y$-alkenyl or $C_y$-alkynyl; wherein alkyl, alkenyl and alkynyl are optionally substituted with phenyl and $R^x$; and $C_y$ is optionally substituted with $R^y$; or, $R^3$, $R^4$ and the atoms to which they are attached together form a mono- or bicyclic ring containing 0–2 additional heteroatoms selected from N, O and S; $R^5$ is hydrogen, alkyl, alkenyl, alkynyl, aryl, aralkyl, heteroaryl or heteroaralkyl; wherein alkyl, alkenyl and alkynyl are optionally substituted with $R^x$; and aryl and heteroaryl are optionally substituted with $R^y$; or, $R^4$, $R^5$ and the carbon to which they are attached together form a 3–7 membered mono- or bicyclic ring containing 0–2 heteroatoms selected from N, O and S; $R^6$, $R^7$ and $R^8$ are each independently selected from $R^d$ or $R^x$; or, two of $R^6$, $R^7$ and $R^8$ and the atom to which both are attached, or two of $R^6$, $R^7$ and $R^8$ and the two adjacent atoms to which they are attached together form a 5–7 membered saturated or unsaturated monocyclic ring containing 0–3 heteroatoms selected from N, O or S; $R^a$ is $C_y$, or a group selected from $R^x$; wherein $C_y$ is optionally substituted with $R^c$; $R^b$ is a group selected from $R^a$, alkyl, alkenyl, alkynyl, aralkyl or heteroaralkyl; wherein alkyl, alkenyl, alkynyl, aryl and heteroaryl are optionally substituted with $R^c$; $R^b$ is halogen, $NO_2$, $C(O)OR^f$, alkyl, alkoxy, aryl, aralkyl, aryloxy, heteroaryl, $NR^fR^g$, $NR^fC(O)R^g$, $NR^fC(O)NR^fR^g$, or CN; $R^d$ and $R^e$ are independently selected from hydrogen, alkyl, alkenyl, alkynyl, $C_y$ and $C_y$-alkyl; wherein alkyl, alkenyl, alkynyl and $C_y$ are optionally substituted with $R^c$; or, $R^d$ and $R^e$ together with the atoms to which they are attached form a heterocyclic ring of 5–7 members containing 0–2 additional heteroatoms independently selected from N, O and S; $R^f$ and $R^g$ are independently selected from hydrogen, alkyl, $C_y$ and $C_y$-alkyl; wherein $C_y$ is optionally substituted with alkyl; or, $R^f$ and $R^g$ together with the carbon to which they are attached form a ring of 5–7 members containing 0–2 heteroatoms independently selected from N, O and S; $R^h$ is hydrogen, alkyl, alkenyl, alkynyl, cyano, aryl, aralkyl, heteroaryl, heteroaralkyl or —$SO_2R^i$; wherein alkyl, alkenyl and alkynyl are optionally substituted with $R^a$; and aryl and heteroaryl are optionally substituted with $R^b$; $R^i$ is alkyl, alkenyl, alkynyl or aryl; wherein alkyl, alkenyl, alkynyl and aryl are each optionally substituted with $R^c$; $R^k$ is —$OR^d$, —$NO_2$, halogen, —$S(O)_mR^d$, —$SR^d$, —$S(O_2)OR^d$, —$S(O)_m$ $NR^dR^e$, —$NR^dR^e$, —$O(CR^fR^g)_nNR^dR^e$, —$C(O)$ $R^d$, —$CO_2R^d$, —$CO_2(C$ $R^fR^g)_nC(O)N$ $R^dR^e$, —$OC(O)R^d$, CN, C(O)NR$^d$R$^e$, —NR$^d$C(O)R$^e$, —OC(O)NR$^d$R$^e$, —NR$^d$C(O)OR$^e$, —NR$^d$C(O)NR$^d$R$^e$, —CR$^d$(N—OR$^e$), —CF$_3$, oxo, —NR$^d$C(O)NR$^d$SO$_2$R$^i$, —NR$^d$S(O)$_m$R$^e$, —OS(O$_2$)OR$^d$ or —OP(O)(OR$^d$)$_2$; R$^y$ is a group selected from R$^k$, alkyl, alkenyl, alkynyl, aralkyl, heteroaralkyl, cycloalkyl or heterocyclyl; wherein alkyl, alkenyl, alkynyl and aryl are each optionally substituted with R$^x$; C$_y$ is cycloalkyl, heterocyclyl, aryl or heteroaryl; m is an integer from 1 to 2; n is an integer from 1 to 10; X is —C(O)OR$^d$, —P(O)(OR$^d$)(OR$^e$), —P(O)(R$^d$)(OR$^e$), —S(O)$_m$OR$^d$, C(O)NR$^d$R$^h$ or -5-tetrazolyl; Y is —C(O)—, —O—C(O)—, —NR$^e$C(O)—, —SO$_2$—, —P(O)(OR$^4$) or C(O)C(O); Z and A are independently selected from —C— and —C—C—; and, B is selected from the group consisting of a bond, —C—, —C—C—, —C=C—, a heteroatom selected from the group consisting of N, O and S; and —S(O)$_m$—. Specific examples which exemplify some of the typical compounds disclosed have the following typical formulae:

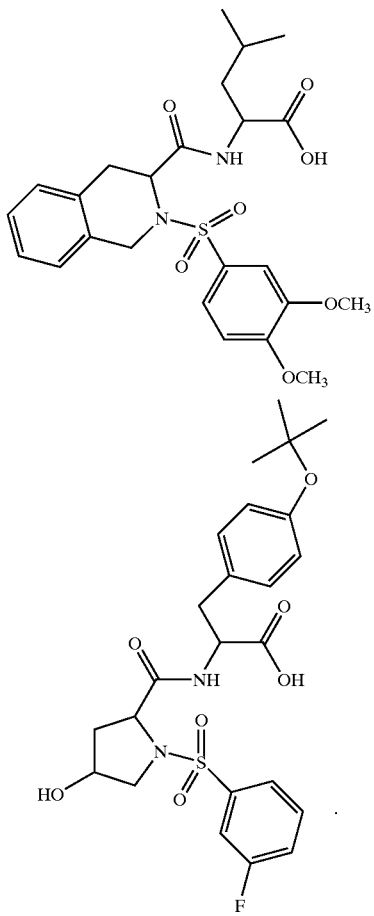

PCT application WO 00/43354 describes multicyclic compounds as inhibitors of leukocyte adhesion mediated by VLA-4 of the formula:

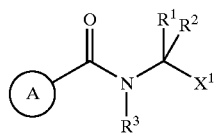

wherein ring A is a multicyclic bridged cycloalkyl, multicyclic bridged cycloalkenyl or multicyclic bridged heterocyclic group provided the multicyclic bridged heterocyclic group does not contain a lactam and further wherein said multicyclic bridged cycloalkyl, multicyclic bridged cycloalkenyl or multicyclic bridged heterocyclic group is optionally substituted, on any ring atom capable of substitution, with 1–3 substituents selected from the group consisting of alkyl, substituted alkyl, alkoxy, substituted alkoxy, acyl, acylamino, thiocarbonyl-amino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, carboxylalkyl, carboxyl-substituted alkyl, carboxyl-cycloalkyl, carboxyl-substituted cycloalkyl, carboxylaryl, carboxyl- substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ And —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl; R$^1$ is selected from the group consisting of: (a) —(CH$_2$)$_x$—Ar—R$^5$ where R$^5$ is selected from the group consisting of —O—Z—NR$^6$R$^{6'}$ and —O—Z—R$^7$ wherein R$^6$ and R$^{6'}$ are independently selected from the group consisting of hydrogen, alkyl, substituted alkyl, cycloalkyl, substituted cycloalkyl, heterocyclic, substituted heterocyclic, and where R$^6$ and R$^{6'}$ are joined to form a heterocycle or a substituted heterocycle, R$^7$ is selected from the group consisting of heterocycle and substituted heterocycle, and Z is selected from the group consisting of —C(O)— and —SO₂—, Ar is aryl, heteroaryl, substituted aryl or substituted heteroaryl, x is an integer of from 1 to 4; (b) Ar¹—Ar²—C$_{1-10}$alkyl—, Ar¹—Ar²—C$_{2-10}$alkenyl—, Ar¹—Ar²—C$_{2-10}$alkynyl-, wherein Ar¹ and Ar² are independently aryl or heteroaryl each of which is optionally substituted with one to four substituents independently selected from R$^b$; alkyl, alkenyl and alkynyl are optionally substituted with one to four substituents independently selected from R$^a$; (c) —(CH₂)$_x$—Ar—R⁸, wherein R⁸ is heterocyclic or substituted heterocyclic; Ar is aryl, heteroaryl, substituted aryl or substituted heteroaryl, x is an integer of from 1 to 4; (d) —(CH₂)$_x$—Ar—R⁹, wherein R⁹ is —C$_{1-10}$alkyl, —C$_{2-10}$alkenyl or —C$_{2-10}$alkynyl, wherein alkyl, alkenyl and alkynyl are optionally substituted with one to four substituents selected from R$^a$; Ar is aryl, heteroaryl, substituted aryl or substituted heteroaryl, x is an integer of from 1 to 4; (e) —(CH₂)$_x$—Cy—, wherein Cy is optionally substituted with 1 to 4 substituents selected from R$^a$ is selected from the group consisting of hydrogen, C$_{1-10}$alkyl, C$_{2-10}$alkenyl, C$_{2-10}$alkynyl, aryl, aryl C$_{1-10}$alkyl, heteroaryl, and heteroaryl C$_{1-10}$alkyl, wherein alkyl, alkenyl and alkynyl are optionally substituted with one to four substituents selected from R$^a$, and aryl and heteroaryl are optionally substituted with one to four substituents independently selected from R$^b$; R³ is selected from the group consisting of hydrogen, C$_{1-10}$alkyl optionally substituted with one to four substituents independently selected from R$^a$ and Cy optionally substituted with one to four substituents independently selected from R$^b$; R$^a$ is selected from the group consisting of Cy, —OR$^d$, —NO₂, halogen, —S(O)$_m$R$^d$, —SR$^d$, —S(O)₂OR$^d$, —S(O)$_m$NR$^d$R$^e$, NR$^d$R$^e$, —O(CNR$^f$R$^g$)$_n$NR$^d$R$^e$, —C(O)R$^d$, —CO₂R$^d$, —CO₂(CR$^f$R$^g$)$_n$CONR$^d$R$^e$, —OC(O)R$^d$, —CN, C(O)NR$^d$R$^e$, NR$^d$C(O)R$^e$, —OC(O)NR$^d$R$^e$, —NR$^d$C(O)OR$^e$, —NR$^d$C(O)NR$^d$R$^e$, —CR$^d$(N—OR$^e$), CF₃, and —OCF₃; wherein Cy is optionally substituted with one to four substituents independently selected from R$^c$; R$^b$ is selected from the group consisting of R$^a$, C$_{1-10}$alkyl, C$_{2-10}$alkenyl, C$_{2-10}$alkynyl, aryl C$_{1-10}$alkyl, heteroaryl, C$_{1-10}$alkyl, wherein alkyl, alkenyl, aryl, heteroaryl are optionally substituted with a group independently selected from R$^c$; R$^c$ is selected from the group consisting of halogen, amino, carboxy, C$_{1-4}$alkyl, C$_{1-4}$alkoxy, aryl, aryl C$_{1-4}$alkyl, hydroxy, CF₃, and aryloxy; R$^d$ and R$^e$ are independently selected from hydrogen, C$_{1-10}$alkyl, C$_{2-10}$alkenyl, C$_{2-10}$alkynyl, Cy and Cy—C$_{1-10}$alkyl, wherein alkyl, alkenyl, alkynyl and Cy are optionally substituted with one to four substituents independently selected from R$^c$; or R$^d$ and R$^e$ together with the atoms to which they are attached form a heterocyclic ring of 5 to 7 members containing 0–2 additional heteroatoms independently selected from oxygen, sulfur and nitrogen; R$^f$ and R$^g$ are independently selected from hydrogen, C$_{1-10}$alkyl, Cy and Cy—C$_{1-10}$alkyl; or R$^a$ R$^f$ and R$^a$ R9 together with the carbon to which they are attached form a ring of 5 to 7 members containing 0–2 heteroatoms independently selected from oxygen, sulfur and nitrogen; R$^h$ is selected from the group consisting of hydrogen, C$_{1-10}$alkyl, C$_{2-10}$alkenyl, C$_{2-10}$alkynyl, cyano, aryl, aryl C$_{1-10}$alkyl, heteroaryl, heteroaryl C$_{1-10}$alkyl, or —SO₂R$^i$; wherein alkyl, alkenyl, and alkynyl are optionally substituted with one to four substitutents independently selected from R$^a$; and aryl and heteroaryl are each optionally substituted with one to four substituents independently selected from R$^b$; R$^i$ is selected from the group consisting of C$_{1-10}$alkyl, C$_{2-10}$alkenyl, C$_{2-10}$alkynyl, and aryl; wherein alkyl, alkenyl, alkynyl and aryl are each optionally substituted with one to four substituents independently selected from R$^c$; Cy is cycloalkyl, heterocyclyl, aryl, or heteroaryl; X¹ is selected from the group consisting of —C(O)OR$^d$, —P(O)(OR$^d$)(OR$^e$), —P(O)(R$^d$)(OR$^e$), —S(O)$_m$OR$^d$, —C(O)NR$^d$R$^h$, and -5-tetrazolyl; m is an integer from 1 to 2; n is an integer from 1 to 10; and pharmaceutically acceptable salts thereof. Preferred compounds of this invention are represented by formula II:

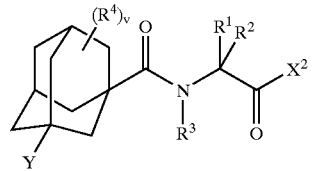

wherein R¹, R² and R³ are as defined above; Y is selected from the group consisting of hydrogen, R$^d$, Cy, —OR$^d$, —NO₂, halogen, —S(O)$_m$R$^d$, —SR$^d$, —S(O)₂OR$^d$, —S(O)$_m$ NR$^d$R$^e$, —NR$^d$R$^e$, —O(CR$^f$R$^g$)$_n$NR$^d$R$^e$, —C(O)R$^d$, —CH(OH)R$^d$, —CO₂R$^d$, —CO₂(CR$^f$R$^g$)$_n$CONR$^d$R$^e$, —OC(O)R$^d$, —CN, C(O)NR$^d$R$^e$, NR$^d$C(O)R$^e$, —OC(O)NR$^d$R$^e$, —NR$^d$C(O)OR$^e$, —NR$^d$C(O)NR$^d$R$^e$, —CR$^d$(N—OR$^e$), CF₃, and —OCF₃; wherein Cy is optionally substituted with one to four substituents independently selected from R$^c$; where Cy, R$^c$, R$^d$, R$^e$, R$^f$, R$^g$, R$^h$, m and n are as defined herein; R⁴ is selected from the group consisting of alkyl, substituted alkyl, alkoxy, substituted alkoxy, acyl, acylamino, thiocarbonyl-amino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, carboxylalkyl, carboxyl-substituted alkyl, carboxyl-cycloalkyl, carboxyl-substituted cycloalkyl, carboxylaryl, carboxyl-substituted aryl, carboxyllieteroaryl, carboxyl-substituted heteroaryl, carboxyllieterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thiolheteroaryl, substituted thiolheteroaryl, thiolheterocyclic, substituted thiolheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂-NRR where each R is independently hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, —N[S(O)₂—R']₂ and —N[S(O)₂—NR']₂ where each R' is independently selected from the group consisting of alkyl, substituted alkyl, aryl, substituted aryl, heteroaryl, substituted heteroaryl, heterocyclic and substituted heterocyclic, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl; or $R^b$ where $R^b$ is as defined above; $X^2$ is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic; or $R^d$ where $R^d$ is as defined above; v is an integer ranging from 0 to 3; and pharmaceutically acceptable salts thereof.

The structural topology represented by the formulae described in these references differs significantly from that represented by the compounds of the present invention.

Accordingly, it is an object of the present invention to provide aza-bridged-bicyclic compounds that are α4 integrin receptor antagonists; more particularly, the $\alpha_4\beta_1$ and the $\alpha_4\beta_7$ integrin receptor. It is also an object of the present invention to provide a process for preparing derivatives of aza-bridged-bicyclic amino acid compounds, compositions, intermediates and derivatives thereof. It is a further object of the invention to provide methods for the treatment of integrin mediated disorders that are ameliorated by inhibition of the $\alpha_4\beta_1$ and $\alpha_4\beta_7$ integrin receptor including, but not limited to, inflammatory, autoimmune and cell-proliferative disorders.

SUMMARY OF THE INVENTION

The present invention is directed to aza-bridged-bicyclic compounds having Formula (I):

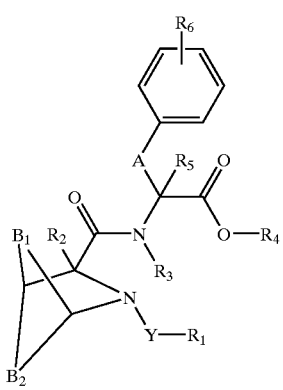

Formula (I)

wherein
Y is selected from the group consisting of a bond, —C(O)—, —C(O)O—, —C(O)NH— and —SO$_2$—;
$R_1$ is selected from the group consisting of $R_7$ and $R_8$;
$R_2, R_3, R_4$ and $R_5$ are independently selected from the group consisting of a bond, hydrogen and C$_{1-8}$alkyl; wherein C$_{1-8}$alkyl is optionally substituted with one to three substituents independently selected from $R_9$, provided that $R_2, R_3, R_4$ or $R_5$ can only be a bond when forming a monocyclic ring wherein the following monocyclic rings may be formed from $R_2, R_3, R_4$ and $R_5$;

when $R_2$ and $R_3$ comprise a bond and C$_{1-8}$alkyl or optionally when both $R_2$ and $R_3$ are C$_{1-8}$alkyl, $R_2$ and $R_3$ together with the atoms to which each is attached will form a four to seven membered monocyclic ring optionally containing one to two additional heteroatoms independently selected from the group consisting of N, O and S;

when $R_3$ and $R_4$ comprise a bond and C$_{1-8}$alkyl or optionally when both $R_3$ and $R_4$ are C$_{1-8}$alkyl, $R_3$ and $R_4$ together with the atoms to which each is attached will form a five to seven membered monocyclic ring optionally containing one to two additional heteroatoms independently selected from the group consisting of N, O and S;

when $R_3$ and $R_5$ comprise a bond and C$_{1-8}$alkyl or optionally when both $R_3$ and $R_5$ are C$_{1-8}$alkyl, $R_3$ and $R_5$ together with the atoms to which each is attached will form a four to seven membered monocyclic ring optionally containing one to two additional heteroatoms independently selected from the group consisting of N, O and S;

when $R_4$ and $R_5$ comprise a bond and C$_{1-8}$alkyl, or optionally when both $R_4$ and $R_5$ are C$_{1-8}$alkyl, $R_4$ and $R_5$ together with the atoms to which each is attached will form a four to seven membered monocyclic ring optionally containing one to two additional heteroatoms independently selected from the group consisting of N, O and S;

$R_6$ is optionally present and is one to three substituents independently selected from the group consisting of halogen, C$_{1-8}$alkoxy, $R_{10}$, $R_{12}$, —N($R_{11}$)C(O)—$R_{10}$, —N($R_{11}$)C(O)—$R_{12}$, —N($R_{11}$)SO$_2$—$R_{10}$, —N($R_{11}$)SO$_2$—$R_{12}$, —N($R_{11}$)C(O)—N($R_{11}$, $R_{10}$), —N($R_{11}$)C(O)—N($R_{11}$, $R_{12}$), —N($R_{11}$)C(O)—N($R_{12}$, $R_{17}$), —C(O)—N($R_{11}$, $R_{10}$), —C(O)—N($R_{11}$, $R_{12}$), —C(O)—N($R_{12}$, $R_{17}$), —OC(O)—N($R_{11}$, $R_{10}$), —OC(O)—N($R_{11}$, $R_{12}$), —OC(O)—N($R_{12}$, $R_{17}$), —OC(O)—$R_{10}$, —OC(O)—$R_{12}$, —O—$R_{10}$ and $R_{10}$—(C$_{1-8}$)alkoxy;

$R_7$, $R_9$ $R_{10}$ and $R_{14}$ are independently selected from the group consisting of cycloalkyl, heterocyclyl, aryl and heteroaryl optionally substituted with one to five substituents independently selected from the group consisting of halogen, C$_{1-8}$alkyl, C$_{2-8}$alkenyl, C$_{2-8}$alkynyl, C$_{1-8}$alkoxy, C$_{1-8}$alkylcarbonyl, C$_{1-8}$alkoxycarbonyl, carboxyl, aryl, heteroaryl, arylcarbonyl, heteroarylcarbonyl, arylsulfonyl, amino, N—(C$_{1-8}$alkyl)amino, N,N—(C$_{1-8}$dialkyl)amino, —CF$_3$ and —OCF$_3$; wherein cycloalkyl and heterocyclyl are optionally substituted with one to three oxo substituents; and, wherein the aryl and heteroaryl substituents and the aryl portion of the arylcarbonyl substituent are optionally substituted with one to five substituents independently selected from the group consisting of halogen, C$_{1-8}$alkyl, C$_{2-8}$alkenyl, C$_{2-8}$alkynyl, C$_{1-8}$alkoxy, carboxyl, amino, N—(C$_{1-8}$alkyl)amino, N,N—(C$_{1-8}$dialkyl)amino, —CF$_3$ and —OCF$_3$;

$R_8$, $R_{12}$, $R_{13}$ and $R_{17}$ are independently selected from the group consisting of C$_{1-8}$alkyl, C$_{2-8}$alkenyl, C$_{2-8}$alkynyl, and (halo)$_{1-3}$(C$_{1-8}$)alkyl; wherein C$_{1-8}$alkyl, C$_{2-8}$alkenyl and C$_{2-8}$alkynyl are optionally substituted on a terminal carbon with one to three substituents independently selected from $R_{14}$;

$R_{11}$ is selected from the group consisting of hydrogen and C$_{1-8}$alkyl;

A is C$_{1-4}$alkylene optionally substituted with one to two substituents independently selected from $R_{13}$;

when R$_3$ is C$_{1-8}$alkyl, optionally A and R$_3$ together with the atoms to which each is attached may form a five to seven membered monocyclic ring optionally containing one to two additional heteroatoms independently selected from the group consisting of N, O and S;

when R$_4$ is C$_{1-8}$alkyl, optionally A and R$_4$ together with the atoms which each is attached may form a five to seven membered monocyclic ring optionally containing one additional heteroatom selected from the group consisting of N, O and S;

when R$_5$ is C$_{1-8}$alkyl, optionally A and R$_5$ together with the atoms which each is attached may form a three to seven membered monocyclic ring optionally containing one to two heteroatoms independently selected from the group consisting of N, O and S; and, B$_1$ and B$_2$ are independently selected from the group consisting of C$_{1-8}$alkylene and C$_{2-8}$alkenylene optionally substituted with one to two substituents independently selected from the group consisting of halogen, hydroxy, hydroxy(C$_{1-8}$)alkyl, hydroxy(C$_{1-8}$)alkoxy, C$_{1-8}$alkyl, C$_{2-8}$alkenyl, C$_{2-8}$alkynyl, C$_{1-8}$alkoxy, carboxyl, amino, N—(C$_{1-8}$alkyl)amino, N,N—(C$_{1-8}$dialkyl)amino, —CF$_3$ and —OCF$_3$;

and pharmaceutically acceptable salts, racemic mixtures, diastereomers and enantiomers thereof.

An embodiment of the present invention is directed to aza-bridged-bicyclic compounds having Formula (II):

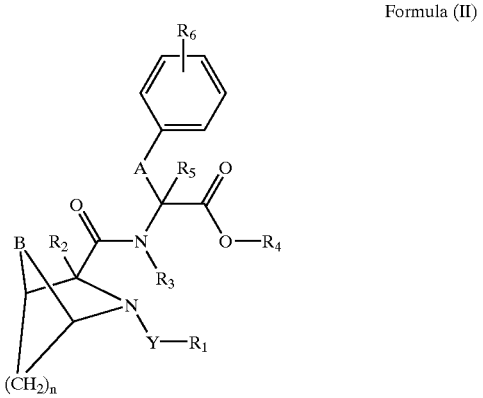

Formula (II)

wherein

Y is selected from the group consisting of —C(O)— and —SO$_2$—;

R$_1$ is selected from the group consisting of R$_7$ and R$_8$;

R$_2$, R$_3$, R$_4$ and R$_5$ are independently selected from the group consisting of a bond, hydrogen and C$_{1-8}$alkyl; wherein C$_{1-8}$alkyl is optionally substituted with one to three substituents independently selected from R$_9$; provided that R$_2$, R$_3$, R$_4$ and R$_5$ can only be a bond when forming a monocylic ring wherein the following monocylic rings may be formed from R$_2$, R$_3$, R$_4$ and R$_5$:

when R$_2$ and R$_3$ comprise a bond and C$_{1-8}$alkyl or optionally when both R$_2$ and R$_3$ are C$_{1-8}$alkyl, R$_2$ and R$_3$ together with the atoms to which each are attached form a four to seven membered monocyclic ring optionally containing one to two additional heteroatoms independently selected from the group consisting of N, O and S;

when R$_3$ and R$_4$ comprise a bond and C$_{1-8}$alkyl or optionally when both R$_3$ and R$_4$ are C$_{1-8}$alkyl, R$_3$ and R$_4$ together with the atoms to which each are attached form a five to seven membered monocyclic ring optionally containing one to two additional heteroatoms independently selected from the group consisting of N, O and S;

when R$_3$ and R$_5$ comprise a bond and C$_{1-8}$alkyl or optionally when both R$_3$ and R$_5$ are C$_{1-8}$alkyl, R$_3$ and R$_5$ together with the atoms to which each are attached form a four to seven membered monocyclic ring optionally containing one to two additional heteroatoms independently selected from the group consisting of N, O and S;

when R$_4$ and R$_5$ comprise a bond and C$_{1-8}$alkyl or optionally when both R$_4$ and R$_5$ are C$_{1-8}$alkyl, R$_4$ and R$_5$ together with the atoms to which each are attached form a four to seven membered monocyclic ring optionally containing one to two additional heteroatoms independently selected from the group consisting of N, O and S;

R$_6$ is optionally present and is one to three substituents independently selected from the group consisting of halogen, C$_{1-8}$alkoxy, R$_{10}$, R$_{12}$, —N(R$_{11}$)C(O)—R$_{10}$, —N(R$_{11}$)C(O)—R$_{12}$, —N(R$_{11}$)SO$_2$—R$_{10}$, —N(R$_{11}$)SO$_2$—R$_{12}$, —N(R$_{11}$)C(O)—N(R$_{11}$, R$_{10}$), —N(R$_{11}$)C(O)—N(R$_{11}$, R$_{12}$), —N(R$_{11}$)C(O)—N(R$_{12}$, R$_{17}$), —C(O)—N(R$_{11}$, R$_{10}$), —C(O)—N(R$_{11}$, R$_{12}$), —C(O)—N(R$_{12}$, R$_{17}$), —OC(O)—N(R$_{11}$, R$_{10}$), —OC(O)—N(R$_{11}$, R$_{12}$), —OC(O)—N(R$_{12}$, R$_{17}$), —OC(O)—R$_{10}$, —OC(O)—R$_{12}$, —O—R$_{10}$ and R$_{10}$—(C$_{1-8}$)alkoxy;

R$_7$, R$_9$, R$_{10}$ and R$_{14}$ are independently selected from the group consisting of cycloalkyl, heterocyclyl, aryl and heteroaryl optionally substituted with one to five substituents independently selected from the group consisting of halogen, C$_{1-8}$alkyl, C$_{2-8}$alkenyl, C$_{2-8}$alkynyl, C$_{1-8}$alkoxy, C$_{1-8}$alkylcarbonyl, C$_{1-8}$alkoxycarbonyl, carboxyl, aryl, heteroaryl, arylcarbonyl, heteroarylcarbonyl, arylsulfonyl, amino, N—(C$_{1-8}$alkyl)amino, N,N—(C$_{1-8}$dialkyl)amino, —CF$_3$ and —OCF$_3$; wherein cycloalkyl and heterocyclyl are optionally substituted with one to three oxo substituents; and, wherein the aryl and heteroaryl substituents and the aryl portion of the arylcarbonyl substituent are optionally substituted with one to five substituents independently selected from the group consisting of halogen, C$_{1-8}$alkyl, C$_{2-8}$alkenyl, C$_{2-8}$alkynyl, C$_{1-8}$alkoxy, carboxyl, amino, N—(C$_{1-8}$alkyl)amino, N,N—(C$_{1-8}$dialkyl)amino, —CF$_3$ and —OCF$_3$;

R$_8$, R$_{12}$, R$_{13}$ and R$_{17}$ are independently selected from the group consisting of C$_{1-8}$alkyl, C$_{2-8}$alkenyl, C$_{2-8}$alkynyl, and (halo)$_{1-3}$(C$_{1-8}$)alkyl; wherein C$_{1-8}$alkyl, C$_{2-8}$alkenyl and C$_{2-8}$alkynyl are optionally substituted on a terminal carbon with one to three substituents independently selected from R$_{14}$;

R$_{11}$ is selected from the group consisting of hydrogen and C$_{1-8}$alkyl;

A is C$_{1-4}$alkylene optionally substituted with one to two substituents independently selected from R$_{13}$;

when R$_3$ is C$_{1-8}$alkyl, optionally A and R$_3$ together with the atoms to which each is attached form a five to seven membered monocyclic ring optionally containing one to two additional heteroatoms independently selected from the group consisting of N, O and S;

when R$_4$ is C$_{1-8}$alkyl, optionally A and R$_4$ together with the atoms to which each is attached form a five to seven membered monocyclic ring optionally containing one additional heteroatom selected from the group consisting of N, O and S;

when $R_5$ is $C_{1-8}$alkyl, optionally A and $R_3$together with the atoms to which each is attached form a three to seven membered monocyclic ring optionally containing one to two heteroatoms independently selected from the group consisting of N, O and S;

B is selected from the group consisting of $C_{1-8}$alkylene and $C_{2-8}$alkenylene optionally substituted with one to two substituents independently selected from the group consisting of halogen, hydroxy, hydroxy($C_{1-8}$)alkyl, hydroxy($C_{1-8}$)alkoxy, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$; and, n is an integer from 1 to 2;

and pharmaceutically acceptable salts, racemic mixtures, diastereomers and enantiomers thereof.

An embodiment of the present invention is also directed to a process for preparing the instant aza-bridged-bicyclic compounds, compositions, intermediates and derivatives thereof. Another embodiment of the present invention is directed to pharmaceutical compositions comprising the compounds of the present invention.

The aza-bridged-bicyclic amino acid derivatives of the present invention are useful α4 integrin receptor antagonists and, more particularly, $\alpha_4\beta_1$ and $\alpha_4\beta_7$ integrin receptor antagonists. A further embodiment of the present invention is directed to a method for the treatment of integrin mediated disorders that are ameliorated by inhibition of the $\alpha_4\beta_1$ and $\alpha_4\beta_7$ integrin receptor including, but not limited to, inflammatory, autoimmune and cell-proliferative disorders. In an illustration of the invention, the inflammatory, autoimmune and cell-proliferative disorders include, but are not limited to, inflammation and autoimmunity, asthma and bronchoconstriction, restenosis and atherosclerosis, psoriasis, rheumatoid arthritis, inflammatory bowel disease, transplant rejection and multiple sclerosis.

DETAILED DESCRIPTION OF THE INVENTION

We have discovered that the position and type of the substituents on the phenyl group of the phenylalanine amino acid, in combination with stereochemistry, have a significant effect on the $\alpha_4\beta_1$ and $\alpha_4\beta_7$ integrin receptor antagonist activity of the aza-bridged-bicyclic compounds of the present invention. Relative to the above generic description, certain compounds having Formula (I) are preferred.

The preferred embodiments of the aza-bridged-bicyclic compounds of the present invention include those compounds wherein the phenyl group of the phenylalanine amino acid is substituted on the para position with $R_6$. Further disclosed herein are experimental results demonstrating that the activity of certain aza-bridged-bicyclic compounds of the present invention as $\alpha_4\beta_1$ and $\alpha_4\beta_7$ integrin receptor antagonists decreases significantly when the phenyl group of the phenylalanine amino acid is substituted on the meta position with $R_6$.

Preferred embodiments of the instant compounds also include those aza-bridged-bicyclic compounds wherein $R_6$ is benzofused heterocyclyl, aryl, arylamido, heteroarylamido, ureido (wherein the terminal amino is dialkyl substituted), aminocarbonyloxy (wherein amino is dialkyl substituted) and aryl($C_{1-8}$)alkoxy. Experimental results seem to demonstrate that the activity of certain compounds as $\alpha_4\beta_1$ and $\alpha_4\beta_7$ integrin receptor antagonists increases significantly when the aryl and heteroaryl portion of $R_6$ is further mono- or di-substituted at the ortho position.

In addition to the above discoveries relative to the structure of the compounds of the present invention, we have experimentally determined that the stereochemistry significantly affects the $\alpha_4\beta_1$ and $\alpha_4\beta_7$ integrin receptor antagonist activity of certain compounds. In addition to racemic mixtures demonstrating activity as $\alpha_4\beta_1$ and $\alpha_4\beta_7$ integrin receptor antagonists, experimental results have shown that individual diastereomers each have either a significantly increased or significantly decreased activity as an $\alpha_4\beta_1$ and $\alpha_4\beta_7$ integrin receptor antagonist.

For example, Table I compares the $\alpha_4\beta_1$ and $\alpha_4\beta_7$ integrin receptor antagonist activity as a value of $IC_{50}$ for the racemic mixtures and resolved (S,S) and (R,S) diasteromers.

TABLE I

| Antagonist $IC_{50}$ Activity (nM) | | | | | | | | |
|---|---|---|---|---|---|---|---|---|
| Racemic Mixture | | | (S,S) diasteromer | | | (R,S) diasteromer | | |
| | Activity | | | Activity | | | Activity | |
| Cpd | $\alpha_4\beta_1$ | $\alpha_4\beta_7$ | Cpd | $\alpha_4\beta_1$ | $\alpha_4\beta_7$ | Cpd | $\alpha_4\beta_1$ | $\alpha_4\beta_7$ |
| | | | 5a | 81 | 62 | 5b | 394 | 3380 |
| 6 | 20 | 283 | 6a | 23 | 217 | 6b | 222 | 421 |
| | | | 16a | 153 | 2090 | 16b | 240 | 393 |
| 18 | 124 | 210 | 18a | 857 | 9000 | | | |
| | | | 19a | 300 | 3822 | 19b | 1210 | 3220 |
| 47 | 74 | 83 | 47a | 26 | 102 | | | |
| 52 | 124 | 998 | 52a | 45 | 436 | | | |
| 53 | 179 | 871 | 53a | 219 | 693 | | | |
| 71 | 9 | 30 | 71a | 6 | 33 | | | |

Although the racemic mixtures have significant activity compared to the resolved diastereomers, the (S,S) diastereomers appear to generally have higher activity than the (R,S) diastereomers. The scope of the present invention is intended to encompass all racemic mixtures, enantiomers and diastereomers including, but not limited to, (R/S,S), (R/S,R), (S,R/S), (R,R/S), (S,S), (R,S), (S,R) and (R,R) diastereomers and enantiomers of the compounds of the present invention without limitation.

Preferred embodiments are those aza-bridged-bicyclic compounds wherein Y is selected from the group consisting of —C(O)— and —$SO_2$—. More preferably, Y is selected from —$SO_2$—.

Preferred embodiments include those compounds wherein $R_1$ is selected from $R_7$. $R_7$ is preferably selected from the group consisting of aryl and heteroaryl optionally substituted with one to five substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, aryl, heteroaryl, arylcarbonyl, heteroarylcarbonyl, arylsulfonyl, amino, N—($C_{1-8}$akyl)amino, N,N—($C_{1-8}$dialkyl)amino, —$CF_3$ and —$OCF_3$; and, wherein the aryl and heteroaryl substituents and the aryl portion of the arylcarbonyl substituent are optionally substituted with one to five substituents independently selected from the group consisting of halogen, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$. Most preferred embodiments include those compounds wherein $R_7$ is selected from the group consisting of tolyl, phenyl and thienyl.

Preferred embodiments include those compounds wherein $R_2$, $R_3$, $R_4$ and $R_5$ are independently selected from the group consisting of hydrogen and $C_{1-4}$alkyl. More preferably, $R_2$, $R_3$, $R_4$ and $R_5$ are independently selected from the group consisting of hydrogen and methyl.

Preferred embodiments include those compounds wherein $R_6$ is optionally present and is one to three substituents independently selected from the group consisting of halogen, $C_{1-8}$alkoxy, $R_{10}$, $R_{12}$, —$N(R_{11})C(O)$—$R_{10}$, —$N(R_{11})C(O)$—$R_{12}$, —$N(R_{11})SO_2$—$R_{10}$, —$N(R_{11})C(O)$—$N(R_{11}, R_{12})$, —$N(R_{11})C(O)$—$N(R_{12}, R_{17})$, —$OC(O)$—$N(R_{11}, R_{12})$, —$OC(O)$—$N(R_{12}, R_{17})$, —$OC(O)$—$R_{10}$ and $R_{10}$—($C_{1-8}$)alkoxy. More preferably, $R_6$ is optionally present and is one to three substituents independently selected from the group consisting of halogen, $C_{1-4}$alkoxy, $R_{10}$, $R_{12}$, —$N(R_{11})C(O)$—$R_{10}$, —$N(R_{11})C(O)$—$R_{12}$, —$N(R_{11})SO_2$—$R_{10}$, —$N(R_{11})C(O)$—$N(R_{11}, R_{12})$, —$N(R_{11})C(O)$—$N(R_{12}, R_{17})$, —$OC(O)$—$N(R_{11}, R_{12})$, —$OC(O)$—$N(R_{12}, R_{17})$, —$OC(O)$—$R_{10}$ and $R_{10}$—($C_{1-4}$) alkoxy. Most preferably, $R_6$ is one substituent selected from the group consisting of $R_{10}$, —$N(R_{11})C(O)$—$R_{10}$, —$N(R_{11})C(O)$—$N(R_{11}, R_{12})$, —$N(R_{11})C(O)$—$N(R_{12}, R_{17})$, —$OC(O)$—$N(R_{11}, R_{12})$, —$OC(O)$—$N(R_{12}, R_{17})$, —$OC(O)$—$R_{10}$ and $R_{10}$-methoxy.

Preferred embodiments include those compounds wherein $R_{10}$, is selected from the group consisting of cycloalkyl, heterocyclyl, aryl and heteroaryl optionally substituted with one to five substituents independently selected from the group consisting of halogen, $C_{1-8}$alkyl, $C_{1-8}$alkoxy, $C_{1-8}$alkoxycarbonyl, carboxyl, arylcarbonyl, arylsulfonyl, —$CF_3$ and —$OCF_3$; wherein cycloalkyl and heterocyclyl are optionally substituted with one to three oxo substituents; and, wherein the aryl portion of the arylcarbonyl substituent is optionally substituted with one to five substituents independently selected from $C_{1-8}$alkoxy.

More preferably $R_{10}$ is selected from the group consisting of cycloalkyl, heterocyclyl, aryl and heteroaryl optionally substituted with one to five substituents independently selected from the group consisting of halogen, $C_{1-4}$alkyl, $C_{1-4}$alkoxy, $C_{1-4}$alkoxycarbonyl, carboxyl, arylcarbonyl, arylsulfonyl, —$CF_3$ and —$OCF_3$; wherein cycloalkyl and heterocyclyl are optionally substituted with one to three oxo substituents; and, wherein the aryl portion of the arylcarbonyl substituent is optionally substituted with one to five substituents independently selected from $C_{1-4}$alkoxy.

Most preferably $R_{10}$ is selected from the group consisting of cyclopropyl, 1,3-dihydro-2H-isoindolyl, 2-azabicyclo[2.2.2]octyl, piperidinyl, morpholinyl, phenyl, naphthalenyl, thienyl, 1H-pyrrolyl and pyridinyl; wherein cyclopropyl, piperidinyl, morpholinyl, phenyl, naphthalenyl, thienyl, 1H-pyrrolyl and pyridinyl are optionally substituted with one to four substituents independently selected from the group consisting of chlorine, fluorine, bromine, methyl, isopropyl, t-butyl, methoxy, t-butoxycarbonyl, carboxyl, phenylcarbonyl (wherein the phenyl portion of phenylcarbonyl is optionally substituted with one to two substituents selected from methoxy), —$CF_3$ and —$OCF_3$; wherein 1,3-dihydro-2H-isoindolyl is optionally substituted with oxo; and, wherein 2-azabicyclo[2.2.2]octyl is optionally substituted with phenylsulfonyl.

Preferred embodiments include those compounds wherein $R_{12}$ is selected from the group consisting of $C_{1-8}$alkyl and $C_{2-8}$alkynyl optionally substituted on a terminal carbon with $R_{14}$. More preferably, $R_{12}$ is selected from the group consisting of $C_{1-4}$alkyl and $C_{2-4}$alkynyl optionally substituted on a terminal carbon with $R_{14}$. Most preferably, $R_{12}$ is selected from the group consisting of t-butyl and ethynyl; wherein ethynyl is optionally substituted on a terminal carbon with a substituent $R_{14}$. Preferred embodiments include those compounds wherein $R_{14}$ is preferably aryl optionally substituted with one to five substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, aryl, heteroaryl, arylcarbonyl, heteroarylcarbonyl, arylsulfonyl, amino, N—($C_{1-8}$alkyl)amino, N,N—($C_{1-8}$dialkyl)amino, —$CF_3$ and —$OCF_3$; and, wherein the aryl and heteroaryl substituents and the aryl portion of the arylcarbonyl substituent are optionally substituted with one to five substituents independently selected from the group consisting of halogen, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl) amino, —$CF_3$ and —$OCF_3$. Most preferably $R_{14}$ is most preferably is selected from the group consisting of phenyl and $C_{1-8}$alkylphenyl.

Preferred embodiments include those compounds wherein $R_{11}$ is selected from the group consisting of hydrogen and $C_{1-4}$alkyl. More preferably, $R_{11}$ is hydrogen.

Preferred embodiments include those compounds wherein A is selected from the group consisting of methylene and ethylene. Most preferably A is methylene.

Preferred embodiments include those compounds wherein $B_1$ and $B_2$ are independently selected from the group consisting of $C_{1-4}$alkylene and $C_{2-4}$alkenylene optionally substituted with one to two substituents independently selected from the group consisting of halogen, hydroxy, hydroxy($C_{1-4}$)alkyl, hydroxy($C_{1-4}$)alkoxy, $C_{1-4}$alkyl, $C_{2-4}$alkenyl, $C_{2-4}$alkynyl, $C_{1-4}$alkoxy, carboxyl, amino, N—($C_{1-4}$alkyl)amino, N,N—($C_{1-4}$dialkyl)amino, —$CF_3$ and —$OCF_3$.

More preferably, $B_1$ and $B_2$ are independently selected from the group consisting of —$CH_2$—, —$(CH_2)_2$— and —$(CH)_2$— optionally substituted with one to two substituents independently selected from the group consisting of halogen, hydroxy, hydroxy($C_{1-4}$)alkyl, hydroxy($C_{1-4}$) alkoxy, $C_{1-4}$alkyl, $C_{2-4}$alkenyl, $C_{2-4}$alkynyl, $C_{1-4}$alkoxy, carboxyl, amino, N—($C_{1-4}$alkyl)amino, N,N—($C_{1-4}$dialkyl) amino, —$CF_3$ and —$OCF_3$. Also more preferably, $B_1$ is selected from the group consisting of —$CH_2$—, —$(CH_2)_2$— and —$(CH)_2$— optionally substituted with one to two substituents independently selected from the group consisting of halogen, hydroxy, hydroxy($C_{1-4}$)alkyl, hydroxy($C_{1-4}$) alkoxy, $C_{1-4}$alkyl, $C_{2-4}$alkenyl, $C_{2-4}$alkynyl, $C_{1-4}$alkoxy, carboxyl, amino, N—($C_{1-4}$alkyl)amino, N,N—($C_{1-4}$dialkyl) amino, —$CF_3$ and —$OCF_3$ and that $B_2$ is selected from —$(CH_2)_2$—. Most preferably, $B_1$ is selected from the group consisting of —$CH_2$—, —$(CH_2)_2$— and —$(CH)_2$—.

Embodiments of the aza-bridged-bicyclic amino acid compounds of the present invention include those compounds of Formula (I) shown in Table II of the formula:

TABLE II

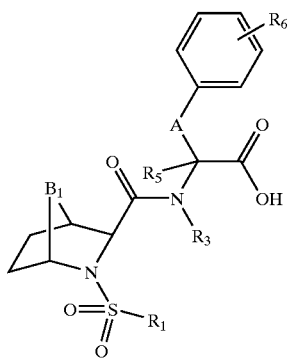

wherein $B_1$, $R_1$, $R_3$, $R_5$, A and $R_6$ are dependently selected from the group consisting of:

| Cpd | $B_1$ | $R_1$ | $R_3$ | $R_5$ | A | $R_6$ |
|---|---|---|---|---|---|---|
| 1 | $(CH_2)_2$ | 4-Tol | H | H | $CH_2$ | 4-NHC(O)-(2,6-$Cl_2$)Ph |
| 2 | $(CH_2)_2$ | 4-Tol | H | H | $CH_2$ | 4-NHC(O)-(2,4,6-$Cl_3$)Ph |
| 3 | $(CH_2)_2$ | 4-Tol | H | H | $CH_2$ | 4-NHC(O)-[2,6-$(OMe)_2$]Ph |
| 5a/5b | $CH_2$ | Ph | H | H | $CH_2$ | 4-NHC(O)-(2,6-$F_2$)Ph |
| 6/6a/6b | $(CH_2)_2$ | Ph | H | H | $CH_2$ | 4-NHC(O)-(2,6-$Cl_2$)Ph |
| 8 | $(CH_2)_2$ | Ph | H | H | $CH_2$ | 4-[2,6-$(OMe)_2$]Ph |
| 9 | $(CH_2)_2$ | 4-Tol | H | H | $CH_2$ | 4-NHC(O)-(2-Me)Ph |
| 10 | $(CH_2)_2$ | 4-Tol | H | H | $CH_2$ | 4-NHC(O)-(2-Cl)Ph |
| 11 | $(CH_2)_2$ | 4-Tol | H | H | $CH_2$ | 4-NHC(O)-(2,6-$F_2$)Ph |
| 12 | $(CH_2)_2$ | 4-Tol | H | H | $CH_2$ | 4-NHC(O)-(2-$CF_3$)Ph |
| 13 | $(CH_2)_2$ | 4-Tol | H | H | $CH_2$ | 4-NHC(O)-(2-$OCF_3$)Ph |
| 14 | $(CH_2)_2$ | 4-Tol | H | H | $CH_2$ | 4-NHC(O)-(2-Br)Ph |
| 15 | $(CH_2)_2$ | Ph | H | H | $CH_2$ | 4-NHC(O)-(2,6-$F_2$)Ph |
| 16a/16b | $CH_2$ | Ph | H | H | $CH_2$ | 4-NHC(O)-(2,6-$Cl_2$)Ph |
| 18/18a | $(CH_2)_2$ | 4-Tol | H | H | $CH_2$ | 4-[2,6-$(OMe)_2$]Ph |
| 19a/19b | $CH_2$ | Ph | H | H | $CH_2$ | 4-NHC(O)-[2,6-$(OMe)_2$]Ph |
| 23 | $(CH_2)_2$ | 4-Tol | H | H | $CH_2$ | 4-CC-(4-t-butyl)Ph |
| 24 | $(CH_2)_2$ | 4-Tol | H | H | $CH_2$ | 4-CC—Ph |
| 25 | $(CH_2)_2$ | 4-Tol | H | H | $CH_2$ | 4-NHC(O)—Ph |
| 26 | $(CH_2)_2$ | 4-Tol | H | H | $CH_2$ | 4-NHC(O)-[4-C(O)-[2,5-$(OMe)_2$]Ph]Ph |
| 27 | $(CH_2)_2$ | 4-Tol | H | H | $CH_2$ | 4-NHC(O)—$CH_{2-(2,6-Cl2)}$Ph |
| 28 | $(CH_2)_2$ | Ph | H | H | $CH_2$ | 4-NHC(O)—NH-(2,6-$Cl_2$)Ph |
| 29 | $(CH_2)_2$ | Ph | H | H | $CH_2$ | 4-$OCH_2$-(2,6-$Cl_2$)Ph |
| 30 | $(CH_2)_2$ | 4-Tol | H | H | $CH_2$ | 4-$OCH_2$—Ph |
| 31 | $(CH_2)_2$ | 4-Tol | H | H | $CH_2$ | 4-NHC(O)-(2,4,6-isopropyl$_3$)Ph |
| 32 | $(CH_2)_2$ | 4-Tol | H | H | $CH_2$ | 4-(1H-pyrrol-1-yl) |
| 33 | $(CH_2)_2$ | 4-Tol | H | H | $CH_2$ | 4-Ph |
| 34 | $(CH_2)_2$ | Ph | H | H | $CH_2$ | 4-NHC(O)—NH-(2,6-$F_2$)Ph |
| 35 | $(CH_2)_2$ | 4-Tol | H | H | $CH_2$ | 3-NHC(O)-(2,6-$F_2$)Ph |
| 36 | $(CH_2)_2$ | 4-Tol | H | H | $CH_2$ | 3-NHC(O)-[2,6-$(OMe)_2$]Ph |
| 37 | $(CH_2)_2$ | 4-Tol | H | H | $CH_2$ | 3-NHC(O)-(2,6-$Cl_2$)Ph |
| 38 | $(CH_2)_2$ | Ph | H | $CH_3$ | $CH_2$ | 4-$OCH_2$-(2,6-$Cl_2$)Ph |
| 39 | $(CH_2)_2$ | Ph | $CH_3$ | H | $CH_2$ | 4-NHC(O)-(2,6-$Cl_2$)Ph |
| 40 | $(CH)_2$ | Ph | H | H | $CH_2$ | 4-$OCH_2$-(2,6-$Cl_2$)Ph |
| 41 | $(CH_2)_2$ | Ph | H | H | $CH_2$ | 4-$OCH_2$-(2,6-$Cl_2$)Ph |
| 42 | $(CH)_2$ | Ph | H | H | $CH_2$ | 4-NHC(O)-(2,6-$Cl_2$)Ph |
| 43 | $(CH_2)_2$ | Ph | H | H | $CH_2$ | 4-(2,4,6-$F_3$)Ph |
| 44 | $(CH_2)_2$ | Ph | H | H | $CH_2$ | 4-(2,3,5,6-$F_4$)Ph |
| 45 | $(CH_2)_2$ | Ph | H | H | $CH_2$ | 4-O-t-butoxy |
| 46 | $(CH_2)_2$ | Ph | H | H | $(CH_2)_2$ | — |
| 47/47a | $(CH_2)_2$ | Ph | H | H | $CH_2$ | 4-(1,3-dihydro-1,3-dioxo-2H-isoindol-2-yl) |
| 48 | $(CH_2)_2$ | Ph | H | H | $CH_2$ | 4-NHC(O)-(2-$CO_2$H)Ph |
| 49 | $(CH_2)_2$ | Ph | H | H | $CH_2$ | 4-(2,5-diMe-1H-pyrrol-1-yl) |
| 50/50a | $(CH_2)_2$ | Ph | H | H | $CH_2$ | 4-NHC(O)-4-pyridinyl |
| 51 | $(CH_2)_2$ | Ph | H | H | $CH_2$ | 4-NHS$O_2$-(2,6-$Cl_2$)Ph |
| 52/52a | $(CH_2)_2$ | Ph | H | H | $CH_2$ | 4-OC(O)—N$(CH_3)_2$ |
| 53/53a | $(CH_2)_2$ | Ph | H | H | $CH_2$ | 4-NHC(O)-(1-t-butoxycarbonyl)4-piperidinyl |
| 54 | $(CH_2)_2$ | 4-FPh | H | H | $CH_2$ | 4-NHC(O)-(2,6-$Cl_2$)Ph |
| 55 | $(CH_2)_2$ | 4-FPh | H | H | $CH_2$ | 4-NHC(O)-[2,6-$(OMe)_2$]Ph |
| 56 | $(CH_2)_2$ | Ph | H | H | $CH_2$ | 4-OC(O)-4-morpholinyl |
| 57 | $(CH_2)_2$ | Ph | H | H | $CH_2$ | 4-OC(O)N(iso-propyl)$_2$ |
| 58 | $(CH_2)_2$ | Ph | H | H | $CH_2$ | 4-t-butyl |
| 59 | $(CH_2)_2$ | Ph | H | H | $CH_2$ | 4-NHC(O)-4-piperidinyl |

TABLE II-continued

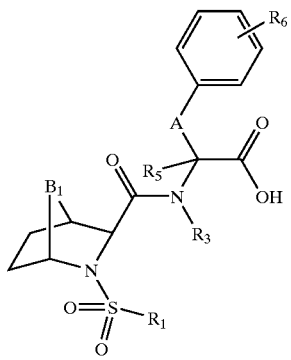

wherein $B_1$, $R_1$, $R_3$, $R_5$, A and $R_6$ are dependently selected from the group consisting of:

| Cpd | $B_1$ | $R_1$ | $R_3$ | $R_5$ | A | $R_6$ |
|---|---|---|---|---|---|---|
| 60 | $(CH_2)_2$ | Ph | H | H | $CH_2$ | 4-NHC(O)-(3,5-$Cl_2$)4-pyridinyl |
| 61 | $(CH_2)_2$ | Ph | H | H | $CH_2$ | 4-NHC(O)—$NMe_2$ |
| 62a–62d | $(CH_2)_2$ | Ph | H | H | $CH_2$ | 3-F-4-[$OCH_2$(2,6-$Cl_2$)Ph] |
| 63 | $(CH_2)_2$ | 2-Thi | H | H | $CH_2$ | 4-OC(O)—$NMe_2$ |
| 64 | $(CH_2)_2$ | Ph | H | H | $CH_2$ | 4-NHC(O)—t-butyl |
| 65 | $(CH_2)_2$ | Ph | H | H | $CH_2$ | 4-NHC(O)-(2-OMe)1-naphthalenyl |
| 66 | $(CH_2)_2$ | 2-Thi | H | H | $CH_2$ | 4-NHC(O)-(2,6-$Cl_2$)Ph |
| 67 | $(CH_2)_2$ | Ph | H | H | $CH_2$ | 4-NHC(O)—cyclopropyl |
| 68 | $(CH_2)_2$ | Ph | H | H | $CH_2$ | 4-NHC(O)-(2,2,3,3-$Me_4$)cyclopropyl |
| 69 | $(CH_2)_2$ | Ph | H | H | $CH_2$ | 4-NHC(O)—iso-propyl |
| 70 | $(CH_2)_2$ | Ph | H | H | $CH_2$ | 4-NHC(O)-(2-$SO_2$Ph)-2-azabicyclo[2.2.2]oct-3-yl |
| 71/71a | $(CH_2)_2$ | 2-Thi | H | H | $CH_2$ | 4-NHC(O)-(3,5-$Cl_2$)4-pyridinyl |
| 72 | $(CH_2)_2$ | Ph | H | H | $CH_2$ | 4-NHC(O)-(2-Me)cyclopropyl |
| 73 | $(CH_2)_2$ | Ph | H | H | $CH_2$ | 4-(2,6-diMe)Ph |
| 74 | $(CH_2)_2$ | Ph | H | H | $CH_2$ | 4-(2,6-$Cl_2$)Ph |
| 75 | $(CH_2)_2$ | 2-Thi | H | H | $CH_2$ | 4-(2,6-$Cl_2$)Ph |
| 76 | $(CH_2)_2$ | 2-Thi | H | H | $CH_2$ | 4-(2,6-diMe)Ph |
| 77 | $(CH_2)_2$ | 2-Thi | H | H | $CH_2$ | 4-[2,6-$(OMe)_2$]Ph |
| 78 | $(CH_2)_2$ | 2-Thi | H | H | $CH_2$ | 4-(4-fluoro-1,3-dihydro-1,3-dioxo-2H—isoindol-2-yl) |
| 79 | $(CH_2)_2$ | 2-Thi | H | H | $CH_2$ | 4-NHC(O)—$NMe_2$ |
| 80 | $(CH_2)_2$ | 2-Thi | H | H | $CH_2$ | 4-OC(O)—$NMe_2$ |
| 81 | $(CH_2)_2$ | 2-Thi | H | H | $CH_2$ | 4-OC(O)-(4-morpholinyl) |
| 82 | $(CH_2)_2$ | 2-Thi | H | H | $CH_2$ | 4-OC(O)-(4-Me-1-piperazinyl) |
| 83 | $(CH_2)_2$ | Ph | H | H | $CH_2$ | 4-OC(O)-(4-Me-1-piperazinyl) |
| 84 | $(CH_2)_2$ | Ph | H | H | $CH_2$ | 4-N(Me)C(O)-(2,6-$Cl_2$)Ph |
| 85 | $(CH_2)_2$ | Ph | H | H | $CH_2$ | 4-N(Me)C(O)-(3,5-$Cl_2$)4-pyridinyl |
| 86 | $(CH_2)_2$ | 2-Thi | H | H | $CH_2$ | 4-N(Me)C(O)-(3,5-$Cl_2$)4-pyridinyl |
| 87 | $(CH_2)_2$ | 2-Thi | H | H | $CH_2$ | 4-N(Me)C(O)-(2,6-$Cl_2$)Ph |
| 88 | $(CH_2)_2$ | 2-Thi | H | H | $CH_2$ | 4-$OCH_2$-(2,6-$Cl_2$)Ph |
| 89 | $(CH_2)_2$ | 2-Thi | H | H | $CH_2$ | 4-(1,3-dihydro-1,3-dioxo-2H-isoindol-2-yl) |
| 90 | $(CH_2)_2$ | Ph | H | H | $CH_2$ | 4-(1,3-dihydro-4,7-dimethyl-1,3-dioxo-2H—isoindol-2-yl) |
| 91 | $(CH_2)_2$ | 2-Thi | H | H | $CH_2$ | 4-(1,3-dihydro-4,7-dimethyl-1,3-dioxo-2H—isoindol-2-yl) |
| 92 | $CH_2$ | 2-Thi | H | H | $CH_2$ | 4-NHC(O)-(3,5-$Cl_2$)4-pyridinyl |
| 93 | $CH_2$ | 2-Thi | H | H | $CH_2$ | 4-NHC(O)-(2,6-$Cl_2$)Ph |
| 94 | $(CH_2)_2$ | Ph | H | H | $CH_2$ | 4-(1,1-dioxido-3-oxo-1,2-benzisothiazol-2(3H)-yl) |
| 95 | $(CH_2)_2$ | Ph | H | H | $CH_2$ | 4-(4-chloro-1,3-dihydro-1,3-dioxo-2H—isoindol-2-yl) |
| and, | | | | | | |
| 96 | $(CH_2)_2$ | Ph | H | H | $CH_2$ | 4-(7,9-dioxo-8-azaspiro[4.5]dec-8-yl) | and pharmaceutically acceptable salts, racemic mixtures, diastereomers and enantiomers thereof.

An embodiment of the present invention is a process for preparing an intermediate compound of Formula (III)

Formula (III)

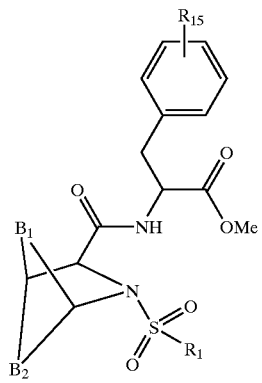

wherein $R_1$ is selected from the group consisting of $R_7$ and $R_8$;

$R_7$, $R_{10}$ and $R_{14}$ are independently selected from the group consisting of cycloalkyl, heterocyclyl, aryl and heteroaryl optionally substituted with one to five substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, aryl, heteroaryl, arylcarbonyl, heteroarylcarbonyl, arylsulfonyl, amino, N—($C_{1-8}$alkyl)amino, N,N—($C_{1-8}$dialkyl)amino, —$CF_3$ and —$OCF_3$; wherein cycloalkyl and heterocyclyl are optionally substituted with one to three substituents independently selected from oxo; and, wherein the aryl and heteroaryl substituents and the aryl portion of the arylcarbonyl substituent are optionally substituted with one to five substituents independently selected from the group consisting of halogen, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$;

$R_8$, $R_{12}$ and $R_{17}$ are independently selected from the group consisting of $C_{1-8}$alkyl, $C_{2-8}$alkenyl, $C_{2-8}$alkynyl, and (halo)$_{1-3}$($C_{1-8}$)alkyl; wherein $C_{1-8}$alkyl, $C_{2-8}$alkenyl and $C_{2-8}$alkynyl are optionally substituted on a terminal carbon with one to three substituents independently selected from $R_{14}$;

$R_{15}$ is selected from the group consisting of hydroxy, amino, $NO_2$ and $R_6$;

$R_6$ is optionally present and is one to three substituents independently selected from the group consisting of halogen, $C_{1-8}$alkoxy, $R_{10}$, $R_{12}$, —N($R_{11}$)C(O)—$R_{10}$, —N($R_{11}$)C(O)—$R_{12}$, —N($R_{11}$)SO$_2$—$R_{10}$, —N($R_{11}$)SO$_2$—$R_{12}$, —N($R_{11}$)C(O)—N($R_{11}$, $R_{10}$), —N($R_{11}$)C(O)—N($R_{11}$, $R_{12}$), —N($R_{11}$)C(O)—N($R_{12}$, $R_{17}$), —C(O)—N($R_{11}$, $R_{10}$), —C(O)—N($R_{11}$, $R_{12}$), —C(O)—N($R_{12}$, $R_{17}$), —OC(O)—N($R_{11}$, $R_{10}$), —OC(O)—N($R_{11}$, $R_{12}$), —OC(O)—N($R_{12}$, $R_{17}$), —OC(O)—$R_{10}$, —OC(O)—$R_{12}$, —O—$R_{10}$ and $R_{10}$—($C_{1-8}$)alkoxy;

$R_{11}$ is selected from the group consisting of hydrogen and $C_{1-8}$alkyl; and, $B_1$ and $B_2$ are independently selected from the group consisting of $C_{1-8}$alkylene and $C_{2-8}$alkenylene optionally substituted with one to two substituents independently selected from the group consisting of halogen, hydroxy, hydroxy($C_{1-8}$)alkyl, hydroxy($C_{1-8}$)alkoxy, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$;

and pharmaceutically acceptable salts, racemic mixtures, diastereomers and enantiomers thereof;

comprising reacting a compound of Formula (IV)

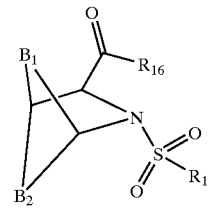

Formula (IV)

wherein $R_{16}$ is selected from the group consisting of halogen, mixed anhydride and hydroxy;

with a compound of Formula (V)

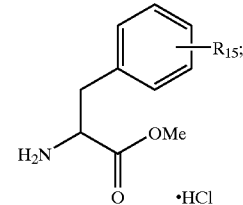

Formula (V)

in the presence of appropriate coupling agents, bases and solvents to form the compound of Formula (II).

In a preferred embodiment of the process of the present invention, $R_{15}$ is a substituent selected from the group consisting of hydroxy, iodine, bromine and $NO_2$.

Other preferred embodiments include compounds of Formula (I) selected from compounds of the formula:

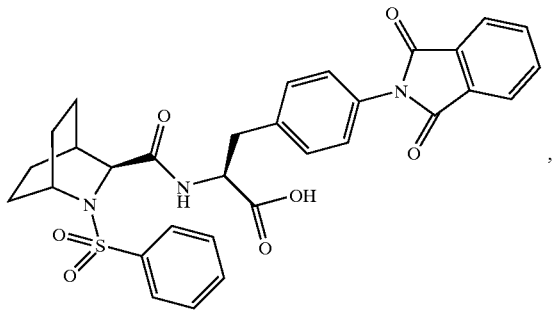

,

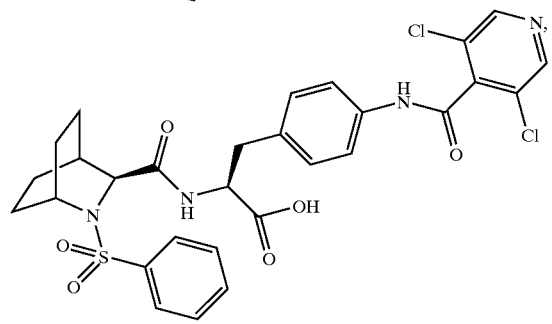

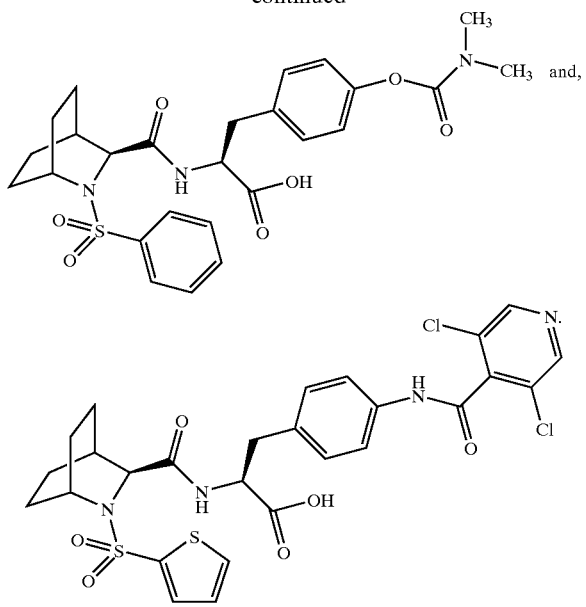

The compounds of the present invention may also be present in the form of pharmaceutically acceptable salts. For use in medicine, the salts of the compounds of this invention refer to nonboxic "pharmaceutically acceptable salts" (*Ref. International J. Pharm.*, 1986, 33, 201–217; *J. Pharm.Sci.*, 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diasteromers by standard techniques, such as the formation of stereoisomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, "alkyl" and "alkoxy" whether used alone or as part of a substituent group refers to straight and branched carbon chains having 1 to 8 carbon atoms or any number within this range. Similarly, alkenyl and alkynyl groups include straight and branched chain alkenes and alkynes having 2 to 8 carbon atoms or any number within this range, wherein an alkenyl chain has at least one double bond in the chain and an alkynyl chain has at least one triple bond in the chain. Alkoxy radicals are oxygen ethers formed from the previously described straight or branched chain alkyl groups.

As used herein, unless otherwise noted "oxo" whether used alone or as part of a substituent group refers to an O= to either a carbon or a sulfur atom. For example, phthalimide and saccharin are examples of compounds with oxo substituents.

The term "cycloalkyl," as used herein, refers to an optionally substituted, stable, saturated or partially saturated monocyclic or bicyclic ring system containing from 3 to 8 ring carbons and preferably 5 to 7 ring carbons. Examples of such cyclic alkyl rings include cyclopropyl, cyclobutyl, cyclopentyl, cyclohexyl or cycloheptyl.

The term "heterocyclyl" as used herein refers to an optionally substituted, stable, saturated or partially saturated 5 or 6 membered monocyclic or bicyclic ring systems which consists of carbon atoms and from one to three heteroatoms selected from N, O or S. Examples of heterocyclyl groups include, but are not limited to, pyrrolinyl (including 2H-pyrrole, 2-pyrrolinyl or 3-pyrrolinyl), pyrrolidinyl, dioxolanyl, 2-imidazolinyl, imidazolidinyl, 2-pyrazolinyl, pyrazolidinyl, piperidinyl, dioxanyl, morpholinyl, dithianyl, thiomorpholinyl or piperazinyl. The heterocyclyl group may be attached at any heteroatom or carbon atom which results in the creation of a stable structure.

The term "aryl", as used herein, refers to optionally substituted aromatic groups comprising a stable six membered monocyclic or ten membered bicyclic aromatic ring system which consists of carbon atoms. Examples of aryl groups include, but are not limited to, phenyl or naphthalenyl.

The term "heteroaryl" as used herein represents a stable five or six membered monocyclic aromatic ring system or a nine or ten membered benzo-fused heteroaromatic ring system which consists of carbon atoms and from one to three heteroatoms selected from N, O or S. The heteroaryl group may be attached at any heteroatom or carbon atom which results in the creation of a stable structure.

The term "arylalkyl" means an alkyl group substituted with an aryl group (e.g., benzyl, phenethyl). The term "arylalkoxy" indicates an alkoxy group substituted with an aryl group (e.g., benzyloxy, phenethoxy, etc.). Similarly, the term "aryloxy" indicates an oxy group substituted with an aryl group (e.g., phenoxy).

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The aza-bridged-bicyclic amino acid compounds of the present invention are useful α4 integrin receptor antagonists and, more particularly, α4β1 and α4β7 integrin receptor antagonists for treating a variety of integrin mediated disorders that are ameliorated by inhibition of the α4β1 and α4β7 integrin receptor including, but not limited to, inflammatory, autoimmune and cell-proliferative disorders.

Illustrative of the invention is a pharmaceutical composition comprising a pharmaceutically acceptable carrier and any of the compounds described above. Also illustrative of the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier. The present invention also provides pharmaceutical compositions comprising one or more compounds of this invention in association with a pharmaceutically acceptable carrier.

An example of the invention is a method for the treatment of integrin mediated disorders in a subject in need thereof comprising administering to the subject a therapeutically effective amount of any of the compounds or pharmaceutical compositions described above. Also included in the invention is the use of a compound of Formula (I) for the preparation of a medicament for treating an integrin mediated disorder in a subject in need thereof.

Further exemplifying the invention is the method for the treatment of integrin mediated disorders, wherein the therapeutically effective amount of the compound is from about 0.01 mg/kg/day to about 30 mg/kg/day.

In accordance with the methods of the present invention, the individual components of the pharmaceutical compositions described herein can be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The utility of the compounds to treat integrin mediated disorders can be determined according to the procedures herein. The present invention therefore provides a method for the treatment of integrin mediated disorders in a subject in need thereof which comprises administering any of the compounds as defined herein in a quantity effective to inhibit the α4β1 and α4β7 integrin receptor including, but not limited to, inflammatory, autoimmune and cell-proliferative disorders. Accordingly, a compound of the present invention may be administered by any conventional route of administration including, but not limited to oral, nasal, pulmonary, sublingual, ocular, transdermal, rectal, vaginal and parenteral (i.e. subcutaneous, intramuscular, intradermal, intravenous etc.).

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients,* published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded,* Volumes 1–3, edited by Lieberman et al; *Pharmaceutical Dosage Forms: Parenteral Medications,* Volumes 1–2, edited by Avis et al; and *Pharmaceutical Dosage Forms: Disperse Systems,* Volumes 1–2, edited by Lieberman et al; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, dry powders for reconstitution or inhalation, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg/kg to about 300 mg/kg (preferably from about 0.01 mg/kg to about 100 mg/kg; and, more preferably, from about 0.01 mg/kg to about 30 mg/kg) and may be given at a dosage of from about 0.01 mg/kg/day to about 300 mg/kg/day (preferably from about 0.01 mg/kg/day to about 100 mg/kg/day and more preferably from about 0.01 mg/kg/day to about 30 mg/kg/day). Preferably, the method for the treatment of integrin mediated disorders described in the present invention using any of the compounds as defined herein, the dosage form will contain a pharmaceutically acceptable carrier containing between from about 0.01 mg to about 100 mg; and, more preferably, from about 5 mg to about 50 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxyethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treatment of integrin mediated disorders is required for a subject in need thereof.

The daily dose of a pharmaceutical composition of the present invention may be varied over a wide range from about 0.7 mg to about 21,000 mg per adult human per day; preferably, the dose will be in the range of from about 0.7 mg to about 7000 mg per adult human per day; most preferably the dose will be in the range of from about 0.7 mg to about 2100 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg to about 300 mg/kg of body weight per day. Preferably, the range is from about 0.01 mg/kg to about 100 mg/kg of body weight per day; and, most preferably, from about 0.01 mg/kg to about 30 mg/kg of body weight per day. Advantageously, a compound of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:

| | |
|---|---|
| BSA | Bovine Serum Albumen |
| DBC | 2,6-Dichlorobenzoylchloride |
| DCM | Dichloromethane |
| DIEA | Diisopropylethylamine |
| DMF | N,N-Dimethylformamide |
| EDAC | N-ethyl-N'-dimethylaminopropylcarbodiimide hydrochloride |
| Et$_2$O | Diethyl ether |
| EtOAc | Ethyl acetate |
| EtOH | Ethanol |
| h | hour |
| HATU | O-(7-azabenzotriazol-1-yl)-1,1,3,3-tetramethyluronium hexafluorophosphate |
| HPLC | High Performance Liquid Chromatography |
| Me | Methyl |
| MeOH | Methanol |
| min | Minutes |
| PBS | Phosphate Buffer Solution |
| Ph | Phenyl |
| rt | Room temperature |
| SDS | Sodium Dodecasulfate |
| THF | Tetrahydrofuran |
| Thi | Thienyl |
| TMS | Tetramethylsilane |
| TFA | Trifluoroacetic acid |
| Tol | Toluene |

General Synthetic Methods

Representative compounds of the present invention can be synthesized in accordance with the general synthetic methods described below and are illustrated more particularly in the scheme that follows. Since the scheme is an illustration, the invention should not be construed as being limited by the chemical reactions and conditions expressed. The preparation of the various starting materials used in the schemes is well within the skill of persons versed in the art.

Scheme AA describes a general synthetic method whereby intermediate and target compounds of the present invention may be prepared. Additional representative compounds and stereoisomers, racemic mixtures, diastereomers and enantiomers thereof can be synthesized using the intermediates prepared in accordance with the Schemes AA and other materials, compounds and reagents known to those skilled in the art. All such compounds, stereoisomers, racemic mixtures, diastereomers and enantiomers thereof are intended to be encompassed within the scope of the present invention. Since the scheme is an illustration, the invention should not be construed as being limited by the chemical reactions and conditions expressed. The preparation of the various starting materials used in the scheme is well within the skill of persons versed in the art.

In the following general method for preparing compounds of the invention, isocyanate Compound AA1 was condensed with ethyl glyoxalate to form a derivative of Compound AA1 which underwent [4+2] cycloaddition with cyclohexa-diene to furnish Compound AA2, having a [2.2.2] bicyclic ring system. Other compounds of the present invention having a tosyl substituent were prepared using appropriate reagents and starting materials known to those skilled in the art, such as using tosyl isocyanate for Compound AA1. Similarly, additional compounds of the present invention having [2.2.1] or [2.1.1] bicyclic ring systems were prepared using appropriate reagents and starting materials known to those skilled in the art for the cycloaddition of the derivative of Compound AA1.

Compound AA2 was reduced by hydrogenation and saponified with sodium hydroxide to yield the acid Compound AA3. Other compounds of the present invention having a double bond in the bicyclic ring system may be prepared by avoiding the reduction step. Optionally, a hydroxy substituent is attached to the bicyclic ring system of Compound AA2 by hydroboration; further substitutions on the bicyclic ring system, by replacement of the hydroxy group, may be carried out by methods known to those skilled in the art.

(S)-4-Nitrophenylalanine methyl ester was acylated with Compound AA3, in the presence an appropriate coupling agent, base and solvent. An appropriate coupling agent may include, and is not limited to, EDAC hydrochloride, DIC, DCC or HATU; an appropriate base may include, and is not limited to, DIEA; and, an appropriate solvent may include, and is not limited to, CH$_2$Cl$_2$ (DCM) or DMF. For compounds of the present invention, (S)-4-Nitrophenylalanine methyl ester was acylated with Compound AA3 in the presence of EDAC, DIEA and DCM. Other compounds of the present invention may obviously be prepared by acylating (S)-4-Nitrophenylalanine methyl ester with Compound AA3 in the presence of appropriate coupling agents, bases and solvents.

The (S,S) diastereomer Compound AA4 was separated, the nitro group was reduced with zinc dust and the resultant amine intermediate was acylated with 2,6-dichlorobenzoyl chloride and the ester saponified with sodium hydroxide to afford Compound AA5. Other compounds of the present invention having a variety of substituents attached to the amide linker of Compound AA5 were prepared by acylating the amine intermediate resulting from the reduction of Compound AA4 with appropriate starting materials known to those skilled in the art.

Similarly, additional compounds of the present invention having a variety of substituents attached directly to the benzyl group of Compound AA4 were prepared by acylating Compound AA3 with appropriate starting materials known to those skilled in the art.

SCHEME AA

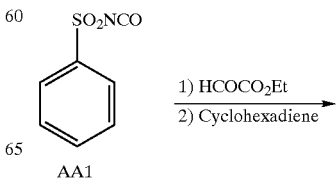

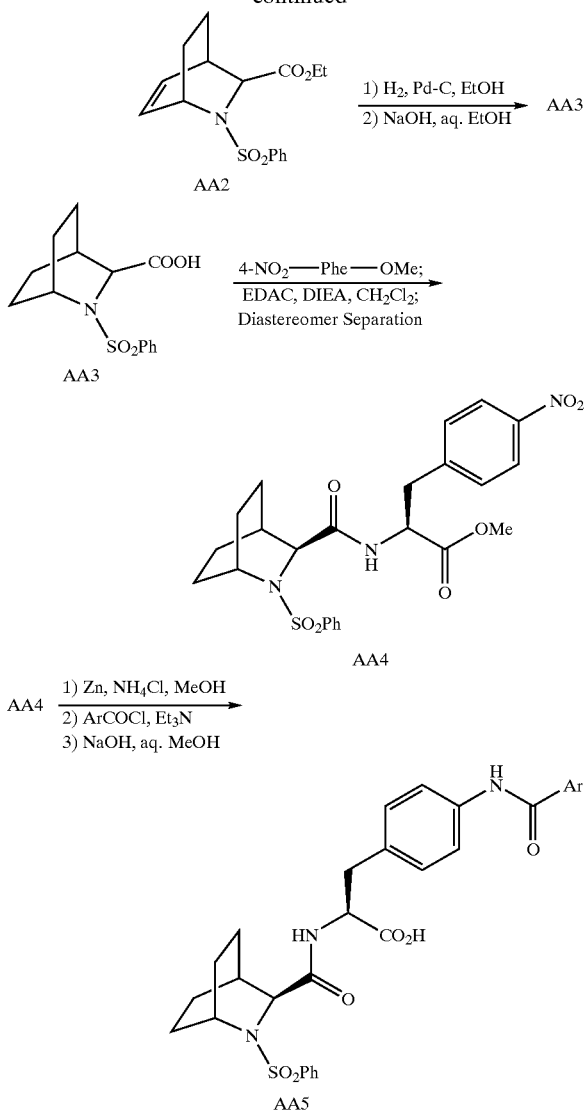

Specific Synthetic Methods

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Microanalyses were performed at Robertson Microlit Laboratories, Inc., Madison, N.J. and are expressed in percentage by weight of each element per total molecular weight.

Nuclear magnetic resonance (NMR) spectra for hydrogen atoms were measured in the indicated solvent with (TMS) as the internal standard on a Bruker AM-360 (360 MHz) spectrometer. The values are expressed in parts per million down field from TMS. The mass spectra (MS) were determined on a Micromass Platform LC spectrometer using electrospray techniques as either (ESI) m/z (M+H$^+$) or (ESI) m/z (M−H$^-$). Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

EXAMPLE 1

4-[(2,6-dichlorobenzoyl)amino]-N-[[(3S)-2-(phenylsulfonyl)-2-azabicyclo[2.2.2]oct-3-yl] carbonyl]-L-phenylalanine (Compound 6a)

A mixture of benzenesulfonyl isocyanate Compound BB1 (18.3 g, 0.10 mol), 20 mL of ethyl glyoxalate (50% solution in toluene, 0.10 mol) and 50 mL of dry toluene was heated at reflux under nitrogen atmosphere for 24 h, then 1,3-cyclohexadiene (20 mL, 0.21 mol) was added in one portion. The mixture was heated for 10 h then cooled to rt, and the white precipitate was filtered off and recrystallized from EtOAc to afford a white crystalline material Compound BB2 (19.1 g).

A suspension of Compound BB2 (19.0 g) with 10% Pd/C (200 mg) and 200 mL of EtOH was hydrogenated for 24 h. The mixture was filtered through celite, and the filtrate was concentrated in vacuo. The residue was recrystallized from EtOAc providing 16.1 g of Compound BB3 (white crystals, $^1$H NMR (CDCl$_3$) 7.98 (d, J=7, 2H), 7.5 (m, 3H), 4.36 (m,1 H), 4.25 (q, J=8, 2H), 3.65 (d, J=3 1H), 2.22 (m,1H), 2.0 (m, 1H), 1.9 (m, 1H), 1.5 (broad m, 6H), 1.28 (t, J=8, 3H). A solution of Compound BB3 in 200 mL of EtOH and 50 mL of 3N NaOH (aq) was stirred for 24 h. The EtOH was removed in vacuo, and the residue was dissolved in 300 mL of water, washed with EtOAc and the organic layer was discarded. The aqueous layer was acidified to pH 2 with 1N HCl (aq), then extracted repeatedly with EtOAc. The combined organic layers were dried over MgSO$_4$, filtered and concentrated to yield 9.5 g of white crystalline Compound BB4. $^1$H NMR (CDCl$_3$) 7.98 (d, J=7, 2H), 7.5 (m, 3H), 4.36 (m,1H), 3.70 (d, J=3, 1H), 2.30 (m, 1H), 2.0 (m, 1H), 1.9–1.3 (broad m, 7H).

A mixture of Compound BB4, (S)-4-nitrophenylalanine methyl ester hydrochloride (6.75 g, 1 eq), EDAC hydrochloride (5.0 g), DIEA (3 eq) and 150 mL DCM was stirred for 5 h at room temperature, washed sequentially with 50 mL of NaHCO$_3$ (sat'd aq) and 1 N HCl (50 mL), dried (sodium sulfate), and concentrated to give a white solid foam (12.0 g). The solid material was crystallized from hexane-ethyl acetate to afford colorless crystals of Compound BB5 as the (S,S) diastereomer (1.05 g), NMR (CDCl$_3$) 8.14 (d, J=8, 2H), 7.90 (d, J=7, 2H), 7.62 (t, J=7,1H), 7.52 (t, J=7, 2H), 7.38 (d, J=8, 2H), 2.3 (m, 1H), 4.95 (q, J=8, 1H). The stereochemistry of Compound BB5 was confirmed by X-ray analysis. The mother liquor was concentrated and the residue was purified by column chromatography (silica gel; hexane:ethyl acetate, 1:1) to afford a second amide (R,S) diastereomer.

A solution of 1.00 g of Compound BB5 in MeOH was treated with NH$_4$Cl (0.54 g, 5 eq) and zinc dust (4.5 g, 35 eq) and stirred under reflux for 3 h. The reaction was filtered through celite and the filtrate was evaporated. The residue was treated with 10% acetic acid (1 mL), neutralized with sodium bicarbonate, and the product was extracted with EtOAc (3×50 mL). The organic layer was washed with water (15 mL), dried (Na$_2$SO$_4$), and concentrated to give Compound BB6 as a white solid (0.85 g, MS m/e 472.6 (MH+)). A solution of Compound BB6, DCM (9 mL), and TEA (0.24 g, 0.0024 mol) at rt was treated with DBC (0.453 g, 1.2 eq) and stirred for 6 h. The reaction was diluted with DCM (50 mL), washed with saturated sodium bicarbonate (20 mL), dried (Na$_2$SO$_4$), and concentrated. The residue was purified by column chromatography (silica gel; 1:1 ethylacetate:hexane) to afford Compound BB7 as a white solid (1.05 g).

A solution Compound BB7 in 30 mL of MeOH and 10 mL of 3N NaOH (aq) was stirred for 24 h. MeOH was removed in vacuo, and the residue was dissolved in 100 mL of water, washed with EtOAc. The aqueous layer was acidified to pH 2 with 1N HCl (aq) and extracted with EtOAc (3×). The combined organic layers were dried over MgSO$_4$, and concentrated to provide 0.76 g of white crystalline Compound 6a. (ESI) m/z 628 (free acid, M−H$^-$). $^1$H NMR (CDCl$_3$) 7.98 (s, 1H), 7.89 (d, J=8, 2H), 7.65 (m, 2H), 7.54 (t, J=8, 2H), 7.25 (m, 6H), 7.12 (d, J=7, 1H), 4.93 (q, J=7, 1H), 4.08 (d, J=3, 1H), 3.83 (m, 1H), 3.33 (dd, J=13 and 6, 1H), 3.16 (dd, J=13 and 7, 1H), 2.22 (m, 1H), 1.8–1.0 (m, 8H).

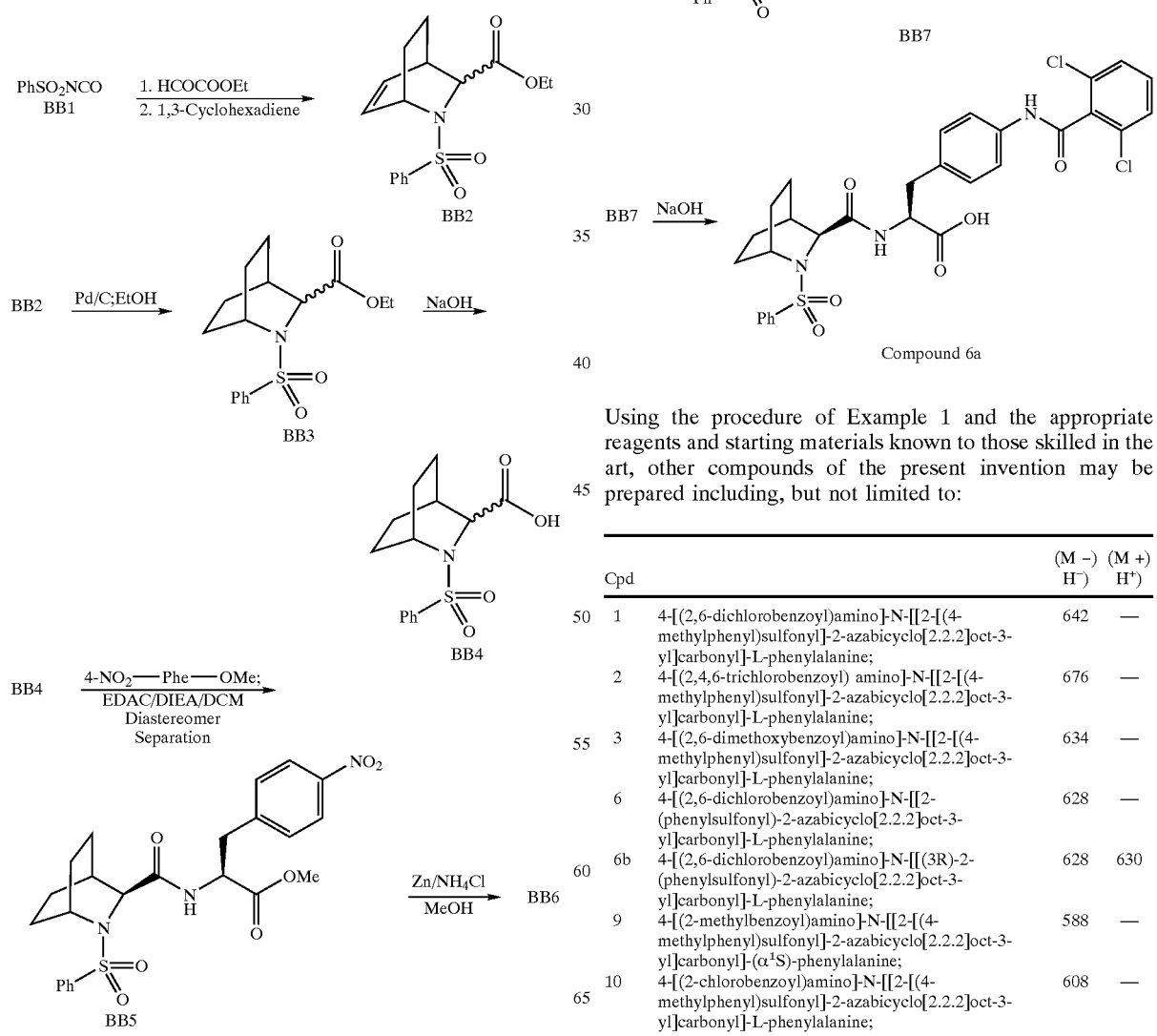

Using the procedure of Example 1 and the appropriate reagents and starting materials known to those skilled in the art, other compounds of the present invention may be prepared including, but not limited to:

| Cpd | | (M −) H$^-$) | (M +) H$^+$) |
|---|---|---|---|
| 1 | 4-[(2,6-dichlorobenzoyl)amino]-N-[[2-[(4-methylphenyl)sulfonyl]-2-azabicyclo[2.2.2]oct-3-yl]carbonyl]-L-phenylalanine; | 642 | — |
| 2 | 4-[(2,4,6-trichlorobenzoyl) amino]-N-[[2-[(4-methylphenyl)sulfonyl]-2-azabicyclo[2.2.2]oct-3-yl]carbonyl]-L-phenylalanine; | 676 | — |
| 3 | 4-[(2,6-dimethoxybenzoyl)amino]-N-[[2-[(4-methylphenyl)sulfonyl]-2-azabicyclo[2.2.2]oct-3-yl]carbonyl]-L-phenylalanine; | 634 | — |
| 6 | 4-[(2,6-dichlorobenzoyl)amino]-N-[[2-(phenylsulfonyl)-2-azabicyclo[2.2.2]oct-3-yl]carbonyl]-L-phenylalanine; | 628 | — |
| 6b | 4-[(2,6-dichlorobenzoyl)amino]-N-[[(3R)-2-(phenylsulfonyl)-2-azabicyclo[2.2.2]oct-3-yl]carbonyl]-L-phenylalanine; | 628 | 630 |
| 9 | 4-[(2-methylbenzoyl)amino]-N-[[2-[(4-methylphenyl)sulfonyl]-2-azabicyclo[2.2.2]oct-3-yl]carbonyl]-($\alpha^1$S)-phenylalanine; | 588 | — |
| 10 | 4-[(2-chlorobenzoyl)amino]-N-[[2-[(4-methylphenyl)sulfonyl]-2-azabicyclo[2.2.2]oct-3-yl]carbonyl]-L-phenylalanine; | 608 | — |

-continued

| Cpd | | (M −)H⁻ | (M +)H⁺ |
|---|---|---|---|
| 11 | 4-[(2,6-difluorobenzoyl)amino]-N-[[2-[(4-methylphenyl)sulfonyl]-2-azabicyclo[2.2.2]oct-3-yl]carbonyl]-L-phenylalanine; | 610 | — |
| 12 | 4-[[2-(trifluoromethyl)benzoyl]amino]-N-[[2-[(4-methylphenyl)sulfonyl]-2-azabicyclo[2.2.2]oct-3-yl]carbonyl]-L-phenylalanine; | 642 | — |
| 13 | 4-[[2-(trifluoromethoxy)benzoyl]amino]-N-[[2-[(4-methylphenyl)sulfonyl]-2-azabicyclo[2.2.2]oct-3-yl]carbonyl]-L-phenylalanine; | 658 | — |
| 14 | 4-[(2-bromobenzoyl)amino]-N-[[2-[(4-methylphenyl)sulfonyl]-2-azabicyclo[2.2.2]oct-3-yl]carbonyl]-L-phenylalanine; | 666 | 655 |
| 15 | 4-[(2,6-difluorobenzoyl)amino]-N-[[2-(phenylsulfonyl)-2-azabicyclo[2.2.2]oct-3-yl]carbonyl]-L-phenylalanine; | 596 | — |
| 25 | 4-(benzoylamino)-N-[[2-[(4-methylphenyl)sulfonyl]-2-azabicyclo[2.2.2]oct-3-yl]carbonyl]-L-phenylalanine; | 575 | — |
| 26 | 4-[4-(2,5-dimethoxybenzoyl)benzoyl]amino]-N-[[2-[(4-methylphenyl)sulfonyl]-2-azabicyclo[2.2.2]oct-3-yl]carbonyl]-L-phenylalanine; | — | 740 |
| 27 | 4-[[(2,6-dichlorophenyl)acetyl]amino]-N-[[2-[(4-methylphenyl)sulfonyl]-2-azabicyclo[2.2.2]oct-3-yl]carbonyl]-L-phenylalanine; | 658 | — |
| 28 | 4-[[[(2,6-dichlorophenyl)amino]carbonyl]amino]-N-[[2-(phenylsulfonyl)-2-azabicyclo[2.2.2]oct-3-yl]carbonyl]-L-phenylalanine; | 643 | — |
| 29 | 4-[(2,6-dichlorophenyl)methoxy]-N-[[(3S)-2-[(4-methylphenyl)sulfonyl]-2-azabicyclo[2.2.2]oct-3-yl]carbonyl]-L-phenylalanine; | — | 617 |
| 30 | 4-(phenylmethoxy)-N-[[2-[(4-methylphenyl)sulfonyl]-2-azabicyclo[2.2.2]oct-3-yl]carbonyl]-L-phenylalanine; | 561 | — |
| 31 | 4-[[2,4,6-tris(1-methylethyl)benzoyl]amino]-N-[[2-[(4-methylphenyl)sulfonyl]-2-azabicyclo[2.2.2]oct-3-yl]carbonyl]-L-phenylalanine; | 701 | 702 |
| 34 | 4-[[[(2,6-difluorophenyl)amino]carbonyl]amino]-N-[[2-(phenylsulfonyl)-2-azabicyclo[2.2.2]oct-3-yl]carbonyl]-L-phenylalanine; | 611 | 612 |
| 35 | 3-[(2,6-difluorobenzoyl)amino]-N-[[2-[(4-methylphenyl)sulfonyl]-2-azabicyclo[2.2.2]oct-3-yl]carbonyl]-L-phenylalanine; | 610 | — |
| 36 | 3-[(2,6-dimethoxybenzoyl)amino]-N-[[2-[(4-methylphenyl)sulfonyl]-2-azabicyclo[2.2.2]oct-3-yl]carbonyl]phenylalanine; | 635 | 636 |
| 37 | 3-[(2,6-dichlorobenzoyl)amino]-N-[[2-[(4-methylphenyl)sulfonyl]-2-azabicyclo[2.2.2]oct-3-yl]carbonyl]phenylalanine; | 644 | 645 |
| 38 | O-[(2,6-dichlorophenyl)methyl]-methyl-N-[[2-(phenylsulfonyl)-2-azabicyclo[2.2.2]oct-3-yl]carbonyl]tyrosine; | — | 631 |
| 39 | 4-[(2,6-dichlorobenzoyl)amino]-N-methyl-N-[[(3R)-2-(phenylsulfonyl)-2-azabicyclo[2.2.2]oct-3-yl]carbonyl]-L-phenylalanine; | — | 644 |
| 40 | O-[(2,6-dichlorophenyl)methyl]-N-[[2-(phenylsulfonyl)-2-azabicyclo[2.2.2]oct-5-en-3-yl]carbonyl]-L-tyrosine; | — | 616 |
| 41 | O-[(2,6-dichlorophenyl)methyl]-N-[[(3R)-2-(phenylsulfonyl)-2-azabicyclo[2.2.2]oct-3-yl]carbonyl]-L-tyrosine; | — | 617 |
| 42 | 4-[(2,6-dichlorobenzoyl)amino]-N-[[2-(phenylsulfonyl)-2-azabicyclo[2.2.2]oct-5-en-3-yl]carbonyl]-L-phenylalanine; | — | 628 |
| 43 | 4-[(2,4,6-trifluorobenzoyl)amino]-N-[[2-(phenylsulfonyl)-2-azabicyclo[2.2.2]oct-3-yl]carbonyl]-L-phenylalanine; | 614 | — |
| 44 | 4-[(2,3,5,6-tetrafluorobenzoyl)amino]-N-[[2-(phenylsulfonyl)-2-azabicyclo[2.2.2]oct-3-yl]carbonyl]-L-phenylalanine; | — | 634 |
| 48 | 4-[(2-carboxybenzoyl)amino]-N-[[(3S)-2-(phenylsulfonyl)-2-azabicyclo[2.2.2]oct-3-yl]carbonyl]-L-phenylalanine; | — | 606 |
| 50 | 4-[(4-pyridinylcarbonyl)amino]-N-[[2-(phenylsulfonyl)-2-azabicyclo[2.2.2]oct-3-yl]carbonyl]-L-phenylalanine; | — | 563 |
| 50a | 4-[(4-pyridinylcarbonyl)amino]-N-[[(3S)-2-(phenylsulfonyl)-2-azabicyclo[2.2.2]oct-3-yl]carbonyl]-L-phenylalanine; | — | 563 |
| 51 | 4-[[(2,6-dichlorophenyl)sulfonyl]amino]-N-[[2-(phenylsulfonyl)-2-azabicyclo[2.2.2]oct-3-yl]carbonyl]-L-phenylalanine; | — | 666 |
| 53 | 4-[[[1-[(1,1-dimethylethoxy)carbonyl]-4-piperidinyl]carbonyl]amino]-N-[[2-(phenylsulfonyl)-2-azabicyclo[2.2.2]oct-3-yl]carbonyl]-L-phenylalanine; | — | 669 |
| 53a | 4-[[[1-[(1,1-dimethylethoxy)carbonyl]-4-piperidinyl]carbonyl]amino]-N-[[(3S)-2-(phenylsulfonyl)-2-azabicyclo[2.2.2]oct-3-yl]carbonyl]-L-phenylalanine; | — | 669 |
| 54 | 4-[(2,6-dichlorobenzoyl)amino]-N-[[2-[(4-fluorophenyl)sulfonyl]-2-azabicyclo[2.2.2]oct-3-yl]carbonyl]-L-phenylalanine; | — | 648 |
| 55 | 4-[(2,6-dimethoxybenzoyl)amino]-N-[[2-[(4-fluorophenyl)sulfonyl]-2-azabicyclo[2.2.2]oct-3-yl]carbonyl]-L-phenylalanine; | — | 640 |
| 59 | 4-[(4-piperidinylcarbonyl)amino]-N-[[2-(phenylsulfonyl)-2-azabicyclo[2.2.2]oct-3-yl]carbonyl]-L-phenylalanine; | — | 569 |
| 60 | 4-[[(3,5-dichloro-4-pyridinyl)carbonyl]amino]-N-[[(3S)-2-(phenylsulfonyl)-2-azabicyclo[2.2.2]oct-3-yl]carbonyl]-L-phenylalanine; | — | 631 |
| 61 | 4-[[(dimethylamino)carbonyl]amino]-N-[[2-(phenylsulfonyl)-2-azabicyclo[2.2.2]oct-3-yl]carbonyl]-L-phenylalanine; | — | 529 |
| 62a | O-[(2,6-dichlorophenyl)methyl]-3-fluoro-N-[[(3S)-2-(phenylsulfonyl)-2-azabicyclo[2.2.2]oct-3-yl]carbonyl]-L-tyrosine; | — | 635 |
| 62b | O-[(2,6-dichlorophenyl)methyl]-3-fluoro-N-[[(3R)-2-(phenylsulfonyl)-2-azabicyclo[22.2]oct-3-yl]carbonyl]-D-tyrosine; | — | 635 |
| 62c | O-[(2,6-dichlorophenyl)methyl]-3-fluoro-N-[[(3S)-2-(phenylsulfonyl)-2-azabicyclo[2.2.2]oct-3-yl]carbonyl]-D-tyrosine; | — | 635 |
| 62d | O-[(2,6-dichlorophenyl)methyl]-3-fluoro-N-[[(3R)-2-(phenylsulfonyl)-2-azabicyclo[2.2.2]oct-3-yl]carbonyl]-L-tyrosine; | — | 635 |
| 64 | 4-[(2,2-dimethyl-1-oxopropyl)amino]-N-[[(3S)-2-(phenylsulfonyl)-2-azabicyclo[2.2.2]oct-3-yl]carbonyl]-L-phenylalanine; | — | 542 |
| 65 | 4-[[(2-ethoxy-1-naphthalenyl)carbonyl]amino]-N-[[(3S)-2-(phenylsulfonyl)-2-azabicyclo[2.2.2]oct-3-yl]carbonyl]-L-phenylalanine; | — | 656 |
| 67 | 4-[(cyclopropylcarbonyl)amino]-N-[[(3S)-2-(phenylsulfonyl)-2-azabicyclo[2.2.2]oct-3-yl]carbonyl]-L-phenylalanine; | — | 526 |
| 68 | 4-[[(2,2,3,3-tetramethylcyclopropyl)carbonyl]amino]-N-[[(3S)-2-(phenylsulfonyl)-2-azabicyclo[2.2.2]oct-3-yl]carbonyl]-L-phenylalanine; | — | 582 |
| 69 | 4-[(2-methyl-1-oxopropyl)amino]-N-[[(3S)-2-(phenylsulfonyl)-2-azabicyclo[2.2.2]oct-3-yl]carbonyl]-L-phenylalanine; | — | 528 |
| 70 | 4-[[[(3S)-2-(phenylsulfonyl)-2-azabicyclo[2.2.2]oct-3-yl]carbonyl]amino]-N-[[(3S)-2-(phenylsulfonyl)-2-azabicyclo[2.2.2]oct-3-yl]carbonyl]-L-phenylalanine; | — | 735 |
| 72 | 4-[[(1-methylcyclopropyl)carbonyl]amino]-N-[[(3S)-2-(phenylsulfonyl)-2-azabicyclo[2.2.2]oct-3-yl]carbonyl]-L-phenylalanine. | — | 540 |

EXAMPLE 2

4-(2,6-dimethoxyphenyl)-N-[[(3S)-2-(phenylsulfonyl)-2-azabicyclo[2.2.2]oct-3-yl]carbonyl]-L-phenylalanine, (Compound 8)

A mixture of Compound BB4 (2.95 g, 1 eq, prepared as in Example 1), (S)-4-iodo-phenylalanine hydrochloride (3.40 g, 1 eq), EDAC hydrochloride (2.5 eq), and DIEA (3 eq) in 50 mL DCM was stirred for 5 h at room temperature, washed sequentially with NaHCO₃ (sat'd, aq), 1 N HCl, dried (Na₂SO₄), and evaporated to give a white solid foam which was crystallized from hexane-ethyl acetate to yield colorless crystals of Compound CC1 as the (S,S) diastereomer (55% yield). $^1$H NMR (CDCl₃) 7.90 (d, J=7, 2H), 7.6 (m, 5H), 7.12 (d, J=8, 1H), 6.93 (d, J=8, 2H), 4.88 (q, J=8, 1H), 4.00 (d, J=4, 1H), 3.81 (d, J=4, 1H), 3.77 (s, 3H), 3.78 (dd, J=14 and 5, 1H), 3.02 (dd, J=14 and 7, 1H), 2.22 (m, 1H), 1.6–0.9 (m, 8H).

To a solution of Compound CC1 (0.64 g) and 0.41 g 2,6-dimethoxyphenylboronic acid (2 eq) in 20 mL of dimethoxyethane under N₂ atmosphere was added 2 mL of 2N solution of K₂CO₃$_{(aq)}$ followed by Pd(PPh₃)₄ (50 mg). The mixture was stirred 24 h at rt under N₂ atmosphere and purified by column chromatography (silica, 1:1 hexane:ethyl acetate). Compound CC2 (0.22 g) was isolated as a white foam. $^1$H NMR (CDCl₃) 7.91 (d, J=7, 2H), 7.8–7.1 (m, 9H), 6.63 (d, 8, 2H), 4.93 (m, 1H), 4.03 (m, 1H), 3.81 (s,1H), 3.79 (s, 3H), 3.69 (s, 6H), 3.31 (dd, J=14 and 6, 1H), 3.05 (dd, J=14 and 9, 1H), 2.21 (m, 1H), 1.6–1.0 (m, 8H).

Compound CC2 (0.2 g) was dissolved in 20 mL of MeOH and 3 mL 3N NaOH (aq). Reaction mixture was stirred overnight, then diluted with 50 mL H₂O, and washed with EtOAc. The aqueous layer was acidified to pH 2 with 1N HCl and extracted 3× with EtOAc. Organic layers were combined, dried over MgSO₄, filtered and evaporated providing 0.12 g of Compound 8 as a white crystalline solid. (ESI) m/z 577 (free acid, M–H⁻).

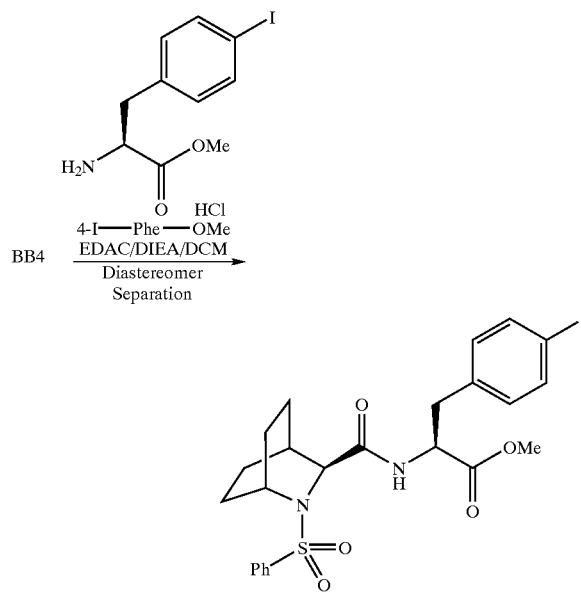

CC1

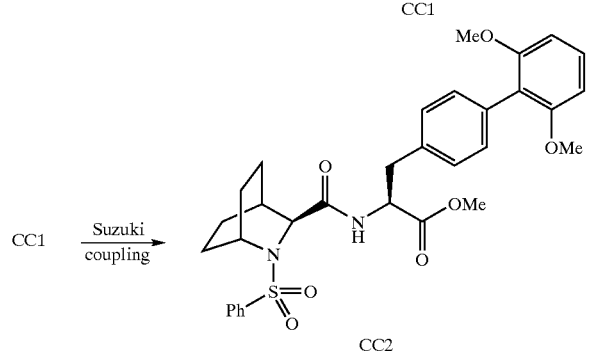

CC2

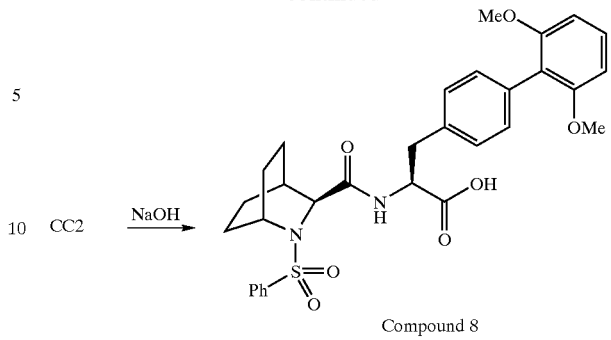

Compound 8

Using the procedure of Example 2 and the appropriate reagents and starting materials known to those skilled in the art, other compounds of the present invention may be prepared including, but not limited to:

| Cpd | | (M −) H⁻ | (M +) H⁺ |
|---|---|---|---|
| 18 | 4-(2,6-dimethoxyphenyl)-N-[[2-[(4-methylphenyl)sulfonyl]-2-azabicyclo[2.2.2]oct-3-yl]carbonyl]-L-phenylalanine; | — | 592 |
| 18a | 4-(2,6-dimethoxyphenyl)-N-[[(3R)-2-[(4-methylphenyl)sulfonyl]-2-azabicyclo[2.2.2]oct-3-yl]carbonyl]-L-phenylalanine; | 591 | 592 |
| 23 | 4-[[4-(1,1-dimethylethyl)phenyl]ethynyl]-N-[[2-[(4-methylphenyl)sulfonyl]-2-azabicyclo[2.2.2]oct-3-yl]carbonyl]-L-phenylalanine; | 611 | — |
| 24 | 4-(phenylethynyl)-N-[[2-[(4-methylphenyl)sulfonyl]-2-azabicyclo[2.2.2]oct-3-yl]carbonyl]-L-phenylalanine; | 555 | — |
| 32 | 4-(1H-pyrrol-1-yl)-N-[[2-[(4-methylphenyl)sulfonyl]-2-azabicyclo[2.2.2]oct-3-yl]carbonyl]-L-phenylalanine; | 520 | — |
| 33 | 4-phenyl-N-[[2-[(4-methylphenyl)sulfonyl]-2-azabicyclo[2.2.2]oct-3-yl]carbonyl]-L-phenylalanine; | 531 | — |
| 45 | O-(1,1-dimethylethyl)-N-[[2-(phenylsulfonyl)-2-azabicyclo[2.2.2]oct-3-yl]carbonyl]-L-tyrosine; | — | 516 |
| 46 | α(S)-[[[2-(phenylsulfonyl)-2-azabicyclo[2.2.2]oct-3-yl]carbonyl]amino]-benzenebutanoic acid; | — | 457 |
| 58 | 4-(1,1-dimethylethyl)-N-[[2-(phenylsulfonyl)-2-azabicyclo[2.2.2]oct-3-yl]carbonyl]-L-phenylalanine. | — | 499 |

EXAMPLE 3

4-[(2,6-difluorobenzoyl)amino]-N-[[(3S)-2-(phenylsulfonyl)-2-azabicyclo[2.2.1]hept-3-yl]carbonyl]-L-phenylalanine (Compound 5a)

(R)-(+)-α-methylbenzylamine Compound DD1 (24.2 g, 0.2 M) was mixed with 40 mL of 50% solution of ethyl glyoxalate in toluene (0.2 M) and the toluene was removed in vacuo. A solution of the resulting residue in 150 mL of DMF, 50 mL of freshly distilled cyclopentadiene, 110 μL of water and 14 mL of TFA was stirred at rt for 24 hr. The mixture was quenched with 50 mL of 1N NaHCO₃ (aq) and diluted with 400 mL of brine. The solution was extracted with ethyl acetate and the organic fraction was dried (MgSO₄) and concentrated. The diastereomers were separated by column chromatography (silica gel; EtOAc:hexane; 1:9) and Compound DD2 (21 g, 40%) was isolated as a yellow oil. A mixture of 21 g of Compound DD2 and 200 mg of Pd(OH)₂ in EtOH was hydrogenated for 24 hr and filtered through a celite pad. The filtrate was concentrated in vacuo, treated with 1N HCl in ether and concentrated. The residue was crystallized from DCM-ether to afford Compound DD3 as white crystals (12.0 g). $^1$H NMR (D$_2$O) 4.70 (s, 2H), 4.47 (q, J=7, 2H), 4.24 (s, 1H), 2.95 (m, 1H), 1.9–1.6 (m, 7H), 1.20 (t, J=7, 3H).

A solution of 2.21 g of Compound DD3 in DCM (50 mL) containing Et$_3$N (2 eq.) was treated with benzenesulfonyl chloride (1.91 g). The mixture was stirred for 3 h, washed with 10% NaHCO$_3$ (aq) and concentrated. The residue was dissolved in 50 mL of MeOH and treated with 10 mL 3N NaOH (aq). The reaction was stirred for 12 hr and MeOH was removed in vacuo. The residue was dissolved in 100 mL H$_2$O, acidified with 1N HCl to a pH of ~2 and extracted with EtOAc to provide a white solid after evaporation. Recrystallization from hexane-EtAc provided a crystalline Compound DD4 (2.5 g). The further transformations were performed using the procedure described in Example 1. Compound 5a was obtained as a white solid: (ESI) m/z 582 (free acid, M–H$^-$).

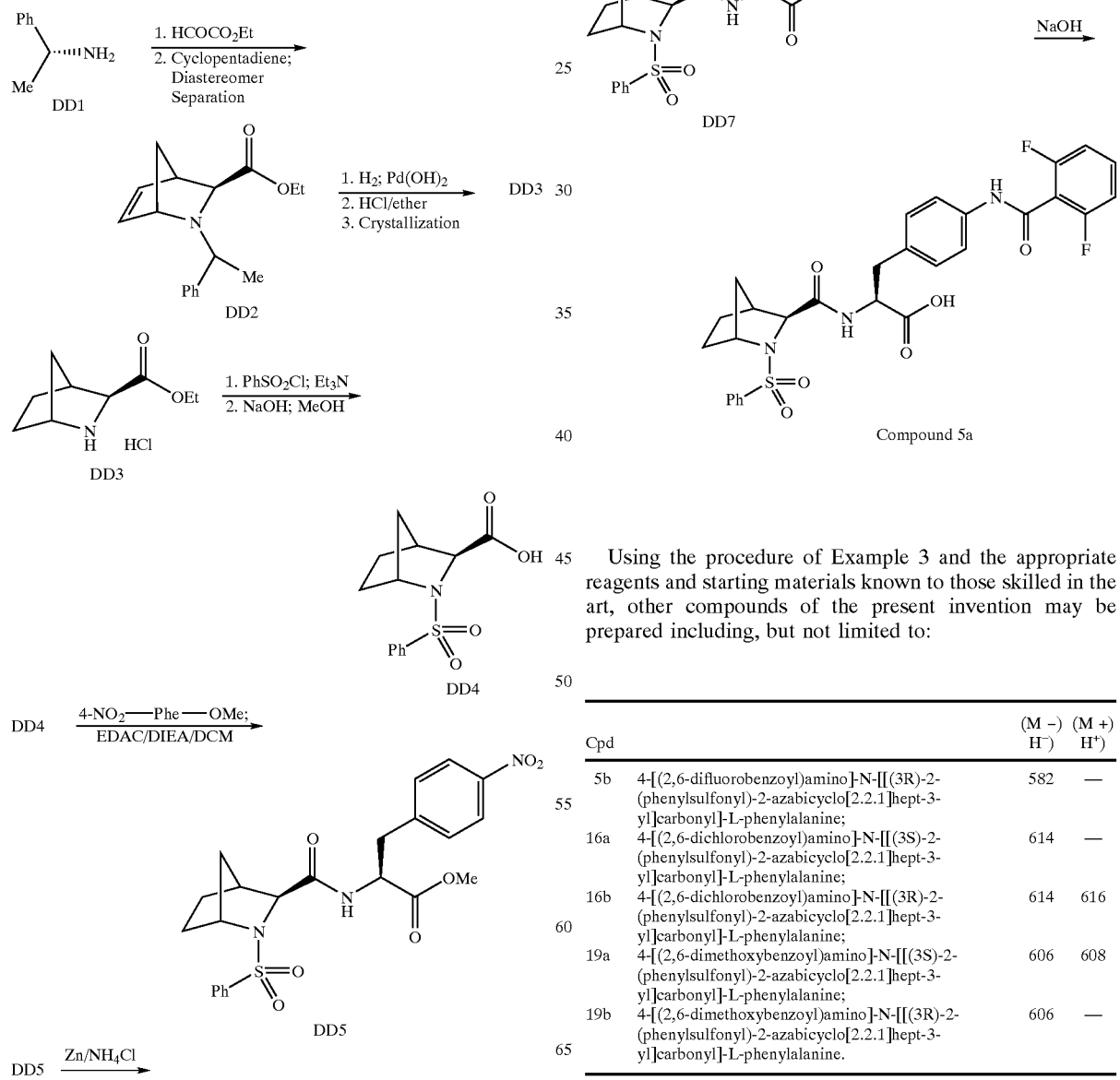

Using the procedure of Example 3 and the appropriate reagents and starting materials known to those skilled in the art, other compounds of the present invention may be prepared including, but not limited to:

| Cpd | | (M −) H$^-$) | (M +) H$^+$) |
|---|---|---|---|
| 5b | 4-[(2,6-difluorobenzoyl)amino]-N-[[(3R)-2-(phenylsulfonyl)-2-azabicyclo[2.2.1]hept-3-yl]carbonyl]-L-phenylalanine; | 582 | — |
| 16a | 4-[(2,6-dichlorobenzoyl)amino]-N-[[(3S)-2-(phenylsulfonyl)-2-azabicyclo[2.2.1]hept-3-yl]carbonyl]-L-phenylalanine; | 614 | — |
| 16b | 4-[(2,6-dichlorobenzoyl)amino]-N-[[(3R)-2-(phenylsulfonyl)-2-azabicyclo[2.2.1]hept-3-yl]carbonyl]-L-phenylalanine; | 614 | 616 |
| 19a | 4-[(2,6-dimethoxybenzoyl)amino]-N-[[(3S)-2-(phenylsulfonyl)-2-azabicyclo[2.2.1]hept-3-yl]carbonyl]-L-phenylalanine; | 606 | 608 |
| 19b | 4-[(2,6-dimethoxybenzoyl)amino]-N-[[(3R)-2-(phenylsulfonyl)-2-azabicyclo[2.2.1]hept-3-yl]carbonyl]-L-phenylalanine. | 606 | — |

EXAMPLE 4

O-[(dimethylamino)carbonyl]-N-[[(3S)-2-(phenylsulfonyl)-2-azabicyclo[2.2.2]oct-3-yl]carbonyl]-L-tyrosine (Compound 52a)

Compound EE1, the (R)-(+)-α-methylbenzylamine (12.1 g), was mixed with 20 mL 50% solution of ethyl glyoxalate in toluene (Fluka) Compound EE2. The reaction was stirred for 30 min and evaporated in vacuo resulting Compound EE3 as a yellow viscous oil. The Compound EE3 oil was dissolved in 300 mL of dry DCM and cooled down in dry ice/acetone bath ($N_2$ atmosphere). TFA (6 mL, 8.81 g) was added dropwise followed by BF3 diethyl etherate (12 mL, 13.5 g). The reaction mixture was stirred for 10 min and 1,3-cyclohexadiene (15 mL) was added dropwise over 30 min period. The reaction was kept in the cooling bath for 3 h, warmed up to rt and stirred for 24 h. The resulting mixture was washed with $NaHCO_3$ 10% aq and evaporated. The residue was subjected to column chromatography (silica, hexane/EtOAc 9:1) providing Compound EE4 as a colorless oil (15.1 g). $^1$H NMR ($CDCl_3$) 7.49–7.40 (m, 2H), 7.27–7.15 (m, 3H), 6.39 (t, J=7, 1H), 6.26 (t, J=5, 1H), 4.20 (q, J=7, 2H), 3.61 (m, 1H), 3.60 (q, J=3, 1H), 2.89 (m, 1H), 2.73 (m, 1H), 2.1–2.0 (m, 1H), 1.63–1.58 (m, 1H), 1.59 (d, J=3, 3H), 1.11 (t, J=7, 3H), 1.3–1.0 (m, 2H).

The suspension of Compound EE4 with 10% Pd/carbon (200 mg) in 200 mL of EtOH was hydrogenated for 24 h (30 psi, rt). The reaction mixture was filtered through celite and concentrated in vacuo providing Compound EE5 as a colorless oil. The solution of Compound EE5 (1.83 g, 0.01 mol) in DCM (100 mL) and $Et_3N$ (280 μl, 2 eq) at 0° C. was treated with $PhSO_2Cl$ (1.77 g, 1 eq) in 20 mL DCM dropwise over 1 h. The ice bath was removed and the mixture stirred for 18 h. The mixture was washed with water (200 mL), 0.1 N HCl, 1 N $NaHCO_3$, dried over $MgSO_4$ and evaporated. The residue was recrystallized from hexane-EtOAc providing Compound EE6 as a white solid (2.58 g, 80%). The ethyl ester was hydrolyzed using NaOH to provide the acid Compound EE7. The acid Compound EE7 (590 mg, 0.002 mol), L- tyrosine methyl ester Compound EEH (400 mg, 0.00205 mol), EDAC (767 mg, 2 eq) and HOBt (540 mg, 2 eq) were dissolved in 10 mL of dry DCM containing 350 μL of DIEA. The solution was stirred at room temperature overnight. The resulting reaction mixture was washed sequentially by $NaHCO_3$ aq. solution, 0.1 N HCl and water, dried and evaporated. The residue was subjected by column chromatography (silica, hexane/EtOAc 1:1) providing Compound EE9 (white solidified foam, 550 mg, 58% yield). A suspension of NaH (84 mg of 60% suspension in oil, washed by hexane) was treated by 10 mL DMF solution of 550 mg of Compound EE9 at 0° C. followed by 100 μl of dimethyl carbamoyl chloride. The mixture was allowed to warm up to room temperature and was stirred overnight. The resulting reaction mixture was diluted by 100 mL of ethyl acetate, washed by NaCl (sat'd aq) and evaporated. The oil was purified by column chromatography (silica, hexane/EtOAc 1:1) to afford 510 mg of Compound EE1 0. A solution of 500 mg of Compound EE10 in 20 mL mixture MeOH: water 10:1 was treated with 60 mg LiOH hydrate. The reaction mixture was stirred 24 hr at room temperature, diluted with 100 mL water and extracted by EtOAc. The organic layer was discarded. The aqueous layer was acidified to pH 2 with 2N HCl (aq), then extracted 3 times with EtOAc. The combined organic layers were dried over $MgSO_4$, filtered and concentrated to yield 420 mg of Compound 52a. The solid material was crystallized from hexane-EtOAc providing 350 mg of pure material. $^1$H NMR ($CDCl_3$) 7.90 (d, J=9, 2H), 7.65–7.50 (m, 3H), 7.35–7.20 (m, 3H), 7.08–7.00 (m, 3H), 4.92–4.85 (m, 1H), 4.05 (broad s, 1H), 3.81 (broad s, 1H), 3.38 (dd, J=15 and 9, 1H, 3.10–3.00 (m, 7H), 2.17 (broad S, 1H), 1.60–1.00 (m, 8H). (ESI) m/z 530 (M+H$^+$).

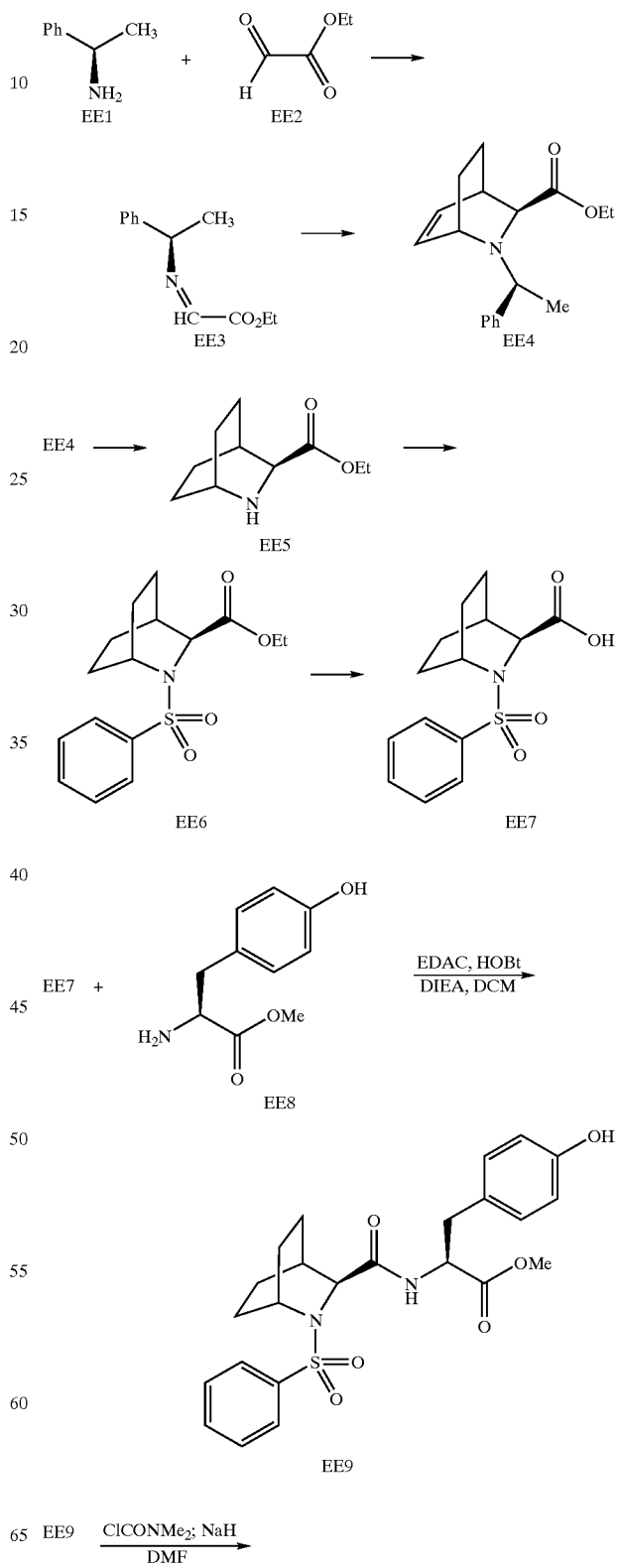

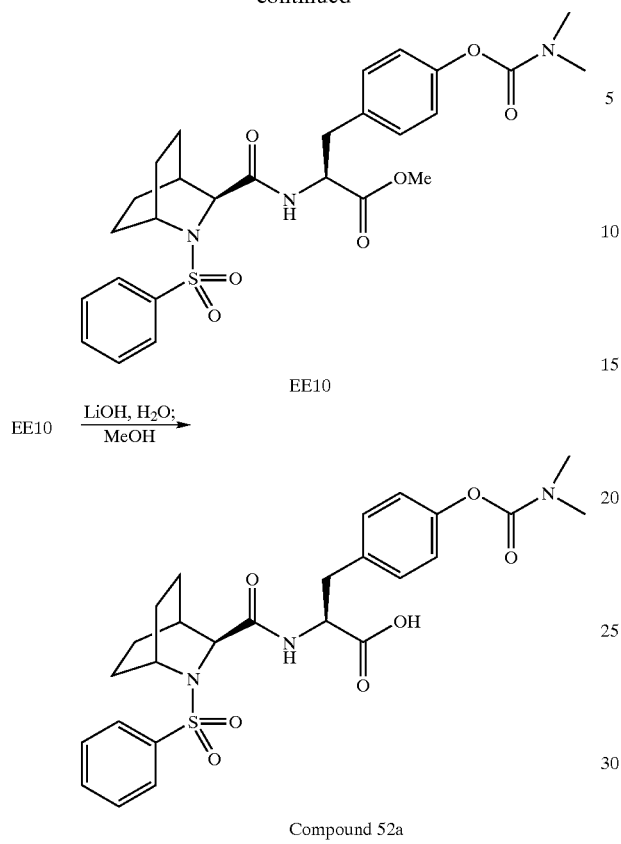

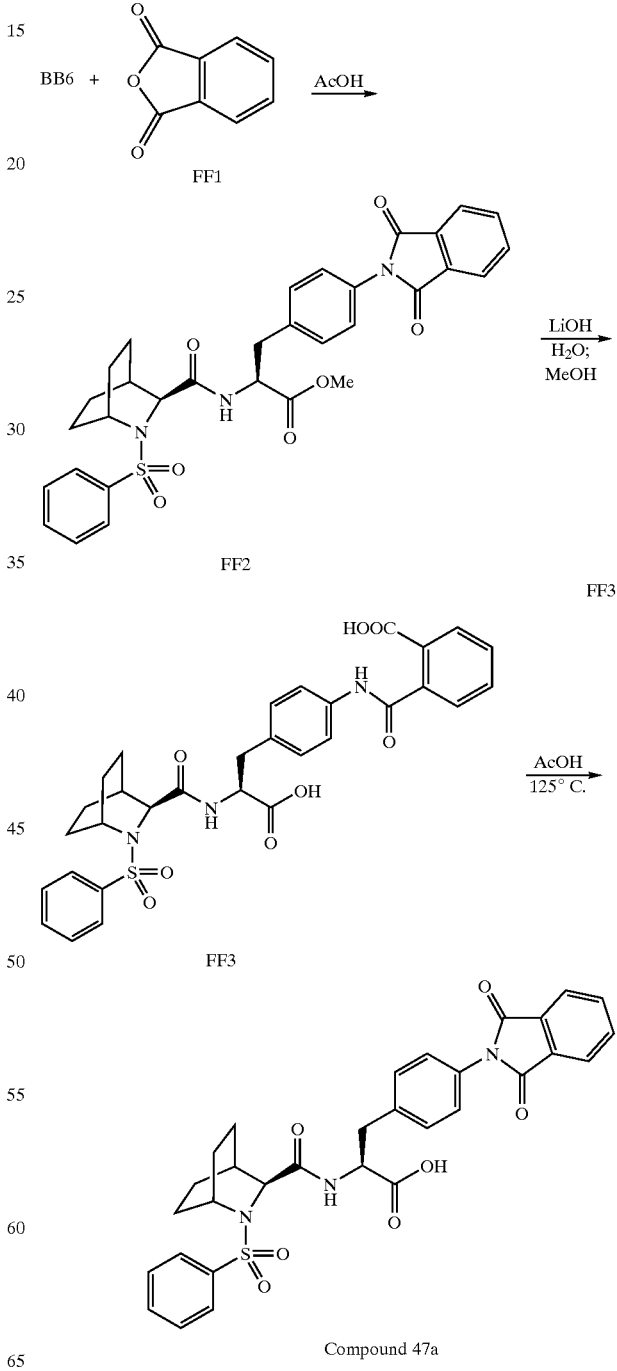

Using the procedure of Example 4 and the appropriate reagents and starting materials known to those skilled in the art, other compounds of the present invention may be prepared including, but not limited to:

| Cpd | | (M + H⁺) |
| --- | --- | --- |
| 52 | O-[(dimethylamino)carbonyl]-N-[[2-(phenylsulfonyl)-2-azabicyclo[2.2.2]oct-3-yl]carbonyl]-L-tyrosine; | 530 |
| 56 | O-(4-morpholinylcarbonyl)-N-[[2-(phenylsulfonyl)-2-azabicyclo[2.2.2]oct-3-yl]carbonyl]-L-tyrosine; | 572 |
| 57 | O-[[bis(1-methylethyl)amino]carbonyl]-N-[[2-(phenylsulfonyl)-2-azabicyclo[2.2.2]oct-3-yl]carbonyl]-L-tyrosine. | 586 |

EXAMPLE 5

4-(1,3-dihydro-1,3-dioxo-2H-isoindol-2-yl)-N-[[(3S)-2-(phenylsulfonyl)-2-azabicyclo[2.2.2]oct-3-yl]carbonyl]-L-phenylalanine (Compound 47a)

A solution of Compound BB6 (prepared as described in Example 1) (471 mg, 0.001 mol) and phthalic anhydride Compound FF1 (150 mg, 0.001 mol) in 10 mL AcOH was heated in the sealed tube at 120° C. for 3 h and cooled to rt. The resulting solution was diluted by 200 mL H₂O and extracted several times by EtOAc. The organic layers were combined, washed with sat'd NaHCO₃ and evaporated. The residue was subjected to column chromatography (silica, hexane:EtOAc, 1:1) providing 450 mg of Compound FF2. Basic hydrolysis (described in the previous examples) resulted in 400 mg of a white solid material (Compound FF3) which was subjected to cyclization without purification. A solution of Compound FF3 (400 mg) in 5 mL AcOH was heated in the sealed tube at 120° C. for 2 h, diluted by 200 mL H₂O and extracted several times by EtOAc. The organic layers were combined, washed by H₂O and concentrated. Column chromatography (silica, CHCl₃/MeOH/AcOH 90:9:1) provided 200 mg of white solid Compound 47a. ¹H NMR (DMSO) 8.1 (m, 1H), 7.97–7.88 (m, 6H), 7.68–7.56 (m, 3H), 7.41 (d, J=8, 2H), 7.34 (d, J=8, 2H), 4.5 (m, 1H), 4.21 (s, 1H), 3.58 (s, 1H), 3.15–3.00 (m, 2H), 2.02 (s, 1H), 1.90–1.70 (m, 1H), 1.50–1.00 (m, 8H). (ESI) m/z 588 (M+H⁺).

Using the procedure of Example 5 and the appropriate reagents and starting materials known to those skilled in the art, other compounds of the present invention may be prepared including, but not limited to:

| Cpd | | (M + H+) |
|---|---|---|
| 47 | 4-(1,3-dihydro-1,3-dioxo-2H-isoindol-2-yl)-N-[[2-(phenylsulfonyl)-2-azabicyclo[2.2.2]oct-3-yl]carbonyl]-L-phenylalanine. | 588 |

EXAMPLE 6

4-(2,5-dimethyl-1H-pyrrol-1-yl)-N-[[2-(phenylsulfonyl)-2-azabicyclo[2.2.2]oct-3-yl]carbonyl]-L-phenylalanine; (Compound 49)

Compound BB6 (using the racemate prepared as described in Example 1) (300 mg, 0.00064 mol) and 2,5-hexanedione Compound GG1 (300 mg, 0.0026 mol) in 80 mL toluene was refluxed with a Dean-Stark trap overnight and cooled to rt. The resulting solution was evaporated and the residue was subjected to column chromatography (silica, hexane:EtOAc, 1:1) providing 320 mg of Compound GG2. Basic hydrolysis (described in the previous examples) resulted in 250 mg of Compound 49, a white solid material. (ESI) m/z 536 (M+H+).

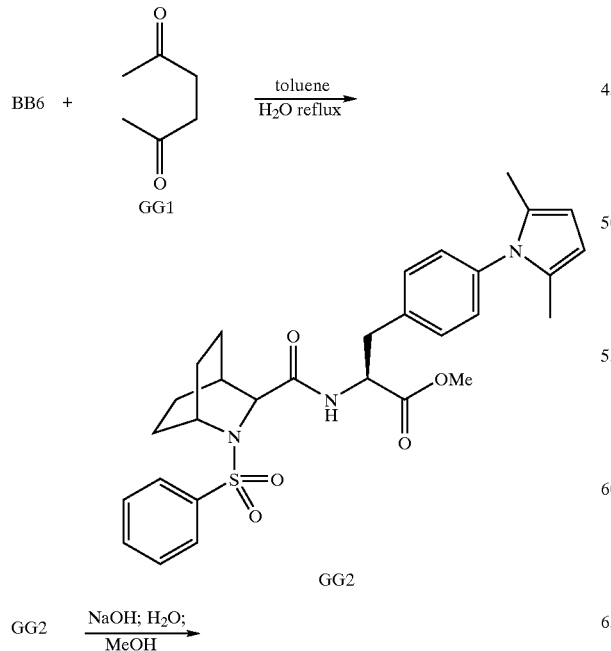

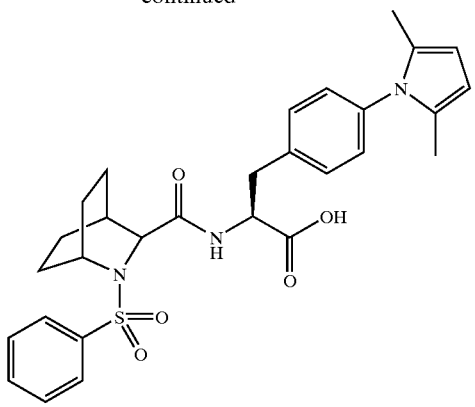

Compound 49

EXAMPLE 7

Compound EE5 (prepared as described in Example 4) (1.83 g, 0.001 mol) in DCM (100 mL) and Et₃N (280 μL, 2 eq) at 0° C. was treated with 2-thiophenesulfonyl chloride Compound HH1 (2.35 g, 1.3 eq) neat as one portion. The ice bath was removed and the mixture stirred for 24 h. The mixture was washed with water (200 mL), 0.1 N HCl, 1 N NaHCO₃, dried over MgSO₄ and evaporated. The residue was purified by column chromatography (silica, hexane:EtOAc, 1:1) and recrystallized from hexane-EtOAc to provide Compound HH2 as white solid (1.97 g, 60%). The ethyl ester was hydrolyzed using NaOH to provide the acid Compound HH3. Compound HH3 was used to replace Compound BB4 or Compound EE7 to obtain other compounds of the invention.

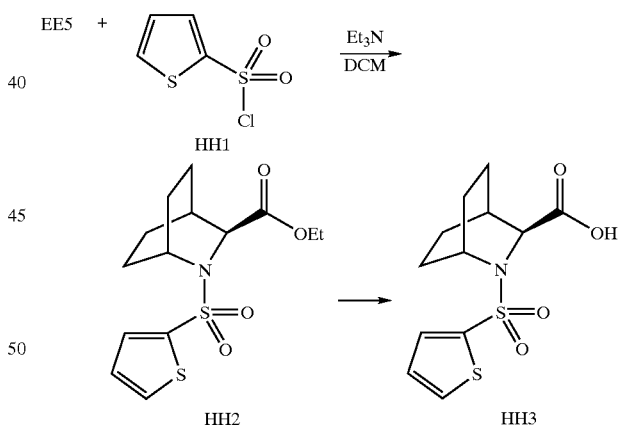

Using the procedure of Example 7 and the appropriate reagents and starting materials known to those skilled in the art, other compounds of the present invention may be prepared including, but not limited to:

| Cpd | | (M + H+) |
|---|---|---|
| 63 | O-[(dimethylamino)carbonyl]-N-[[2-(2-thienylsulfonyl)-2-azabicyclo[2.2.2]oct-3-yl]carbonyl]-L-tyrosine; | 536 |
| 66 | 4-[(2,6-dichlorobenzoyl)amino]-N-[[2-(2-thienylsulfonyl)-2-azabicyclo[2.2.2]oct-3-yl]carbonyl]-L-phenylalanine; | 636 |

-continued

| Cpd | | (M + H$^+$) |
|---|---|---|
| 71 | 4-[[(3,5-dichloro-4-pyridinyl)carbonyl]amino]-N-[[2-(2-thienylsulfonyl)-2-azabicyclo[2.2.2]oct-3-yl]carbonyl]-L-phenylalanine; | 637 |
| 71a | 4-[[(3,5-dichloro-4-pyridinyl)carbonyl]amino]-N-[[(3S)-2-(2-thienylsulfonyl)-2-azabicyclo[2.2.2]oct-3-yl]carbonyl]-L-phenylalanine. | 637 |

Biological Experimental Examples

As demonstrated by biological studies described hereinafter, and shown in Table III and Table IV, the compounds of the present invention are α4β1 and α4β7 integrin receptor antagonists useful in treating integrin mediated disorders including, but not limited to, inflammatory, autoimmune and cell-proliferative disorders.

Ramos Cell Adhesion Assay ($\alpha_4\beta_1$ Mediated Adhesion/VCAM-1)

Immulon 96 well plates (Dynex) were coated with 100 μL recombinant hVCAM-1 at 4.0 μg/mL in 0.05 M NaCO$_3$ buffer pH 9.0 overnight at 4° C. (R&D Systems). Plates were washed 3 times in PBS with 1% BSA and blocked for 1 h @ room temperature in this buffer. PBS was removed and compounds to be tested (50 μL) were added at 2× concentration. Ramos cells, (50 μL at 2×10$^6$/mL) labeled with 5 μM Calcein AM (Molecular Probes) for 1 h at 37° C., were added to each well and allowed to adhere for 1 h at room temperature. Plates were washed 3× in PBS+1% BSA and cells were lysed for 15 minutes in 100 μL of 1 M Tris pH 8.0 with 1% SDS. The plate was read at 485 nm excitation and 530 nm emission.

$\alpha_4\beta_7$-K562 Cell Adhesion Assay ($\alpha_4\beta_7$ Mediated Adhesion/VCAM-1)

Immulon 96 well plates (Dynex) were coated with 100 μL recombinant hVCAM-1 at 4.0 μg/mL in 0.05 M NaCO$_3$ buffer pH 9.0 overnight at 4° C. (R&D Systems). Plates were washed 3 times in PBS with 1% BSA and blocked for 1 h @ room temperature in this buffer. PBS was removed and compounds to be tested (50 μL) were added at 2× concentration. A stable cell line of K562 cells expressing human $\alpha_4\beta_7$, (50 μL at 2×10$^6$/mL) labeled with 5 μM Calcein AM (Molecular Probes) for 1 h at 37° C., were added to each well and allowed to adhere for 1 h at room temperature. Plates were washed 3× in PBS+1% BSA and cells were lysed for 15 minutes in 100 μL of 1 M Tris pH 8.0 with 1% SDS. The plate was read at 485 nm excitation and 530 nm emission.

TABLE III

Inhibition of Binding of Ramos Cells to Immobilized VCAM-1

| Cpd | IC$_{50}$ (nM) | Cpd | IC$_{50}$ (nM) | Cpd | IC$_{50}$ (nM) |
|---|---|---|---|---|---|
| 1 | 45 | 28 | 1600 | 52a | 40 |
| 2 | 51 | 29 | 58 | 53 | 67 |
| 3 | 50 | 30 | >5 μM | 53a | 219 |
| 5a | 81 | 31 | >5 μM | 54 | 146 |
| 5b | 394 | 32 | >5 μM | 55 | 303 |
| 6 | 25 | 33 | >5 μM | 56 | 139 |
| 6a | 21 | 34 | >5 μM | 57 | 757 |
| 6b | 222 | 35 | >5 μM | 58 | 523 |
| 8 | 81 | 36 | >5 μM | 59 | 237 |
| 9 | 267 | 37 | >5 μM | 60 | 9 |
| 10 | 145 | 38 | >5 μM | 61 | 56 |
| 11 | 179 | 39 | >5 μM | 62 | >5 μM |
| 12 | 104 | 40 | 293 | 62a | >5 μM |
| 13 | 119 | 41 | >5 μM | 63 | 112 |
| 14 | 160 | 42 | 22 | 64 | 393 |
| 15 | 67 | 43 | 103 | 65 | 193 |
| 16a | 153 | 44 | 309 | 66 | 17 |
| 16b | 240 | 45 | 3165 | 67 | 628 |
| 18 | 124 | 46 | >5 μM | 68 | 873 |
| 18b | 857 | 47 | 74 | 69 | 455 |
| 19a | 300 | 47a | 26 | 70 | 370 |
| 19b | 1210 | 48 | >5 μM | 71 | 7 |
| 23 | 1420 | 49 | >5 μM | 71a | 360 |
| 24 | 1100 | 50 | 55 | 72 | 4 |
| 25 | 903 | 50a | 54 | | |
| 26 | 669 | 51 | 784 | | |
| 27 | 1090 | 52 | 124 | | |

TABLE IV

Inhibition of Binding of K562 Cells to Immobilized VCAM-1

| Cpd | IC$_{50}$ (nM) | Cpd | IC$_{50}$ (nM) | Cpd | IC$_{50}$ (nM) |
|---|---|---|---|---|---|
| 1 | 142 | 28 | >5 μM | 52a | 436 |
| 2 | 98 | 29 | 4940 | 53 | 871 |
| 3 | 1945 | 30 | >10 μM | 53a | 693 |
| 5a | 62 | 31 | >10 μM | 54 | 118 |
| 5b | 3380 | 32 | >10 μM | 55 | 91 |
| 6 | 283 | 33 | >10 μM | 56 | 47 |
| 6a | 217 | 34 | >10 μM | 57 | >5 μM |
| 6b | 421 | 35 | >10 μM | 58 | >10 μM |
| 8 | 343 | 36 | >10 μM | 59 | 1500 |
| 9 | >5 μM | 37 | >10 μM | 60 | — |
| 10 | 4410 | 38 | >10 μM | 61 | — |
| 11 | 1490 | 39 | >10 μM | 62 | >10 μM |
| 12 | 1080 | 40 | 2510 | 62a | >10 μM |
| 13 | >10 μM | 41 | >10 μM | 63 | 286 |
| 14 | 913 | 42 | 279 | 64 | >10 μM |
| 15 | 1390 | 43 | 442 | 65 | 394 |
| 16a | 2090 | 44 | — | 66 | 186 |
| 16b | 393 | 45 | >10 μM | 67 | 683 |
| 18 | 210 | 46 | >10 μM | 68 | >50 μM |
| 18a | 9000 | 47 | 83 | 69 | 1670 |
| 19a | 3822 | 47a | 102 | 70 | 2035 |
| 19b | 3220 | 48 | >10 μM | 71 | 30 |
| 23 | >10 μM | 49 | >10 μM | 71a | 33 |
| 24 | >10 μM | 50 | 810 | 72 | — |
| 25 | >10 μM | 50a | 223 | | |
| 26 | >10 μM | 51 | >5 μM | | |
| 27 | >10 μM | 52 | 998 | | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of Formula (I):

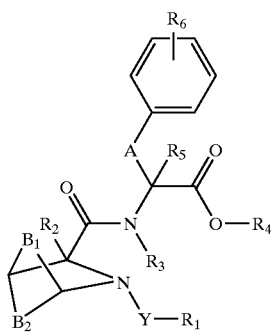

Formula (I)

wherein
Y is selected from the group consisting of a bond, —C(O)—, —C(O)O—, —C(O)NH— and —SO$_2$—;
R$_1$ is R$_7$ or R$_8$;
R$_2$, R$_3$, R$_4$ and R$_5$ are independently hydrogen or C$_{1-8}$alkyl; wherein C$_{1-8}$alkyl is optionally substituted with one to three substituents independently selected from R$_9$;
R$_6$ is optionally present and is one to three substituents independently selected from the group consisting of halogen, C$_{1-8}$alkoxy, R$_{10}$, R$_{12}$, —N(R$_{11}$)C(O)—R$_{10}$, —N(R$_{11}$)C(O)—R$_{12}$, —N(R$_{11}$)SO$_2$—R$_{10}$, —N(R$_{11}$)SO$_2$—R$_{12}$, —N(R$_{11}$)C(O)—N(R$_{11}$, R$_{10}$), —N(R$_{11}$)C(O)—N(R$_{11}$, R$_{12}$), —N(R$_{11}$)C(O)—N(R$_{12}$, R$_{17}$), —C(O)—N(R$_{11}$, R$_{10}$), —C(O)—N(R$_{11}$, R$_{12}$), —C(O)—N(R$_{12}$, R$_{17}$), —OC(O)—N(R$_{11}$, R$_{10}$), —OC(O)—N(R$_{11}$, R$_{12}$), —OC(O)—N(R$_{12}$, R$_{17}$), —OC(O)—R$_{10}$, —OC(O)—R$_{12}$, —O—R$_{10}$ and R$_{10}$—(C$_{1-8}$)alkoxy;
R$_7$, R$_9$ R$_{10}$ and R$_{14}$ are independently selected from the group consisting of cycloalkyl, heterocyclyl, aryl, and heteroaryl optionally substituted with one to five substituents independently selected from the group consisting of halogen, C$_{1-8}$alkyl, C$_{2-8}$alkenyl, C$_{2-8}$alkynyl, C$_{1-8}$alkoxy, C$_{1-8}$alkylcarbonyl, C$_{1-8}$alkoxycarbonyl, carboxyl, aryl, heteroaryl, arylcarbonyl, heteroarylcarbonyl, arylsulfonyl, amino, N—(C$_{1-8}$alkyl)amino, N,N—(C$_{1-8}$dialkyl)amino, —CF$_3$ and —OCF$_3$; wherein cycloalkyl and heterocyclyl are optionally substituted with one to three oxo substituents; and, wherein the aryl and heteroaryl substituents and the aryl portion of the arylcarbonyl substituent are optionally substituted with one to five substituents independently selected from the group consisting of halogen, C$_{1-8}$alkyl, C$_{2-8}$alkenyl, C$_{2-8}$alkynyl, C$_{1-8}$alkoxy, carboxyl, amino, N—(C$_{1-8}$alkyl)amino, N,N—(C$_{1-8}$dialkyl)amino, —CF$_3$ and —OCF$_3$;
R$_8$, R$_{12}$, R$_{13}$ and R$_{17}$ are independently selected from the group consisting of C$_{1-8}$alkyl, C$_{2-8}$alkenyl, C$_{2-8}$alkynyl, and (halo)$_{1-3}$(C$_{1-8}$)alkyl; wherein C$_{1-8}$alkyl, C$_{2-8}$alkenyl and C$_{2-8}$alkynyl are optionally substituted on a terminal carbon with one to three substituents independently selected from R$_{14}$;
R$_{11}$ is hydrogen or C$_{1-8}$alkyl;
A is C$_{1-4}$alkylene optionally substituted with one to two substituents independently selected from R$_{13}$;
B$_1$ and B$_2$ are independently selected from the group consisting of C$_{1-2}$alkylene and C$_2$alkenylene optionally substituted with one to two substituents independently selected from the group consisting of halogen, hydroxy, hydroxy(C$_{1-8}$)alkyl, hydroxy (C$_{1-8}$) alkoxy, C$_{1-8}$alkyl, C$_{2-8}$alkenyl, C$_{2-8}$alkynyl, C$_{1-8}$alkoxy, carboxyl, amino, N—(C$_{1-8}$alkyl)amino, N,N—(C$_{1-8}$dialkyl)amino, —CF$_3$ and —OCF$_3$; and pharmaceutically acceptable salts, racemic mixtures, diastereomers and enantiomers thereof.
2. The compound of claim 1 wherein Y is —C(O)— or —SO$_2$—.
3. The compound of claim 1 wherein Y is —SO$_2$—.
4. The compound of claim 1 wherein R$_1$ is R$_7$.
5. The compound of claim 1 wherein R$_2$, R$_3$, R$_4$ and R$_5$ are independently hydrogen or C$_{1-4}$alkyl.
6. The compound of claim 1 wherein R$_2$, R$_3$, R$_4$ and R$_5$ are independently hydrogen or methyl.
7. The compound of claim 1 wherein R$_6$ is optionally present and is one to three substituents independently selected from the group consisting of halogen, C$_{1-8}$alkoxy, R$_{10}$, R$_{12}$, —N(R$_{11}$)C(O)—R$_{10}$, —N(R$_{11}$)C(O)—R$_{12}$, —N(R$_{11}$)SO$_2$—R$_{10}$, —N(R$_{11}$)C(O)—N(R$_{11}$, R$_{12}$), —N(R$_{11}$)C(O)—N(R$_{12}$, R$_{17}$), —OC(O)—N(R$_{11}$, R$_{12}$), —OC(O)—N(R$_{12}$, R$_{17}$), —OC(O)—R$_{10}$ and R$_{10}$—(C$_{1-8}$) alkoxy.
8. The compound of claim 1 wherein R$_6$ is optionally present and is one to three substituents independently selected from the group consisting of halogen, C$_{1-4}$alkoxy, R$_{10}$, R$_{12}$, —N(R$_{11}$)C(O)—R$_{10}$, —N(R$_{11}$)C(O)—R$_{12}$, —N(R$_{11}$)SO$_2$—R$_{10}$—, —N(R$_{11}$)C(O)—N(R$_{11}$, R$_{12}$), —N(R$_{11}$)C(O)—N(R$_{12}$, R$_{17}$), —OC(O)—N(R$_{11}$, R$_{12}$), —OC(O)—N(R$_{12}$, R$_{17}$), —OC(O)—R$_{10}$ and R$_{10}$—(C$_{1-4}$) alkoxy.
9. The compound of claim 1 wherein R$_6$ is optionally present and is one to two substituents independently selected from the group consisting of R$_{10}$, —N(R$_{11}$)C(O)—R$_{10}$, —N(R$_{11}$)C(O)—N(R$_{11}$, R$_{12}$), —N(R$_{11}$)C(O)—N(R$_{12}$, R$_{17}$), —OC(O)—N(R$_{11}$, R$_{12}$), —OC(O)—N(R$_{12}$, R$_{17}$) and R$_{10}$-methoxy.
10. The compound of claim 1 wherein R$_7$ is selected from the group consisting of aryl and heteroazyl optionally substituted with one to five substituents independently selected from the group consisting of halogen, C$_{1-8}$alkyl, C$_{2-8}$alkenyl, C$_{2-8}$alkynyl, C$_{1-8}$alkoxy, C$_{1-8}$alkylcarbonyl, C$_{1-8}$alkoxycarbonyl, carboxyl, aryl, heteroaryl, arylcarbonyl, heteroarylcarbonyl, arylsulfonyl, amino, N—(C$_{1-8}$alkyl)amino, N,N—(C$_{1-8}$dialkyl)amino, —CF$_3$ and —OCF$_3$; and, wherein the aryl and heteroaryl substituents and the aryl portion of the arylcarbonyl substituent are optionally substituted with one to five substituents independently selected from the group consisting of halogen, C$_{1-8}$alkyl, C$_{2-8}$alkenyl, C$_{2-8}$alkynyl, C$_{1-8}$alkoxy, carboxyl, amino, N—(C$_{1-8}$alkyl)amino, N,N—(C$_{1-8}$dialkyl)amino, —CF$_3$ and —OCF$_3$.
11. The compound of claim 1 wherein R$_{10}$ is selected from the group consisting of cycloalkyl, heterocyclyl, aryl and heteroaryl optionally substituted with one to five substituents independently selected from the group consisting of halogen, C$_{1-8}$alkyl, C$_{1-8}$alkoxy, C$_{1-8}$alkoxycarbonyl, carboxyl, arylcarbonyl, arylsulfonyl, —CF$_3$ and —OCF$_3$; wherein cycloalkyl and heterocyclyl are optionally substituted with one to three oxo substituents; and wherein the aryl portion of the arylcarbonyl substituent is optionally substituted with one to five substituents independently selected from C$_{1-8}$alkoxy.
12. The compound of claim 1 wherein R$_{10}$ is selected from the group consisting of cyclopropyl, 1,3-dihydro-2H-isoindolyl, 2-azabicyclo[2.2.2]octyl, piperidinyl, morpholinyl, phenyl, naphthalenyl, thienyl, 1H-pyrrolyl and pyridinyl; wherein cyclopropyl, piperidinyl, morpholinyl, phenyl, naphthalenyl, thienyl, 1H-pyrrolyl and pyridinyl are optionally substituted with one to four substituents independently selected from the group consisting of chlorine, fluorine, bromine, methyl, isopropyl, t-butyl, methoxy, t-butoxycarbonyl, carboxyl, phenylcarbonyl, —CF$_3$ and —OCF$_3$; wherein 1,3-dihydro-2H-isoindolyl is optionally substituted with oxo; wherein 2-azabicyclo-[2.2.2]octyl is optionally substituted with phenylsulfonyl, and, wherein the phenyl portion of the phenylcarbonyl substituent is optionally substituted with one to two substituents independently selected from methoxy.

13. The compound of claim 1 wherein R$_{12}$ is selected from the group consisting of C$_{1-8}$alkyl and C$_{2-8}$alkynyl optionally substituted on a terminal carbon with R$_{14}$.

14. The compound of claim 1 wherein R$_{12}$ is selected from the group consisting of C$_{1-4}$alkyl and C$_{2-4}$alkynyl optionally substituted on a terminal carbon with R$_{14}$.

15. The compound of claim 1 wherein R$_{12}$ is t-butyl or ethynyl; wherein ethynyl is optionally substituted on a terminal carbon with a substituent independently selected from R$_{14}$.

16. The compound of claim 1 wherein R$_{14}$ is selected from the group consisting of aryl optionally substituted with one to five substituents independently selected from the group consisting of halogen, C$_{1-8}$alkyl, C$_{2-8}$alkenyl, C$_{2-8}$alkynyl, C$_{1-8}$alkoxy, C$_{1-8}$alkylcarbonyl, C$_{1-8}$alkoxycarbonyl, carboxyl, aryl, heteroaryl, arylcarbonyl, heteroarylcarbonyl, arylsulfonyl, amino, N—(C$_{1-8}$alkyl)amino, N,N—(C$_{1-8}$dialkyl)amino, —CF$_3$ and —OCF$_3$; and, wherein the aryl and heteroaryl substituents and the aryl portion of the arylcarbonyl substituent are optionally substituted with one to five substituents independently selected from the group consisting of halogen, C$_{1-8}$alkyl, C$_{2-8}$alkenyl, C$_{2-8}$alkynyl, C$_{1-8}$alkoxy, carboxyl, amino, N—(C$_{1-8}$alkyl)amino, N,N—(C$_{1-8}$dialkyl)amino, —CF$_3$ and —OCF$_3$.

17. The compound of claim 1 wherein R$_{11}$ is hydrogen or C$_{1-4}$alkyl.

18. The compound of claim 1 wherein R$_{11}$ is hydrogen.

19. The compound of claim 1 wherein A is methylene or ethylene.

20. The compound of claim 1 wherein B$_1$ and B$_2$ are independently selected from the group consisting of —CH$_2$—, —(CH$_2$)$_2$— and —(CH)$_2$— optionally substituted with one to two substituents independently selected from the group consisting of halogen, hydroxy, hydroxy(C$_{1-4}$)alkyl, hydroxy(C$_{1-4}$)alkoxy, C$_{1-4}$alkyl, C$_{2-4}$alkenyl, C$_{2-4}$alkynyl, C$_{1-4}$alkoxy, carboxyl, amino, N—(C$_{1-4}$alkyl)amino, N,N—(C$_{1-4}$dialkyl)amino, —CF$_3$ and —OCF$_3$.

21. The compound of claim 1 wherein B$_1$ is selected from the group consisting of —CH$_2$—, —(CH$_2$)$_2$— and —(CH)$_2$— optionally substituted with one to two substituents independently selected from the group consisting of halogen, hydroxy, hydroxy(C$_{14}$)alkyl, hydroxy(C$_{1-4}$)alkoxy, C$_{1-4}$alkyl, C$_{2-4}$alkenyl, C$_{2-4}$alkynyl, C$_{1-4}$alkoxy, carboxyl, amino, N—(C$_{1-4}$alkyl)amino, N,N—(C$_{1-4}$dialkyl)amino, —CF$_3$ and —OCF$_3$; and wherein, B$_2$ is selected from —(CH$_2$)$_2$—.

22. The compound of claim 1 wherein B$_1$ is —CH$_2$—, —(CH$_2$)$_2$—, or —(CH)$_2$—.

23. The compound of claim 1 wherein the compound of Formula (I) is selected from a compound of the formula:

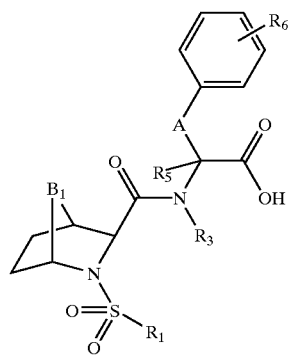

wherein B$_1$, R$_1$, R$_3$, R$_5$, A and R$_6$ are dependently selected from the group consisting of:

| B$_1$ | R$_1$ | R$_3$ | R$_5$ | A | R$_6$ |
|---|---|---|---|---|---|
| (CH$_2$)$_2$ | 4-Tol | H | H | CH$_2$ | 4-NHC(O)-2,6-Cl$_2$)Ph; |
| (CH$_2$)$_2$ | 4-Tol | H | H | CH$_2$ | 4-NHC(O)-(2,4,6-Cl$_3$)Ph; |
| (CH$_2$)$_2$ | 4-Tol | H | H | CH$_2$ | 4-NHC(O)-[2,6-(OMe)$_2$]Ph; |
| CH$_2$ | Ph | H | H | CH$_2$ | 4-NHC(O)-(2,6-F$_2$)Ph; |
| (CH$_2$)$_2$ | Ph | H | H | CH$_2$ | 4-NHC(O)-(2,6-Cl$_2$)Ph; |
| (CH$_2$)$_2$ | Ph | H | H | CH$_2$ | 4-[2,6-(OMe)$_2$]Ph; |
| (CH$_2$)$_2$ | 4-Tol | H | H | CH$_2$ | 4-NHC(O)-(2-Me)Ph; |
| (CH$_2$)$_2$ | 4-Tol | H | H | CH$_2$ | 4-NHC(O)-(2-Cl)Ph; |
| (CH$_2$)$_2$ | 4-Tol | H | H | CH$_2$ | 4-NHC(O)-(2,6-F$_2$)Ph; |
| (CH$_2$)$_2$ | 4-Tol | H | H | CH$_2$ | 4-NHC(O)-(2-CF$_3$)Ph; |
| (CH$_2$)$_2$ | 4-Tol | H | H | CH$_2$ | 4-NHC(O)-(2-OCF$_3$)Ph; |
| (CH$_2$)$_2$ | 4-Tol | H | H | CH$_2$ | 4-NHC(O)-(2-Br)Ph; |
| (CH$_2$)$_2$ | Ph | H | H | CH$_2$ | 4-NHC(O)-(2,6-F$_2$)Ph; |
| CH$_2$ | Ph | H | H | CH$_2$ | 4-NHC(O)-(2,6-Cl$_2$)Ph; |
| (CH$_2$)$_2$ | 4-Tol | H | H | CH$_2$ | 4-[2,6-(OMe)$_2$]Ph; |
| CH$_2$ | Ph | H | H | CH$_2$ | 4-NHC(O)-[2,6-OMe)$_2$]Ph; |
| (CH$_2$)$_2$ | 4-Tol | H | H | CH$_2$ | 4-CC-(4-t-butyl)Ph; |
| (CH$_2$)$_2$ | 4-Tol | H | H | CH$_2$ | 4-CC-Ph; |
| (CH$_2$)$_2$ | 4-Tol | H | H | CH$_2$ | 4-NHC(O)-Ph; |
| (CH$_2$)$_2$ | 4-Tol | H | H | CH$_2$ | 4-NHC(O)-[4-C(O)-[2,5-(OMe)$_2$]Ph]Ph; |
| (CH$_2$)$_2$ | 4-Tol | H | H | CH$_2$ | 4-NHC(O)-CH$_2$-(2,6-Cl$_2$)Ph; |
| (CH$_2$)$_2$ | Ph | H | H | CH$_2$ | 4-NHC(O)-NH-(2,6-Cl$_2$)Ph; |
| (CH$_2$)$_2$ | Ph | H | H | CH$_2$ | 4-OCH$_2$-(2,6-Cl)$_{Ph}$; |
| (CH$_2$)$_2$ | 4-Tol | H | H | CH$_2$ | 4-OCH$_2$-Ph; |

-continued

| B₁ | R₁ | R₃ | R₅ | A | R₆ |
|---|---|---|---|---|---|
| (CH₂)₂ | 4-Tol | H | H | CH₂ | 4-NHC(O)-(2,4,6-isopropyl₃)Ph; |
| (CH₂)₂ | 4-Tol | H | H | CH₂ | 4-(1H-pyrrol-1-yl); |
| (CH₂)₂ | 4-Tol | H | H | CH₂ | 4-Ph; |
| (CH₂)₂ | Ph | H | H | CH₂ | 4-NHC(O)-NH-(2,6-F₂)Ph; |
| (CH₂)₂ | 4-Tol | H | H | CH₂ | 3-NHC(O)-(2,6-F₂)Ph; |
| (CH₂)₂ | 4-Tol | H | H | CH₂ | 3-NHC(O)-[2,6-(OMe)₂]Ph; |
| (CH₂)₂ | 4-Tol | H | H | CH₂ | 3-NHC(O)-(2,6-Cl₂)Ph; |
| (CH₂)₂ | Ph | H | CH₃ | CH₂ | 4-OCH₂-(2,6-Cl₂)Ph; |
| (CH₂)₂ | Ph | CH₃ | H | CH₂ | 4-NHC(O)-(2,6-Cl₂)Ph; |
| CH₂ | Ph | H | H | CH₂ | 4-OCH₂-(2,6-Cl₂)Ph; |
| (CH₂)₂ | Ph | H | H | CH₂ | 4-OCH₂-(2,6-Cl₂)Ph |
| (CH₂)₂ | Ph | H | H | CH₂ | 4-NHC(O)-(2,6-Cl₂)Ph; |
| (CH₂)₂ | Ph | H | H | CH₂ | 4-(2,4,6-F₃)Ph; |
| (CH₂)₂ | Ph | H | H | CH₂ | 4-(2,3,5,6-F₄)Ph; |
| (CH₂)₂ | Ph | H | H | CH₂ | 4-O-t-butoxy; |
| (CH₂)₂ | Ph | H | H | (CH₂)₂ | —; |
| (CH₂)₂ | Ph | H | H | CH₂ | 4-(1,3-dihydro-1,3-dioxo-2H-isoindol-2-yl); |
| (CH₂)₂ | Ph | H | H | CH₂ | 4-NHC(O)-(2-CO₂H)Ph; |
| (CH₂)₂ | Ph | H | H | CH₂ | 4-(2,5-diMe-1H-pyrrol-1-yl); |
| (CH₂)₂ | Ph | H | H | CH₂ | 4-NHC(O)-4-pyridinyl; |
| (CH₂)₂ | Ph | H | H | CH₂ | 4-NHSO₂-(2,6-Cl₂)Ph; |
| (CH₂)₂ | Ph | H | H | CH₂ | 4-OC(O)-N(CH₃)₃; |
| (CH₂)₂ | Ph | H | H | CH₂ | 4-NHC(O)-(1-t-butoxycarbonyl)4-piperidinyl; |
| (CH₂)₂ | 4-FPh | H | H | CH₂ | 4-NHC(O)-(2,6-Cl₂)Ph; |
| (CH₂)₂ | 4-FPh | H | H | CH₂ | 4-NHC(O)-[2,6-(OMe)₂]Ph; |
| (CH₂)₂ | Ph | H | H | CH₂ | 4-OC(O)-4-morpholinyl; |
| (CH₂)₂ | Ph | H | H | CH₂ | 4-OC(O)N(iso-propyl)₃; |
| (CH₂)₂ | Ph | H | H | CH₂ | 4-t-butyl; |
| (CH₂)₂ | Ph | H | H | CH₂ | 4-NHC(O)-4-piperidinyl; |
| (CH₂)₂ | Ph | H | H | CH₂ | 4-NHC(O)-(3,5-Cl₂)4-pyridinyl; |
| (CH₂)₂ | Ph | H | H | CH₂ | 4-NHC(O)-NMe₂; |
| (CH₂)₂ | Ph | H | H | CH₂ | 3-F-4-[OCH₂(2,6-Cl₂)Ph]; |
| (CH₂)₂ | 2-Thi | H | H | CH₂ | 4-OC(O)-NMe₂; |
| (CH₂)₂ | Ph | H | H | CH₂ | 4-NHC(O)-t-butyl; |
| (CH₂)₂ | 2-Thi | H | H | CH₂ | 4-NHC(O)-(2-OMe)1-naphthalenyl; |
| (CH₂)₂ | Ph | H | H | CH₂ | 4-NHC(O)-(2,6-Cl₂)Ph; |
| (CH₂)₂ | Ph | H | H | CH₂ | 4-NHC(O)-cyclopropyl; |
| (CH₂)₂ | Ph | H | H | CH₂ | 4-NHC(O)-(2,2,3,3-Me₄)cyclopropyl; |
| (CH₂)₂ | Ph | H | H | CH₂ | 4-NHC(O)-iso-propyl; |
| (CH₂)₂ | Ph | H | H | CH₂ | 4-NHC(O)-(2-SO₂Ph)-2-azabicyclo[2.2.2]oct-3-yl; |
| (CH₂)₂ | 2-Thi | H | H | CH₂ | 4-NHC(0)-(3,5-Cl₂)4-pyridinyl; |
| (CH₂)₂ | Ph | H | H | CH₂ | 4-NHC(O)-(2-Me)cyclopropyl; |
| (CH₂)₂ | Ph | H | H | CH₂ | 4-(2,6-diMe)Ph; |
| (CH₂)₂ | Ph | H | H | CH₂ | 4-(2,6-Cl₂)Ph; |
| (CH₂)₂ | 2-Thi | H | H | CH₂ | 4-(2,6-Cl₂)Ph; |
| (CH₂)₂ | 2-Thi | H | H | CH₂ | 4-(2,6-diMe)Ph; |
| (CH₂)₂ | 2-Thi | H | H | CH₂ | 4-[2,6-(OMe)₂]Ph; |
| (CH₂)₂ | 2-Thi | H | H | CH₂ | 4-(4-fluoro-1,3-dihydro-1,3-dioxo-2H-isoindol-2-yl); |
| (CH₂)₂ | 2-Thi | H | H | CH₂ | 4-NHC(0)-NMe₂; |
| (CH₂)₂ | 2-Thi | H | H | CH₂ | 4-OC(O)-NMe₂; |
| (CH₂)₂ | 2-Thi | H | H | CH₂ | 4-OC(O)-(4-morpholinyl); |
| (CH₂)₂ | 2-Thi | H | H | CH₂ | 4-OC(O)-(4-Me-1-piperazinyl); |
| (CH₂)₂ | Ph | H | H | CH₂ | 4-OC(O)-(4-Me-1-piperazinyl); |
| (CH₂)₂ | Ph | H | H | CH₂ | 4-N(Me)C(O)-(2,6-Cl₂)Ph; |
| (CH₂)₂ | Ph | H | H | CH₂ | 4-N(Me)C(O)-(3,5-Cl₂)4-pyridinyl; |
| (CH₂)₂ | 2-Thi | H | H | CH₂ | 4-N(Me)C(O)-(3,5-Cl₂)4-pyridinyl; |
| (CH₂)₂ | 2-Thi | H | H | CH₂ | 4-N(Me)C(O)-(2,6-Cl₂)Ph; |
| (CH₂)₂ | 2-Thi | H | H | CH₂ | 4-OCH₂-(2,6-Cl₂)Ph; |
| (CH₂)₂ | 2-Thi | H | H | CH₂ | 4-(1,3-dihydro-1,3-dioxo-2H-isoindol-2-yl); |
| (CH₂)₂ | Ph | H | H | CH₂ | 4-(1,3-dihydro-4,7-dimethyl-1,3-dioxo-2H-isoindol-2-yl); |
| (CH₂)₂ | 2-Thi | H | H | CH₂ | 4-(1,3-dihydro-4,7-dimethyl-1,3-dioxo-2H-isoindol-2-yl); |
| CH₂ | 2-Thi | H | H | CH₂ | 4-NHC(O)-(3,5-Cl₂)4-pyridinyl; |
| CH₂ | 2-Thi | H | H | CH₂ | 4-NHC(O)-(2,6-Cl₂)Ph; |
| (CH₂)₂ | Ph | H | H | CH₂ | 4-(1,1-dioxido-3-oxo-1,2-benzisothiazol-2(3H)-yl); |

-continued

| $B_1$ | $R_1$ | $R_3$ | $R_5$ | A | $R_6$ |
|---|---|---|---|---|---|
| $(CH_2)_2$ and, | Ph | H | H | $CH_2$ | 4-(4-chloro-1,3-dihydro-1,3-dioxo-2H-isoindol-2-yl); |
| $(CH_2)_2$ | Ph | H | H | $CH_2$ | 4-(7,9-dioxo-8-azaspiro[4.5]dec-8-yl); | and pharmaceutically acceptable salts, racemic mixtures, diastereomers and enantiomers thereof.

24. The compound of claim 1 wherein the compound of Formula(I) is:

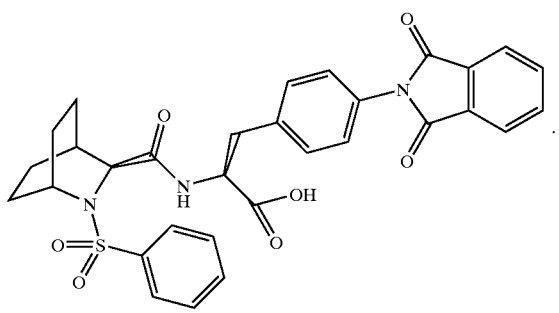

25. The compound of claim 1 wherein the compound of Formula (I) is:

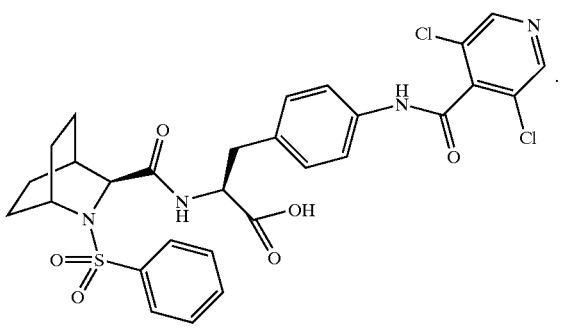

26. The compound of claim 1 wherein the compound of Formula (I) is:

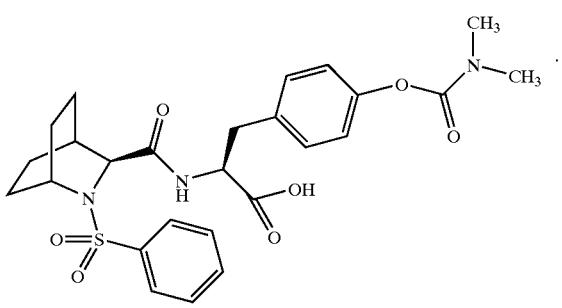

27. The compound of claim 1 wherein the compound of Formula (I) is:

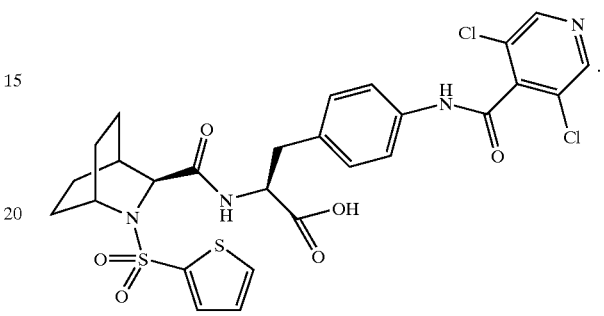

28. The compound of claim 1 wherein the compound is a selective antagonist of an α4 integrin receptor.

29. The compound of claim 28 wherein the α4 integrin receptor is selected from the group consisting of the α4β1 and α4β7 integrin receptor.

30. The compound of claim 28 wherein the compound is an antagonist of at least two α4 integrin receptors.

31. The compound of claim 30 wherein the two α4 integrin receptors are selected from the group consisting of the α4β1 and α4β7 integrin receptor.

32. The compound of claim 1 wherein $R_7$ is selected from the group consisting tolyl, phenyl and thienyl.

33. A compound having Formula (II):

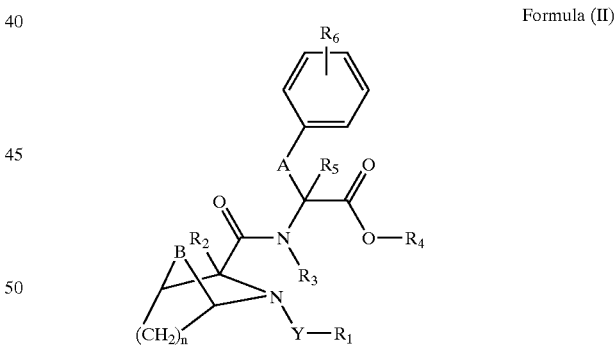

Formula (II)

wherein

Y is selected from the group consisting of —C(O)— and —$SO_2$—;

$R_1$ is selected from the group consisting of $R_7$ and $R_8$;

$R_2$, $R_3$, $R_4$ and $R_5$ are independently hydrogen or $C_{1-8}$alkyl; wherein $C_{1-8}$alkyl is optionally substituted with one to three substituents independently selected from $R_9$;

$R_6$ is optionally present and is one to three substituents independently selected from the group consisting of halogen, $C_{1-8}$alkoxy, $R_{10}$, $R_{12}$, —N($R_{11}$)C(O)—$R_{10}$, —N($R_{11}$)C(O)—$R_{12}$, —N($R_{11}$)$SO_2$—$R_{10}$, —N($R_{11}$)$SO_2$—$R_{12}$, —N($R_{11}$)C(O)—N($R_{11}$, $R_{10}$), —N($R_{11}$)C (O)—N($R_{11}$, $R_{12}$), —N($R_{11}$)C(O)—N($R_{12}$, $R_{17}$), —C(O)—N($R_{11}$, $R_{10}$), —C(O)—N($R_{11}$, $R_{12}$), —C(O)—N($R_{12}$, $R_{17}$), —OC(O)—N($R_{11}$, $R_{10}$), —OC(O)—N($R_{11}$, $R_{12}$), —OC(O)—N($R_{12}$, $R_{17}$), —OC(O)—$R_{10}$, —OC(O)—$R_{12}$, —O—$R_{10}$ and $R_{10}$—($C_{1-8}$) alkoxy;

$R_7$ $R_9$, $R_{10}$ and $R_{14}$ are independently selected from the group consisting of cycloalkyl, heterocyclyl, aryl and heteroaryl optionally substituted with one to five substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, aryl, heteroaryl, arylcarbonyl, heteroarylcarbonyl, arylsulfonyl, amino, N—($C_{1-8}$alkyl)amino, N,N—($C_{1-8}$dialkyl)amino, —$CF_3$ and —$OCF_3$; wherein cycloalkyl and heterocyclyl are optionally substituted with one to three oxo substituents; and, wherein the aryl and heteroaryl substituents and the aryl portion of the arylcarbonyl substituent are optionally substituted with one to five substituents independently selected from the group consisting of halogen, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$;

$R_8$, $R_{12}$, $R_{13}$ and $R_{17}$ are independently selected from the group consisting of $C_{1-8}$alkyl, $C_{2-8}$alkenyl, $C_{2-8}$alkynyl, and (halo)$_{1-3}$($C_{1-8}$)alkyl; wherein $C_{1-8}$alkyl, $C_{2-8}$alkenyl and $C_{2-8}$alkynyl are optionally substituted on a terminal carbon with one to three substituents independently selected from $R_{14}$;

$R_{11}$ is hydrogen or $C_{1-8}$alkyl;

A is $C_{1-4}$alkylene optionally substituted with one to two substituents independently selected from $R_{13}$;

B is selected from the group consisting of $C_{1-2}$alkylene and $C_2$alkenylene optionally substituted with one to two substituents independently selected from the group consisting of halogen, hydroxy, hydroxy ($C_{1-8}$)alkyl, hydroxy ($C_{1-8}$)alkoxy, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$; and n is an integer from 1 to 2;

and pharmaceutically acceptable salts, racemic mixtures, diastereomers and enantiomers thereof.

34. A process for preparing a compound of Formula (III):

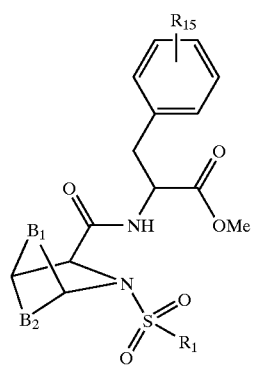

Formula (III)

wherein $R_1$ is selected from the group consisting of $R_7$ and $R_8$;
$R_7$, $R_{10}$, and $R_{14}$ are independently selected from the group consisting of cycloalkyl, heterocyclyl, aryl and heteroaryl optionally substituted with one to five substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, aryl, heteroaryl, arylcarbonyl, heteroarylcarbonyl, arylsulfonyl, amino, N—($C_{1-8}$alkyl)amino, N,N—($C_{1-8}$dialkyl)amino, —$CF_3$ and —$OCF_3$; wherein cycloalkyl and heterocyclyl are optionally substituted with one to three oxo substituents; and, wherein the aryl and heteroaryl substituents and the aryl portion of the arylcarbonyl substituent are optionally substituted with one to five substituents independently selected from the group consisting of halogen, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$;

$R_8$, $R_{12}$ and $R_{17}$ are independently selected from the group consisting of $C_{1-8}$alkyl, $C_{2-8}$alkenyl, $C_{2-8}$alkynyl, and (halo)$_{1-3}$($C_{1-8}$)alkyl; wherein $C_{1-8}$alkyl, $C_{2-8}$alkenyl and $C_{2-8}$alkynyl are optionally substituted on a terminal carbon with one to three substituents independently selected from $R_{14}$;

$R_{15}$ is selected from the group consisting of hydroxy, amino, $NO_2$ and $R_6$;

$R_6$ is optionally present and is one to three substituents independently selected from the group consisting of halogen, $C_{1-8}$alkoxy, $R_{10}$, $R_{12}$, —N($R_{11}$)C(O)—$R_{10}$, —N($R_{11}$)C(O)—$R_{12}$, —N($R_{11}$)$SO_2$—$R_{10}$, —N($R_{11}$)$SO_2$—$R_{12}$, —N($R_{11}$)C(O)—N($R_{11}$, $R_{10}$), —N($R_{11}$)C(O)—N($R_{11}$, $R_{12}$) —N($R_{11}$)C(O)—N($R_{12}$, $R_{17}$), —C(O)—N($R_{11}$, $R_{10}$), —C(O)—N($R_{12}$, $R_{17}$), —C(O)—N($R_{11}$, $R_{12}$), —OC(O)—N($R_{11}$, $R_{10}$), —OC(O)—N($R_{11}$, $R_{12}$), —OC(O)—N($R_{12}$, $R_{17}$), —OC(O)—$R_{10}$, —OC(O)—$R_{12}$, —O—$R_{10}$ and $R_{10}$—($C_{1-8}$) alkoxy;

$R_{11}$ is hydrogen or $C_{1-8}$alkyl; and $B_1$ and $B_2$ are independently selected from the group consisting of $C_{1-2}$alkylene and $C_2$alkenylene optionally substituted with one to two substituents independently selected from the group consisting of halogen, hydroxy, hydroxy($C_{1-8}$)alkyl, hydroxy($C_{1-8}$)alkoxy, $C_{1-8}$alkyl, $C_{2-8}$alkenyl, $C_{2-8}$alkynyl, $C_{1-8}$alkoxy, carboxyl, amino, N—($C_{1-8}$alkyl)amino, N,N—($C_{1-8}$dialkyl)amino, —$CF_3$ and —$OCF_3$;

and pharmaceutically acceptable salts, racemic mixtures, diastereomers and enantiomers thereof; comprising reacting a compound of Formula (IV)

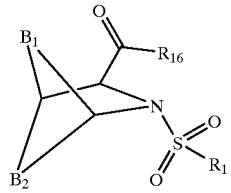

Formula (IV)

wherein $R_{16}$ is selected from the group consisting of halogen, mixed anhydride and hydroxy;

with a compound of Formula (V)

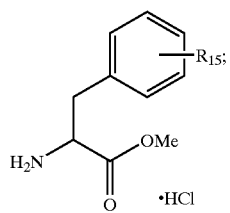

Formula (V)

in the presence of appropriate coupling agents, bases and solvents to form the compound of Formula (II).

35. The process of claim 34 wherein $R_{15}$ is selected from the group consisting of hydroxy, iodine, bromine, and $NO_2$.

36. A pharmaceutical composition comprising a compound of claim 1 and a pharmaceutically acceptable carrier.

37. A pharmaceutical composition made by mixing a compound of claim 1 and a pharmaceutically acceptable carrier.

38. A method of treating integrin mediated disorder selected from the group consisting of asthma, bronchoconstriction, restenosis, atherosclerosis, psoriasis, rheumatoid arthritis, inflammatory bowel disease, irritable bowel disease, irritable bowel syndrome, transplant rejection and multiple sclerosis, comprising administering to a subject in need thereof, a therapeutically effective amount of a compound of claim 1.

39. The method of claim 38 wherein the integrin mediated disorder is selected from the group consisting of asthma, bronchoconstriction, restenosis, atherosclerosis, irritable bowel syndrome and multiple sclerosis.

40. The method of claim 38 wherein the therapeutically effective amount of the compound is from about 0.01 mg/kg/day to about 300 mg/kg/day.

41. The method of claim 38 further comprising administering to a subject in need thereof a therapeutically effective amount of the pharmaceutical composition of the compound and a pharmaceutically acceptable excipient.

42. The method of claim 41 wherein the therapeutically effective amount of the pharmaceutical composition of the compound and a pharmaceutically acceptable excipient is from about 0.01 mg/kg/day to about 300 mg/kg/day.

* * * * *